(12) United States Patent
Junutula et al.

(10) Patent No.: US 10,350,218 B2
(45) Date of Patent: Jul. 16, 2019

(54) ISOQUINOLIDINOBENZODIAZEPINE (IQB)-1(CHLOROMETHYL)-2,3-DIHYDRO-1H-BENZO[E]INDOLE (CBI) DIMERS

(71) Applicant: Cellerant Therapeutics, Inc., San Carlos, CA (US)

(72) Inventors: Jagath R. Junutula, Fremont, CA (US); Sean W. Smith, Lake Forest Park, WA (US); Dmitry Borkin, Feasterville, PA (US); Sylvia Degrado, Newton, PA (US); Sanjeevani Ghone, Plainsboro, NJ (US)

(73) Assignee: Cellerant Therapeutics, Inc., San Carlos, CA (US)

( * ) Notice: Subject to any disclaimer, the term of this patent is extended or adjusted under 35 U.S.C. 154(b) by 0 days.

(21) Appl. No.: 15/904,265

(22) Filed: Feb. 23, 2018

(65) Prior Publication Data

US 2018/0177795 A1 Jun. 28, 2018

Related U.S. Application Data

(63) Continuation of application No. PCT/US2017/055994, filed on Oct. 10, 2017.

(60) Provisional application No. 62/451,658, filed on Jan. 27, 2017, provisional application No. 62/406,077, filed on Oct. 10, 2016.

(51) Int. Cl.

| *A61K 31/5513* | (2006.01) |
|---|---|
| *A61K 31/08* | (2006.01) |
| *A61K 31/16* | (2006.01) |
| *A61K 31/403* | (2006.01) |
| *A61K 31/4439* | (2006.01) |
| *A61K 47/10* | (2017.01) |
| *C07D 471/04* | (2006.01) |
| *A61K 38/05* | (2006.01) |
| *A61K 47/60* | (2017.01) |
| *A61K 47/59* | (2017.01) |
| *A61K 47/68* | (2017.01) |
| *C07K 16/28* | (2006.01) |
| *A61P 35/00* | (2006.01) |

(52) U.S. Cl.
CPC .......... *A61K 31/5513* (2013.01); *A61K 31/08* (2013.01); *A61K 31/16* (2013.01); *A61K 31/403* (2013.01); *A61K 31/4439* (2013.01); *A61K 38/05* (2013.01); *A61K 47/10* (2013.01); *A61K 47/595* (2017.08); *A61K 47/60* (2017.08); *A61K 47/6801* (2017.08); *A61K 47/6803* (2017.08); *A61K 47/6889* (2017.08); *C07D 471/04* (2013.01); *C07K 16/2866* (2013.01); *A61P 35/00* (2018.01); *C07K 2317/24* (2013.01); *C07K 2317/522* (2013.01); *C07K 2317/73* (2013.01)

(58) Field of Classification Search
CPC .... A61K 31/5513; A61K 47/60; A61K 31/08; A61K 31/16; A61K 31/403; A61K 31/4439; A61K 47/10
See application file for complete search history.

(56) References Cited

U.S. PATENT DOCUMENTS

| 4,811,845 A | 3/1989 | Baggett |
|---|---|---|
| 7,528,126 B2 | 5/2009 | Howard et al. |
| 7,612,062 B2 | 11/2009 | Gregson et al. |
| 8,697,688 B2 | 4/2014 | Howard et al. |
| 2002/0058247 A1 | 5/2002 | Sallberg |
| 2003/0007976 A1 | 1/2003 | Watson et al. |
| 2010/0203007 A1 | 8/2010 | Li et al. |
| 2010/0272731 A1 | 10/2010 | Presta et al. |
| 2013/0266596 A1 | 10/2013 | Li et al. |
| 2013/0302357 A1 | 11/2013 | Li et al. |
| 2014/0127239 A1 | 5/2014 | Howard |
| 2015/0165063 A1 | 6/2015 | Flygare et al. |
| 2015/0315279 A1 | 11/2015 | Jiang et al. |
| 2016/0271142 A1 | 9/2016 | Junutula et al. |

FOREIGN PATENT DOCUMENTS

| WO | 1993/018045 A1 | 9/1993 |
|---|---|---|
| WO | 2010036959 | 4/2010 |
| WO | 2013/041606 A1 | 3/2013 |
| WO | 2013/055990 A1 | 4/2013 |
| WO | 2013/055993 A1 | 4/2013 |
| WO | 2018071455 | 4/2018 |
| WO | 2018071910 | 4/2018 |

OTHER PUBLICATIONS

Gregson et al., Linker Length Modulates DNA Cross-Linking Reactivity and Cytotoxic Potency of C8/C8¢ Ether-Linked C2-exo-Unsaturated Pyrrolo[2,1-c][1,4]benzodiazepine (PBD) Dimers, Journal of Medicinal Chemistry, Jan. 30, 2004, 47(5), 1161-1174.
Hartley, The development of pyrrolobenzodiazepines as antitumour agents, Expert Opinion on Investigational Drugs, Apr. 4, 2011, 20(6), 733-744.
Hopton et al., Nuclear Magnetic Resonance Solution Structures of Inter- and Intrastrand Adducts of DNA Cross-Linker SJG-136, Biochemistry, Apr. 13, 2011, 50(21), 4720-4732.
Rahman, et al., Effect of base sequence on the DNA cross-linking properties of pyrrolobenzodiazepine (PBD) dimers, Nucleic Acids Research, Mar. 21, 2011, 39(13), 5800-5812.
Brulikova, L. et al., DNA Interstrand Cross-Linking Agents and their Chemotherapeutic Potential, Current Medicinal Chemistry, 2012, 19(3), 364-385.
Cipolla, L. et al., Pyrrolo[2,1-c][1,4]benzodiazepine as a Scaffold for the Design and Synthesis of Anti-Tumour Drugs, Anti-Cancer Agents in Medicinal Chemistry, Jan. 2009, 9(1), 9.

(Continued)

*Primary Examiner* — Sahar Javanmard
(74) *Attorney, Agent, or Firm* — Kilpatrick Townsend & Stockton LLP

(57) ABSTRACT

Provided herein are isoquinolidinobenzodiazepine (IQB)-1 (chloromethyl)-2,3-dihydro-1H-benzo[e]indole (CBI) dimers, antibody-drug conjugates comprising them and methods of use for killing cells and treating disease.

11 Claims, 28 Drawing Sheets

Specification includes a Sequence Listing.

(56) References Cited

OTHER PUBLICATIONS

Kaliszczak et al., Optimization of the Antitumor Activity of Sequence-specific Pyrrolobenzodiazepine Derivatives Based on their Affinity for ABC Transporters, AAPS Journal, Dec. 2010, 12(4), 617-627.
International Search Report and Written Opinion dated Dec. 7, 2017, from PCT Application No. PCT/US2017/055994 (31 pages).
Tercel, M. et al., Unsymmetrical DNA Cross-Linking Agents: Combination of the CBI and PBD Pharmacophores, J.Med. Chem., 2003, 46(11), 2132-2151.
"UniProtKB—A0A0C9YH80", Retrived from Internet, URL: http://www.uniprot.org/uniprot/A0A0C9YH80, amino acids 7-13, Apr. 29, 2015.
"UniProtKB—F8X0L8", Retrived from Internet, URL: http://www.uniprot.org/uniprot/F8X0L8, amino acids 134-143, Oct. 19, 2011.
"UniProtKB—K7U5TO", Retrived from Internet, URL: http://www.uniprot.org/uniprot/K7U5T0, amino acids 91-100, Feb. 6, 2013.
PCT/US2017/056808 , "International Search Report and Written Opinion Received", dated Apr. 12, 2018, 11 pages.
PCT/US2017/056808 , "Invitation to Pay Add'l Fees and Partial Search Report", dated Feb. 16, 2018, 2 pages.

Scheme 4. Structures of IQB-aminoCB and IQB-hydroxyCBI dimer compounds

ISOQUINOLIDINOBENZODIAZEPINE (IQB)-1(CHLOROMETHYL)-2,3-DIHYDRO-1H-BENZO[E]INDOLE (CBI) DIMERS

REFERENCE TO RELATED APPLICATIONS

The present application is a continuation of PCT International Application No. PCT/US2017/055994, filed Oct. 10, 2017, which application claims the benefit of the filing dates of U.S. Provisional Application No. 62/406,077, filed Oct. 10, 2016 entitled "ISOQUINOLIDINO-DUOCARMYCIN DIMERS", and of U.S. Provisional Application No. 62/451,658, filed Jan. 27, 2017 entitled "ISOQUINOLIDINOBENZODIAZEPINE (IQB)-1(CHLOROMETHYL)-2,3-DIHYDRO-1H-BENZO[E]INDOLE (CBI) DIMERS", the disclosures of all of which are incorporated herein by reference in their entirety for all purposes.

STATEMENT AS TO FEDERALLY SPONSORED RESEARCH

None.

SEQUENCE LISTING

The instant application contains a Sequence Listing which has been submitted electronically in ASCII format and is hereby incorporated by reference in its entirety. Said ASCII copy, created on May 9, 2019, is named 092950-1078992-004820US_SL.txt and is 10,795 bytes in size.

BACKGROUND

Benzodiazapines have been used as therapeutics. Benzodiazepine derivatives include pyrrolobenzodiazepines. Pyrrolobenzodiazepine dimers function as DNA cross-linking agents, e.g., by binding in the minor groove of DNA molecules. Certain of these have been suggested as antiproliferative agents in the treatment of cancer.

Duocarmycins also have been used as therapeutics. Duocarmycins bind to the minor groove of DNA. They alkylate the adenine at the N3 position. The general structure of Duocarmycin has two key components—a DNA alkylation unit, such as 1-(chloromethyl)-2,3-dihydro-1H-benzo[e]indole (CBI), and an indole-2 carbonyl unit that non-covalently binds DNA.

SUMMARY

The present invention provides isoquinolidinobenzodiazepine-1(chloromethyl)-2,3-dihydro-1H-benzo[e]indole ("IQB-CBI") compounds and methods of use thereof. In one aspect, provided herein is a compound having the Formula I:

Formula I

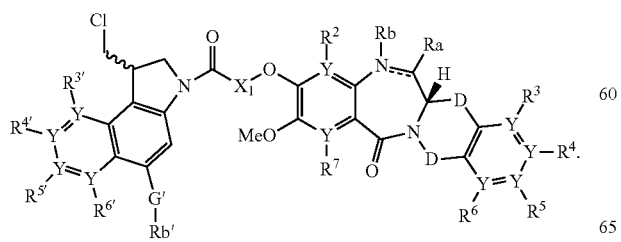

wherein:

the dotted bond shown between —C($R^a$)— and —N($R^b$)— is independently a single bond or a double bond;

when a double bond is present between —C($R^a$)— and —N($R^b$)—, the —C($R^a$)— is olefinic and has a substituent $R^a$, and $R^b$ of the —N($R^b$)— is not present;

when a single bond is present between —C($R^a$)— and —N($R^b$)—, the —C($R^a$)— is saturated and has a hydrogen substituent in addition to the $R^a$ substituent and $R^b$ of the —N($R^b$)— is present;

$R^a$ is independently H, or OH;

if present, $R^b$ is H, L-$R_x$ or -L-Sc;

L-$R_x$ is a linker L attached to a reactive moiety $R_x$, and -L-Sc is a linker L attached to a substance $S_c$; where L, when on its own or when in combination with $R_x$ or Sc, is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; $R_x$ is a reactive moiety; S is a target binding agent selected from a protein, a portion of a protein, a peptide or a nucleic acid;

$R^2$ is selected from H, OH, $C_1$-$C_{10}$ alkyl, $C_2$-$C_{10}$ alkenyl or $C_2$-$C_{10}$ alkynyl;

$R^3$, $R^{3'}$, $R^4$, $R^{4'}$, $R^6$, and $R^{6'}$ are each independently selected from H, OH, $C_1$-$C_{10}$ alkyl, $C_2$-$C_{10}$ alkenyl or $C_2$-$C_{10}$ alkynyl, or, if Y is N, is not present;

each of $R^5$ or $R^{5'}$ is independently $NH_2$, $CO_2H$, H, OH, $C_1$-$C_{10}$ alkyl, $C_2$-$C_{10}$ alkenyl, $C_2$-$C_{10}$ alkynyl, -L-$R_x$ or -L-Sc, or, if Y is N, is not present;

$R^7$ is H;

G'-Rb' is selected from OH, O-L, O-L-$R_x$, O-L-Sc, $NH_2$, NH-L, NH-L-$R_x$, or NH-L-Sc;

each Y is, independently, N or C;

each D is, independently, $(CH_2)_n$ where n=0-4, provided that at least one D is $(CH_2)_n$ where n=1-4;

X1 is any of the listed formulae:

TABLE I

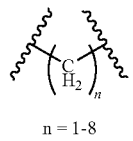

n = 1-8

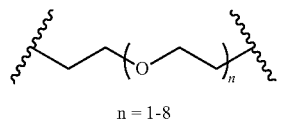

n = 1-8

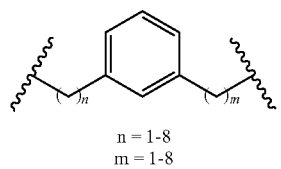

n = 1-8
m = 1-8

TABLE I-continued
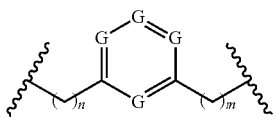
n = 1-8
m = 1-8
G = N, CH
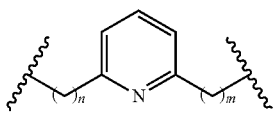
n = 1-8
m = 1-8
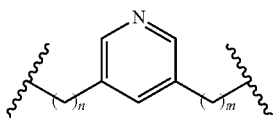
n = 1-8
m = 1-8
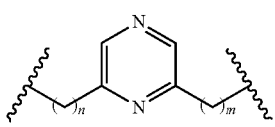
n = 1-8
m = 1-8
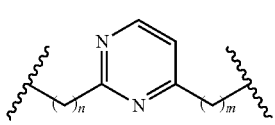
n = 1-8
m = 1-8
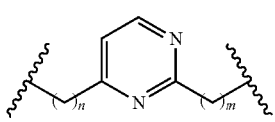
n = 1-8
m = 1-8
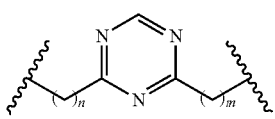
n = 1-8
m = 1-8
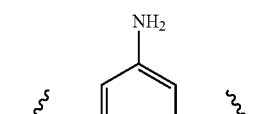
n = 1-8
m = 1-8
TABLE I-continued
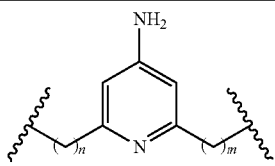
n = 1-8
m = 1-8
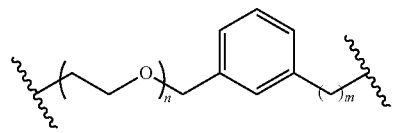
n = 1-8
m = 1-8
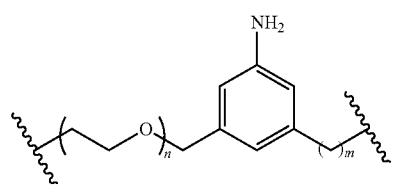
n = 1-8
m = 1-8
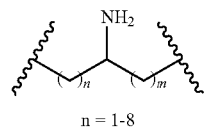
n = 1-8
m = 1-8
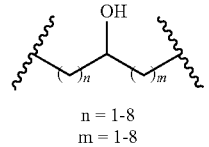
n = 1-8
m = 1-8
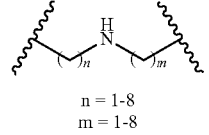
n = 1-8
m = 1-8
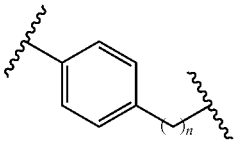
n = 1-8
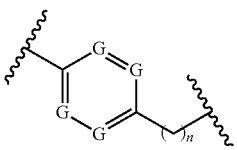
n = 1-8
G = N, CH
The C—C bond of the carbon bonded to C and Cl in Formula I can exist in R or S forms, or the composition can be part of a racemic mixture. In preferred embodiments, the IQB-CBI compound has the S,S configuration and, preferably, is stereoismetrically pure.

In another aspect provided herein is an antibody-drug conjugate having a structure of Formula II:

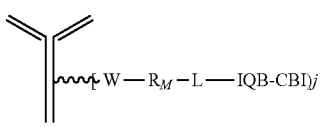

Formula II wherein:

is an antibody or antibody fragment;

W—$R_M$ is a linking moiety formed by W and $R_x$, wherein W is a moiety attached a natural or unnatural amino acid residue of the antibody/antibody fragment and $R_x$ is a succinimidyl, maleimidyl, cyclooctynyl, aminooxy, bisulfonyl, sulfonyl, or isothiocyanate moiety, such that W—$R_M$ is a disulfide, a thiolated succinimidyl, an amino substituted succinimidyl, a (cyclooctyl)-1, 4 triazolyl, oxime substituted N-glycan, oxime, a substituted bis-sulfopropyl, a sulfonamidyl, an amide, or a thiocarbamate moiety;

L is a linker;

IQB-CBI is a compound having a structure of Formula I:

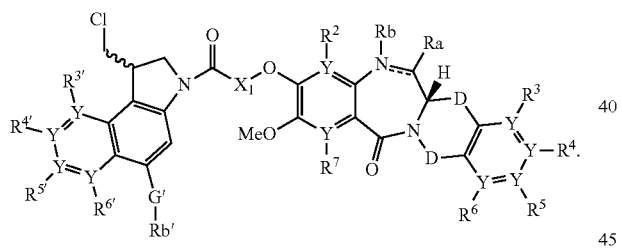

wherein:

the dotted bond shown between —C($R^a$)— and —N($R^b$)— is independently a single bond or a double bond;

when a double bond is present between —C($R^a$)— and —N($R^b$)—, the —C($R^a$)— is olefinic and has a substituent $R^a$, and $R^b$ of the —N($R^b$)— is not present;

when a single bond is present between —C($R^a$)— and —N($R^b$)—, the —C($R^a$)— is saturated and has a hydrogen substituent in addition to the $R^a$ substituent and $R^b$ of the —N($R^b$)— is present;

$R^a$ is independently H, or OH;

if present, $R^b$ is H, or -L-;

-L- is a linker L, where L is a bond or is a moiety having 1-200 nonhydrogen atoms selected from C, N, O, S, or halogen, and optionally incorporates ether, oxo, carboxamidyl, urethanyl, branched, cyclic, heterocyclic, aromatic or heteroaromatic moieties;

$R^2$ is selected from H, OH, $C_1$-$C_{10}$ alkyl, $C_2$-$C_{10}$ alkenyl or $C_2$-$C_{10}$ alkynyl;

$R^3$, $R^{3'}$, $R^4$, $R^{4'}$, $R^6$, and $R^{6'}$ are each independently selected from H, OH, $C_1$-$C_{10}$ alkyl, $C_2$-$C_{10}$ alkenyl or $C_2$-$C_{10}$ alkynyl, or, if Y is N, is not present;

each of $R^5$ or $R^{5'}$ is independently $NH_2$, $CO_2H$, H, OH, $C_1$-$C_{10}$ alkyl, $C_2$-$C_{10}$ alkenyl, $C_2$-$C_{10}$ alkynyl, -L-, -L-$R_x$ or -L-Sc, or, if Y is N, is not present;

$R^7$ is H;

G'-Rb' is selected from OH, O-L, O-L-R, O-L-Sc, $NH_2$, NH-L, NH-L-$R_x$, or NH-L-Sc;

each Y is, independently, N or C;

each D is, independently, $(CH_2)_n$ where n=0-4, provided that at least one D is $(CH_2)_n$ where n=1-4;

X1 is a spacer group selected from the following formulae:

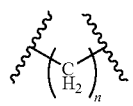

n = 1-8

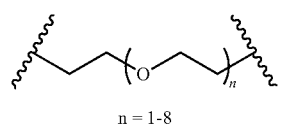

n = 1-8

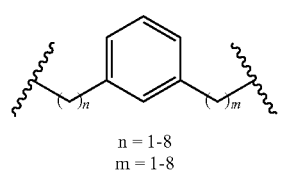

n = 1-8
m = 1-8

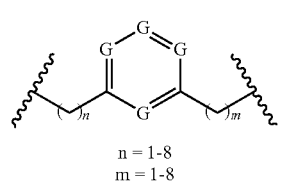

n = 1-8
m = 1-8
G = N, CH

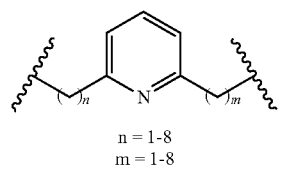

n = 1-8
m = 1-8

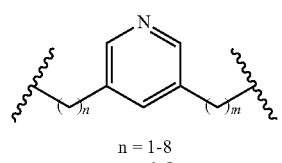

n = 1-8
m = 1-8

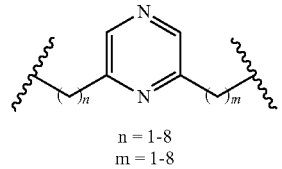

n = 1-8
m = 1-8 at least one of $R^b$, R5, R5' and $G'-R^{b'}$ comprises -L-.

In a preferred embodiment, the antibody-drug conjugate of Formula II has the following structure:

Formula II wherein:

is an antibody or antibody fragment;

W—$R_M$ is a linking moiety formed by W and $R_x$, wherein W is a moiety attached a natural or unnatural amino acid residue of the antibody/antibody fragment and $R_x$ is a succinimidyl, maleimidyl, cylooctynyl, aminooxy, bisulfonyl, sulfonyl, or isothiocyanate moiety, such that W—$R_M$ is a disulfide, a thiolated succinimidyl, an amino substituted succinimidyl, a (cyclooctyl)-1, 4 triazolyl, oxime substituted N-glycan, oxime, a substituted bis-sulfopropyl, a sulfonamidyl, an amide, or a thiocarbamate moiety;

L is a Linker L, wherein the Linker L is a bond or is a moiety having 1-200 nonhydrogen atoms selected from C, N, O, S, or halogen, and optionally incorporates ether, oxo, carboxamidyl, urethanyl, amino acid, heterocyclic, aromatic or heteroaromatic moieties;

IQB-CBI is a compound having a structure of Formula I:

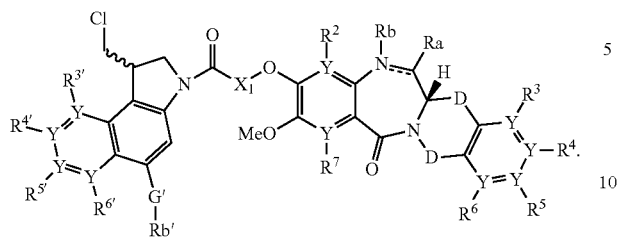

wherein:
- the dotted bond shown between —C(R$^a$)— and —N(R$^b$)— is independently a single bond or a double bond;
  - when a double bond is present between —C(R$^a$)— and —N(R$^b$)—, the —C(R$^a$)— is olefinic and has a substituent R$^a$, and R$^b$ of the —N(R$^b$)— is not present;
  - when a single bond is present between —C(R$^a$)— and —N(R$^b$)—, the —C(R$^a$)— is saturated and has a hydrogen substituent in addition to the R$^a$ substituent and R$^b$ of the —N(R$^b$)— is present;
- R$^a$ is independently H, or OH;
- if present, R$^b$ is H or is a bond to the Linker L;
- R$^2$ is selected from H, OH, C$_1$-C$_{10}$ alkyl, C$_2$-C$_{10}$ alkenyl or C$_2$-C$_{10}$ alkynyl;
- R$^3$, R$^{3'}$, R$^4$, R$^{4'}$, R$^{6'}$ and R$^6$ are each independently selected from H, OH, C$_1$-C$_{10}$ alkyl, C$_2$-C$_{10}$ alkenyl or C$_2$-C$_{10}$ alkynyl, or, if Y is N, is not present;
- each of R$^5$ or R$^{5'}$ is independently NH$_2$, CO$_2$H, H, OH, C$_1$-C$_{10}$ alkyl, C$_2$-C$_{10}$ alkenyl, C$_2$-C$_{10}$ alkynyl, is a bond to the Linker L, or, if Y is N, is not present;
- R$^7$ is H;
- G'-Rb' is selected from OH, O-L, NH$_2$, or NH-L, wherein L is the Linker L;
- each Y is, independently, N or C;
- each D is, independently, (CH$_2$)$_n$ where n=0-4, provided that at least one D is (CH$_2$)$_n$ where n=1-4;
- X1 is a spacer selected from the group consisting of the following:

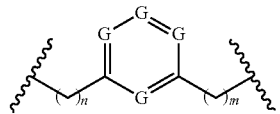

n = 1-8

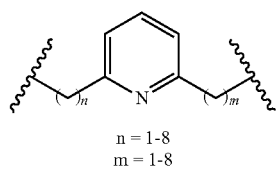

n = 1-8

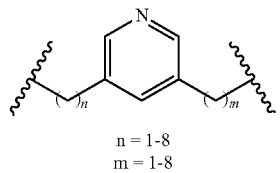

n = 1-8
m = 1-8

-continued

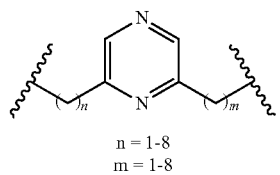

n = 1-8
m = 1-8
G = N, CH

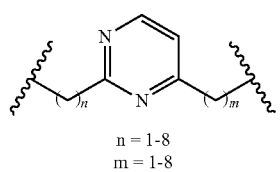

n = 1-8
m = 1-8

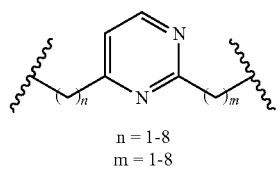

n = 1-8
m = 1-8

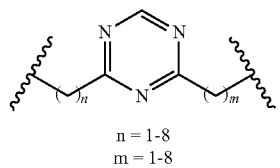

n = 1-8
m = 1-8

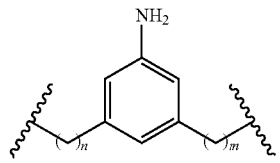

n = 1-8
m = 1-8

-continued n = 1-8
m = 1-8 n = 1-8
m = 1-8 n = 1-8
m = 1-8 n = 1-8
m = 1-8 n = 1-8
m = 1-8 n = 1-8
m = 1-8 n = 1-8 n = 1-8
G = N, CH wherein at least one $R^b$, $R^5$, $R^{5'}$ and G-$R^{b'}$ is a bond linked to Linder L or comprises Linker L.

In a preferred embodiment, the IQB-CBI compound of Formula I has S,S stereochemistry as follows:

wherein all of the substituents of the above IQB-CBI compound are as defined above. Similarly, in a preferred embodiment, the IQB-CBI portion of the antibody-drug conjugate of Formula II also has S,S stereochemistry.

DETAILED DESCRIPTION

I. Compounds

Figure 1:
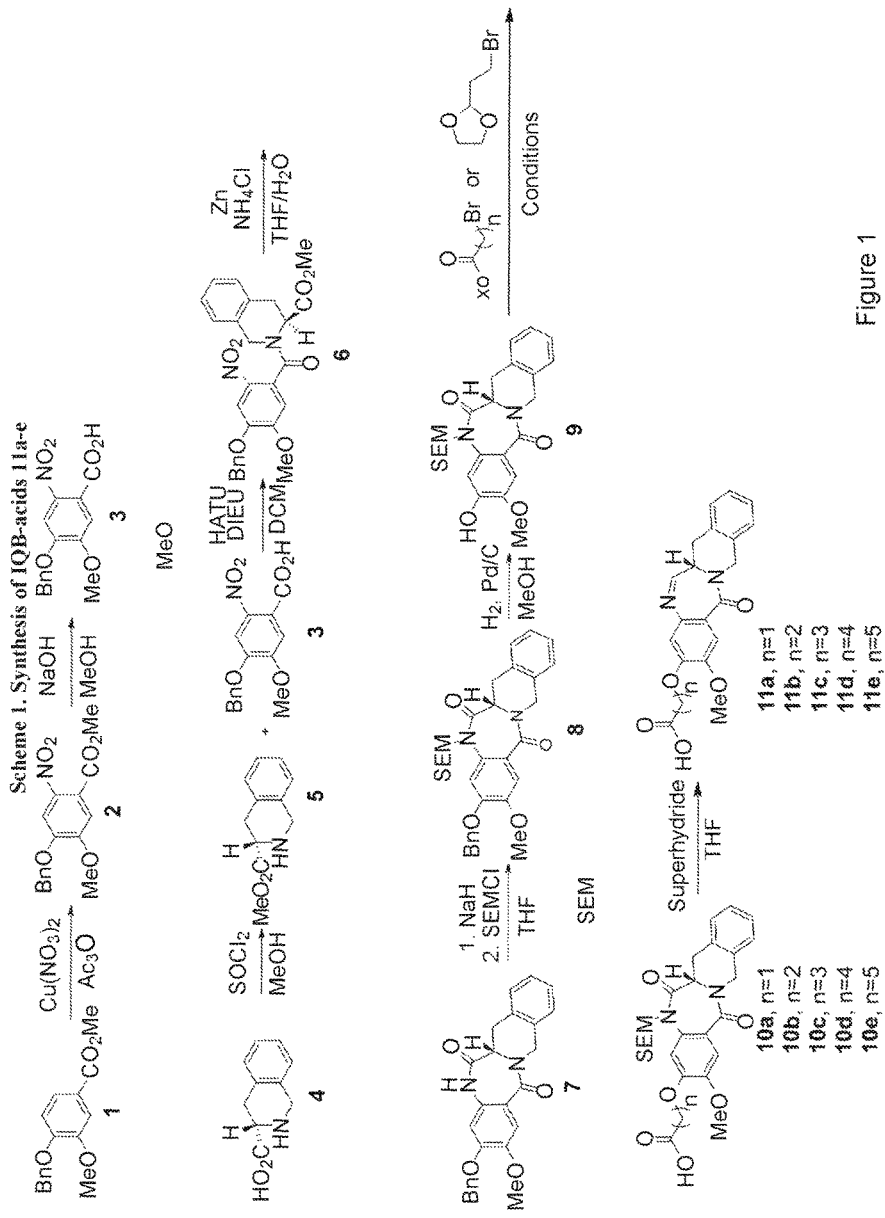
FIG. 1 shows the synthesis of IQB-acids 11a-e.

This disclosure provides isoquinolidinobenzodiazepine-1 (chloromethyl)-2,3-dihydro-1H-benzo[e]indole ("IQB-CBI") compounds of Formula I, antibody-drug conjugates of Formula II, and methods of using the compounds of Formula I and the antibody-drug conjugates of Formula II. In one aspect, the IQB-CBI compounds of Formula I having the following structure:

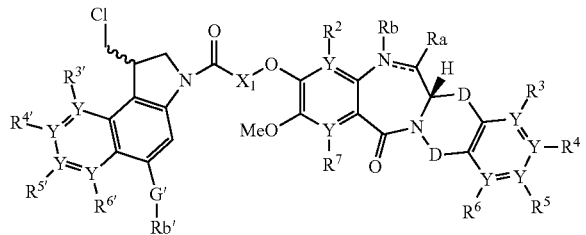

as described herein. In another aspect, the antibody-drug conjugates of Formula II have the following structure:

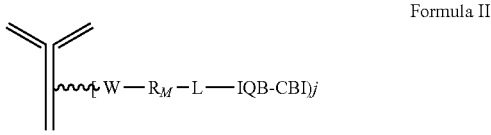

Formula II as described herein.

II. Definitions

As referred to herein, "alkyl" means a saturated, branched or straight-chain or cyclic, monovalent hydrocarbon radical having the stated number of carbon atoms (i.e., C1-C6 means one to six carbon atoms) that is derived by the removal of one hydrogen atom from a single carbon atom of a parent alkane. Typical alkyl groups include, but are not limited to, methyl; ethyl; propyls such as propan-1-yl, propan-2-yl, cyclopropan-1-yl; butyls such as butan-1-yl, butan-2-yl, 2-methyl-propan-1-yl, 2-methyl-propan-2-yl, cyclobutan-1-yl; and the like. In some embodiments, "alkyl" means a saturated, branched or straight-chain, monovalent hydrocarbon radical having the stated number of carbon atoms (i.e., C1-C6 means one to six carbon atoms) that is derived by the removal of one hydrogen atom from a single carbon atom of a parent alkane. Typical alkyl groups include, but are not limited to, methyl; ethyl; propyls such as propan-1-yl, propan-2-yl; butyls such as butan-1-yl, butan-2-yl, 2-methyl-propan-1-yl, 2-methyl-propan-2-yl; and the like.

As referred to herein, "alkenyl" means an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. As used herein, "lower alkenyl" means (C2-C8) alkenyl. In some embodiments, "alkenyl" means an unsaturated branched, straight-chain alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1l-en-1-yl, prop-1-en-2-yl, prop-2-en-1-yl, prop-2-en-2-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, etc.; and the like. As used herein, "lower alkenyl" means (C2-C8) alkenyl.

As referred to herein, "alkynyl" means an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8) alkynyl. In some embodiments, "alkynyl" means an unsaturated branched, straight-chain alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8) alkynyl.

Cyclic alkyl, alkenyl and alkynyl groups are also defined by the term "cycloalkyl" which means a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

As referred to herein, "alkylene" means a divalent alkyl moiety.

As referred to herein, "alkoxy" means an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described herein. Alkoxy groups can be substituted or unsubstituted.

As referred to herein, "halide" means fluoro, chloro, bromo, or iodo.

As referred to herein, "carboxamide" means a monovalent moiety having the formula —C(=O)NH$_2$. In some embodiments, one or both of the amide hydrogens may be replaced by substituents other than hydrogen.

As referred to herein "carboxamidyl" means a divalent moiety having the formula —C(=O)N(H)—. In some embodiments the amide hydrogen may be replaced by other substituents.

As referred to herein, "oxo" means a moiety having a formula

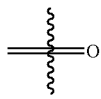

which is attached to a carbon.

As referred to herein, "carboxyl" means a moiety having a formula —C(O)OH or —C(O)O$^-$.

As referred to herein, "heteroalkyl" means an alkyl group of any suitable length and having from 1 to 3 heteroatoms such as N, O, and S. Additional heteroatoms can also be useful, including, but not limited to, B, Al, Si, and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

As referred to herein, "heterocyclic" or "heterocyclyl" means a moiety that is a saturated or partially unsaturated, non-aromatic mono or multicyclic alkyl cyclic moiety having heteroatom substitution replacing ring carbons. Heterocyclic rings of the present invention can contain 3 to 20 ring atoms, where from 1 to 5 or more of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heterocyclic groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclic groups, such as 1, 2, 3, 4, or 5, or 1 to 2, 1 to 3, 1 to 4, 1 to 5, 2 to 3, 2 to 4, 2 to 5, 3 to 4, or 3 to 5. Heterocyclic groups can have from 3 to 8 ring members and from 1 to 4 heteroatoms, or from 3 to 8 ring members and from 1 to 3 heteroatoms, or from 3 to 6 ring members and from 1 to 4 heteroatoms, or from 3 to 6 ring members and from 1 to 3 heteroatoms. Multicyclic heterocyclic moieties may have fused rings. Typical heterocyclic groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

As referred to herein, "aromatic" or "aryl" means a monovalent aromatic hydrocarbon group having the stated number of carbon atoms (i.e., C6-C14 means from 6 to 14 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. Specific exemplary aryls include phenyl and naphthyl.

As referred to herein, "heteroaromatic" or "heteroaryl" means a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 5 to 6, 5 to 8, 6 to 8, 5 to 9, 5 to 10, 5 to 11, or 5 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

As referred to herein, "$C_1$-$C_{12}$" means the range of number of carbon atoms included in the group described. For example, a $C_1$-$C_{12}$ alkyl has from one carbon to 12 carbon atoms, and may be any one of 1, 2, 3, 4, 5, 6, 7, 8, 9, 10, 11, or 12 carbons. A $C_1$ alkyl is methyl, a $C_2$ alkyl is ethyl and so on. References to $C_1$-$C_{10}$ means one to ten carbons, $C_1$-$C_6$ means one to six carbons, $C_1$-$C_3$ means one to three carbons, and etc.

As referred to herein, "substituted" means a moiety having a hydrogen radical removed, and another non-hydrogen substituent replacing it. More than one substituent may be incorporated in any moiety, as long as the rule of chemical valency is observed. Substituents suitable for use in alkyl, alkenyl, alkynyl, aromatic or heterocyclic groups include, but are not limited to, the following substituents: —OH, —OR, —NH$_2$, —NHR, —NR$_2$, —CO$_2$H, —CO$_2$R, —C(O)NH$_2$, —C(O)NHR, —C(O)NR$_2$, halide, oxo, and R, where R is a $C_1$-$C_6$ alkyl.

As referred to herein, a squiggly bond ($\sim$) denotes a stereocenter of the compounds of the present invention. It will be understood by those of skill in the art that that bond will determine the chiral configuration of the molecule (R or S and eventually dextro- or laevorotary effects). Hashed and wedged bonds are used to denote specific chiral configurations. The IQB-CBI compounds of the present invention, as well as the antibody-drug conjugates that incorporate such IQB-CBI compounds, can have, for example, the following stereochemistries: S,S; R,R; S,R and R,S. In the IQB-CBI compounds of Formula I, as well as in the antibody-drug conjugates that incorporate the IQB-CBI compounds of Formula II, the S,S stereochemistry is preferred, and it is further preferred that the IQB-CBI compound of Formula I is stereoisomerically or enantiomerically pure (at least 80% enantiomerically pure, at least 85% enantiomerically pure, at least 90% enantiomerically pure, at least 95% enantiomerically pure, at least 97% enantiomerically pure, at least 100% enantiomerically pure).

As referred to herein, the term "nucleic acid", refers to a linear polymer of nucleosides (including deoxyribonucleosides, ribonucleosides, or analogs thereof) joined by internucleosidic linkages. Nucleic acid may encompass the term "polynucleotide" as well as "oligonucleotide". The linear polymer may be represented by a sequence of letters, such as "ATGCCTG," where it will be understood that the nucleotides are in 5' to 3' order from left to right, and that "A" denotes deoxyadenosine, "C" denotes deoxycytidine, "G" denotes deoxyguanosine, and "T" denotes deoxythymidine, unless otherwise noted. Another natural nucleotide is "U", denoting uridine. The letters A, C, G, T and U can be used to refer to the bases themselves, to nucleosides, or to nucleotides comprising the bases, as is standard in the art. In naturally occurring nucleic acids, the inter-nucleoside linkage is typically a phosphodiester bond, and the subunits are referred to as "nucleotides." Nucleic acids may also include other inter-nucleoside linkages, such as phosphorothioate linkages, and the like. Such analogs of nucleotides that do not include a phosphate group are considered to fall within the scope of the term "nucleotide" as used herein, and nucleic acids comprising one or more inter-nucleoside linkages that are not phosphodiester linkages are still referred to as "polynucleotides", "oligonucleotides", etc.

The term "amino acid" refers to both the twenty "canonical" or "natural" amino acids, as well "non-canonical" amino acids, also referred to as "unnatural" amino acids, such as modified or synthetic amino acids, as well as amino acid analogs and amino acid mimetics that function similarly to naturally occurring amino acids. Naturally occurring amino acids are those encoded by the genetic code. Modified amino acids include, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Linker L is a bond or is a moiety having 1-200 nonhydrogen atoms selected from C, N, O, S, or halogen, and optionally incorporates ether, oxo, carboxyl, carboxamide, carboxamidyl, urethanyl, branched, cyclic, unsaturated, amino acid, heterocyclic, aromatic or heteroaromatic moieties. Linker L may be unbranched or branched, flexible or rigid, short or long and may incorporate any combination of moieties as deemed useful. In some embodiments, at least a portion of the linker L may have a polyalkylene oxide polymeric region, which may enhance solubility of the compound of Formula I or II. In some embodiments, the linker L may have a repeating unit of ethylene glycol, and may have a number of repeating ethylene glycol units of about 1 to about 25, or any number therebetween. In some embodiments, L may include about 3 to about 20, about 4 to about 15, about 5 to about 12 or about 6 to about 10 ethylene glycol units. In some embodiments, at least a portion of Linker L may include one or more amino acid moieties which may provide enhanced solubility for the compound of Formula I or II or may provide amino acid sequences to enhance target binding, enhance compatibility with a target binding agent, or enhance target binding recognition. In other embodiments, the linker L may include one or more amino acid moieties that provide a suitable substrate motif for a protease. When a set of amino acid moieties are incorporated into the linker L that provide a substrate motif specific for a selected protease, the cytotoxic drug compound of Formula I or II may be released from a target bound conjugate to provide localized cytotoxic effects. Such substrate motifs are known in the art and may be incorporated into the linker L as desired to provide selective release from the target bound conjugate. This selectivity can be based on known presence of a desired protease within the localized delivery region of the conjugate drug. Other polymeric types of moieties may be incorporated in the linker L, such as polyacids, polysaccharides, or polyamines. Other moieties such as substituted aromatic or heteroaromatic moieties may be used to enhance rigidity or provide synthetically accessible sites on substituents therein for linking to reactive moieties or to the compound of Formula I or II.

The linker L can include a variety of groups or moieties. For example, the linker L can include a spacer (—$Y_L$—), an amino acid sequence ($X_{AA}$), and a polyethyleneglycol (PEG or —$CH_2CH_2O$—) moiety. A representative linker can have the following structure:

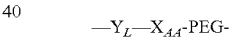

The Amino Acid unit (—$X_{AA}$—), when present, links the PEG unit, if present, or reactive moiety to the Spacer unit if the Spacer unit is present. $X_{AA}$ is a dipeptide, tripeptide, tetrapeptide, pentapeptide, hexapeptide, heptapeptide, octapeptide, nonapeptide, decapeptide, undecapeptide or dodecapeptide unit. Each amino acid of the $X_{AA}$ group can be arginine, histidine, lysine, aspartic acid, glutamic acid, serine, threonine, asparagine, glutamine, cysteine, selenocysetein, glycine, proline, alanine, valine, isoleucine, leucine, methionine, phenylalanine, tyrosine, tryptophan, or citrulline (Cit). The $X_{AA}$ unit of the compounds of the invention can be enzymatically cleaved by one or more enzymes, including a tumor-associated protease, to liberate the IQB-CBI unit. Preferred $X_{AA}$ units include, but are not limited to, Ala-Val, Val-Ala, and Val-Cit.

The spacer —$Y_L$—, when present, links an Amino Acid unit to the IQB unit when an Amino Acid unit is present. Spacer units are of two general types: self-immolative and non-self-immolative. A non self-immolative Spacer unit is one in which part or all of the Spacer unit remains bound to the IQB unit after cleavage, particularly enzymatic, of an Amino Acid unit from the Antibody-Drug Conjugate (ADC). Examples of a non self-immolative Spacer unit include, but are not limited to a (glycine-glycine) Spacer unit and a glycine Spacer unit. When a compound of the invention containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from L-A$_a$-Ww-. In one embodiment, an independent hydrolysis reaction takes place within the target cell, cleaving the glycine-Drug unit bond and liberating the Drug.

In a preferred embodiment, —Y$_L$— is a p-aminobenzyl alcohol (PAB) unit:

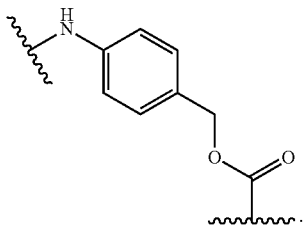 [SMILES: *Nc1ccc(COC(*)=O)cc1]

In one embodiment, a non self-immolative Spacer unit (—Y$_L$—) is -Gly-Gly-.

In another embodiment, a non self-immolative the Spacer unit (—Y$_L$—) is -Gly-.

In one embodiment, the invention provides a compound in which the Spacer unit is absent, or a pharmaceutically acceptable salt or solvate thereof.

Alternatively, a compound of the invention containing a self-immolative Spacer unit can release IQB or the CBI unit without the need for a separate hydrolysis step. In this embodiment, —Y$_L$— is a PAB group that is linked to —X$_{AA}$— via the amino nitrogen atom of the PAB group, and connected directly to either the IQB or the CBI unit via a carbonate, carbamate or ether group.

In some embodiments, -L-R$_x$ has the structure:

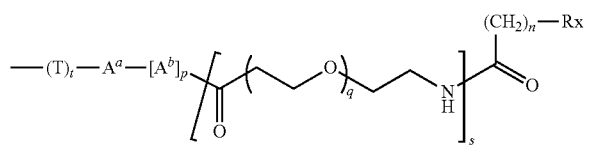

wherein:

T is a self-immolating group, such as those described above as well as a p-aminobenzyl oxycarbonyl group or a p-aminobenzyl alcohol (PAB) unit;

t is 0 or 1;

A and each A$^b$ are independently selected from the group consisting of alanine, l-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

q is 1, 2, 3, 4, 5, 6, 7, 8, 9, 10, 11, or 12;

n is 1, 2, 3, 4, or 5;

s is 0 or 1;

Rx is

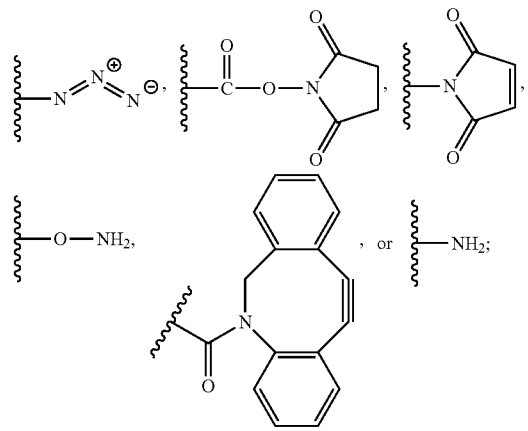

the wavy line indicates the position, i.e., point, of attachment.

Other examples of self-immolative spacers include, but are not limited to, aromatic compounds that are electronically similar to the PAB group such as 2-aminoimidazol-5-methanol derivatives (see Hay et al., *Bioorg. Med Chem. Lett.*, 1999, 9, 2237) and ortho or para-aminobenzylacetals. Spacers can be used that undergo cyclization upon amide bond hydrolysis, such as substituted and unsubstituted 4-aminobutyric acid amides (Rodrigues et al., *Chemistry Biology*, 1995, 2, 223), appropriately substituted bicyclo[2.2.1] and bicyclo[2.2.2] ring systems (Storm, et al., *J. Amer. Chem. Soc.*, 1972, 94, 5815) and 2-aminophenylpropionic acid amides (Amsberry, et al., *J. Org. Chem.*, 1990, 55, 5867). Elimination of amine-containing drugs that are substituted at the a-position of glycine (Kingsbury, et al., *J. Med Chem.*, 1984, 27, 1447) are also examples of self-immolative spacer useful in the Compounds of the Invention.

Preferred Spacer units (—Y$_L$—) can be:

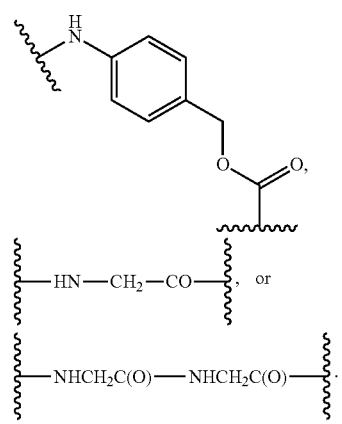

For example, the linker L can include ethylene glycol repeating units, and an amino acid sequence. In some embodiments, linker L includes the formula:

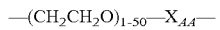

wherein X$_{AA}$ is an amino acid sequence.

Any suitable number of ethylene glycol units can be used in the linker L of the present invention. For example, the linker L can include 1, 2, 3, 4, 5, 6, 7, 8, 9, 10, 11, 12, 15, 16, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 or more ethylene glycol units (inclusive of all ranges within the 1 to 40 ethylene glycol units, including the lower and upper limits). For instance, the linker L can include 1 to 25 ethylene glycol units, preferably 2 to 20 ethylene glycol units, more preferably 2 to 15, even more preferably 5 to 15 ethylene glycol units. In some embodiments, the linker L can include 8 ethylene glycol units. Several commercially available ethylene glycol groups (polyethylene glycol, PEG) are suitable in the linker L, such as $H_2N$-dPEG®$_8$-C(O)OH, having a discrete ("d") polyethylene glycol having 8 ethylene glycol repeating units. Other discrete PEG units are commercially available and known to one of skill in the art, such as by Advanced ChemTech. One of skill in the art recognizes that $H_2N$-dPEG®$_8$-C(O)OH has the following formula:

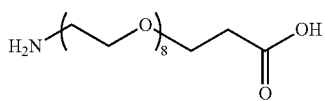

Accordingly, when $H_2N$-dPEG®$_8$-C(O)OH is incorporated into the linker L of the present invention, it can be written as —HN-dPEG$_8$-C(O)— or —HN-dPEG$_8$-CH$_2$CH$_2$—C(O)—.

In some embodiments, the linker L includes the formula:

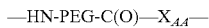

wherein PEG has 1-50 ethylene glycol units, and $X_{AA}$ is an amino acid sequence.

In some embodiments, the linker L includes the formula:

wherein PEG has 1-50 ethylene glycol units, and XAA is an amino acid sequence.

The amino acid portion of the linker L can include any suitable number of amino acid moieties, as described above. For example, the amino acid sequence XAA can include from 1 to 100 amino acid moieties, or from 1 to 10 amino acid moieties, or from 1 to 5 amino acid moieties. The linker L can include 1, 2, 3, 4, 5, 6, 7, 8, 9, 10, or more amino acid moieties. In some embodiments, the linker L includes 2 amino acid moieties. In some embodiments, the linker L includes the amino acid sequence Val-Ala. In some embodiments, the linker L includes the formula:

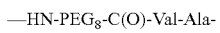

wherein PEG$_8$ has 8 ethylene glycol units.

In some embodiments, the linker L includes the formula:

wherein PEG$_8$ has 8 ethylene glycol units.

The linker L can also include a variety of other connecting groups that connect the ethylene glycol portion to the amino acid sequence, or connect the ethylene glycol or amino acid sequence to the reactive moiety $R_x$, substance $S_c$, or the compound of Formula I and II. For example, the amino acid sequence can be connected to the compound of Formula I and II via a 4-amino benzyl carboxylate group. In some embodiments, the ethylene glycol portion can be directly linked to the reactive moiety $R_x$ or the substance $S_c$. In some embodiments, the linker L has the formula:

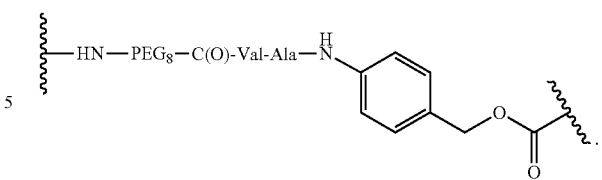

The linker L can also include a variety of other connecting groups that connect the ethylene glycol portion to the amino acid sequence, or connect the ethylene glycol or amino acid sequence to the reactive moiety $R_x$, substance $S_c$, or the compound of Formula I and II. For example, the amino acid sequence can be connected to the compound of Formula I and II via a 4-amino benzyl carboxylate group. In some embodiments, the ethylene glycol portion can be directly linked to the reactive moiety $R_x$ or the substance $S_c$. In some embodiments, the linker L has the formula:

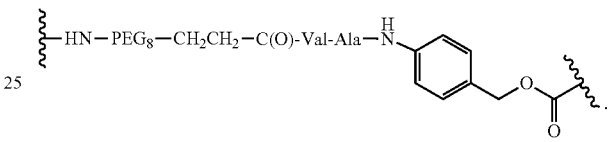

$R_x$ is a reactive moiety. $R_x$ may be any suitable reactive moiety as long as it is capable of reacting with a correspondingly reactive moiety present on the substance Sc, which may be a target binding agent as described herein. In various embodiments, Sc is a protein or a portion of a protein, and has accessible conjugatable moieties such as:

Thiols/disulfides. Reactive moieties $R_x$ that can react with thiols or disulfides include maleimide, iodoacetamide, azide, thiazole and pyrridopyridazine. Disulfides may also be labeled by use of a bisulfone reactive moiety. Additionally maleimide reactive moieties can react with engineered selenocysteine moieties.

Amines. Reactive moieties $R_x$ that may be used to couple the IQB or the CBI units of the IQB-CBI compounds to a target binding agent Sc include isothiocyanate, succinimidyl ester, sulfonyl halide, carboxylic acids (in the presence of carbodiimide coupling reagents), sulfosuccinimidyl ester, 4-sulfotetrafluorophenyl ester, tetrafluorophenyl ester, and sulfodichlorophenol ester. This list is in no way limiting and other reactive moieties $R_x$ that are capable of reacting with an amine of a target binding agent $S_c$ may be used.

Aldehydes/ketones. These moieties may be introduced into a target binding agent Sc and subsequently reacted with a compound of Formula I and II having a -L-Rx where the reactive moiety Rx is hydrazine, semihydrazide, carbohydrazide, or hydroxylamine. This list is in no way limiting and other reactive moieties $R_x$ that are capable of reacting with an aldehyde of a target binding agent $S_c$ may be used.

Other reactive moieties $R_x$ that are useful in the compounds of Formula I and II include azides, phosphines, or alkynes which can be used in Staudinger reactions, Pictet-Spengler reactions and/or Click-type chemistry (Copper containing or not) for selectively labeling of proteins including antibodies and their fragments. This is a non-limiting list of reactive moieties $R_x$ useful for reacting with engineered sites on target binding agents $S_c$.

In some embodiments, $R_x$ may be maleimide, bis-sulfone, iodoacetamide, azide, isothiocyanate, succinimidyl ester, sulfonyl halide, carboxylic acids, semihydrazide, carbohydrazide, hydroxylamine, phosphine, or alkyne.

-L-$R_x$ is a linker L attached to a reactive moiety $R_x$. -L-$R_x$ may be used in a compound of Formula I or II to form a reagent bearing IQB-CBI compounds that can attach to a substance $S_c$, which may be a target binding agent as described herein. Any combination of linker L and reactive moiety $R_x$ described herein may be used in the compounds of Formula I or II. See FIG. 7 for some exemplary -L-$R_x$.

A number of other chemistries are known for attachment of compounds to antibodies. U.S. Pat. No. 7,595,292 (Brocchini et al.) refers to linkers that form thioesters with the sulfurs in a disulfide bond of an antibody. U.S. Pat. No. 7,985,783 (Carico et al.) refers to the introduction of aldehyde residues into antibodies, which are used to couple compounds to the antibody.

$S_c$ is a target binding agent selected from a protein, a portion of a protein, a peptide, or a nucleic acid. In some embodiments, a target-binding agent that is a protein may include an antibody, an antibody fragment, or an antibody single-chain fragment variable ("scFV"). The target-binding agent may bind to a tumor-associated antigen, a cancer-stem-cell associated antigen or a viral antigen.

In various embodiments, the target-binding agent $S_c$ may bind to a target selected from an acute myeloid leukemia (AML 4) cell, an acute promyelocytic leukemia cell, an acute lymphoblastic leukemia cell, an acute lymphocytic leukemia cell, a chronic lymphocytic leukemia cell, a chronic myeloid leukemia cell, a chronic T-cell lymphocytic leukemia, a myelodysplastic syndromic cell, a multiple myeloma cell, a prostate carcinoma cell, a renal cell adenocarcinoma cell, a pancreatic adenocarcinoma cell, a lung carcinoma cell or a gastric adenocarcinoma cell, a gastric adenocarcinoma cell, a breast cancer cell, a colon cancer cell, a melanoma cell, a thyroid cancer cell, an ovarian cancer cell, a bladder cancer cell, a liver cancer cell, a head and neck cancer cell, an esophageal cancer cell, a hodgkin lymphoma cell, a non-hodgkin lymphoma cell, a mesothelioma cell, a neuroblastoma cell, a neuroendocrine tumor cell, a neurofibromatosis type 1 (NF1) cell, a neurofibromatosis type 2 (NF2) or an osteosarcoma cell.

In some other embodiments, the target-binding agent $S_c$ may bind a target selected from CLL-1, IL1RAP, TIM-3, CD19, CD20, CD22, ROR1, mesothelin, CD33, CD123/IL3Ra, GPR114, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmel-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor-α, CD138, CEACAM5, CD56, CD70, CD74, GCC, 5T4, CD79b, Steap1, Napi2b, Lewis Y Antigen, LIV, c-RET, DLL3, EFNA4, Endosialin/CD248.

In yet other embodiments, the target-binding agent $S_c$ may be a bi-specific antibody/antibody fragment. In some embodiments, the bi-specific antibody/antibody fragment binds to one or two targets selected from CLL-1, IL1RAP, TIM-3, CD19, CD20, CD22, ROR1, mesothelin, CD33, CD123/IL3Ra, GPR114, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmel-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor, CD138, CEACAM5, CD56, CD70, CD74, GCC, 5T4, CD79b, Steap1, Napi2b, Lewis Y Antigen, LIV, c-RET, DLL3, EFNA4, Endosialin/CD248, Ly6e (RIG-e), CD79a, CD274 (PD-L1), CD38, DLL4, CD319 (SLAM7).

III. Conjugates

Target binding moieties can be attached to an IQB-CBI compound of this disclosure using a variety of known cross-linking agents. Methods for covalent or non-covalent attachment of moieties to polypeptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. Nos. 5,603,872 and 5,401,511. Non-limiting examples of cross-linking reagents include glutaraldehyde, bifunctional oxirane, ethylene glycol diglycidyl ether, carbodiimides such as 1-ethyl-3-(3-dimethylaminopropyl) carbodiimide or dicyclohexylcarbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide.

In some embodiments, the target binding moiety comprises an antibody. The term "antibody" refers to a polypeptide comprising a framework region from an immunoglobulin gene, or fragments thereof ("antibody fragment"), that specifically bind and recognize an antigen. Typically, the "variable region" contains the antigen-binding region of the antibody (or its functional equivalent) and is most critical in specificity and affinity of binding. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD).

An "isotype" is a class of antibodies defined by the heavy chain constant region. Light chains are classified as either kappa or lambda. Heavy chains are classified as gamma, mu, alpha, delta, or epsilon, which in turn define the isotype classes, IgG, IgM, IgA, IgD and IgE, respectively. Antibodies can exist as intact immunoglobulins or as any of a number of well-characterized fragments that include specific antigen-binding activity, e.g., F(ab)'2, or an Fab' monomer.

A "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities. A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

A "humanized antibody" refers to an immunoglobulin molecule antibodies in which the antigen binding loops, i.e., CDRs, obtained from the VH and Vt. regions of a non-human antibody are grafted to a human framework sequence. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., *Nature* 332:323-327 (1988); Marks et al., *Bio/Technology* 10:779-783 (1992); Morrison, *Nature* 368:812-13 (1994); Fishwild et al., *Nature Biotechnology* 14:845-51 (1996). Transgenic mice, or other organisms such as other mammals, may also be used to express humanized or human antibodies, as disclosed in U.S. Pat. No. 6,673,986.

The term "cysteine substituted antibody," as used herein, refers to an antibody comprising at least one non-naturally occurring constant region immunoglobulin amino acid residue that has been substituted with cysteine. A non-naturally occurring substitution is one that is not isotypic. In one embodiment, the substituted residues are heavy chain constant regions. Non-limiting examples of cysteine substituted antibodies include the substitutions S156C and S239C.

The terms "antigen", "antibody target", and like terms refer to a molecule, compound, or complex that is recognized by an antibody, i.e. can be specifically bound by the antibody. The antibody binds to an "epitope" on the antigen.

The terms "specific for," "specifically binds," and like terms refer to a molecule (e.g., antibody or antibody fragment) that binds to a target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a primary antibody will typically bind the primary antibody with at least a 2-fold greater affinity than a non-primary antibody target (e.g., an antibody from a different species or of a different isotype, or a non-antibody target).

The term "captures" with respect to an antibody target (e.g., antigen, analyte, immune complex), typically indicates that an antibody binds a majority of the antibody targets in a pure population (assuming appropriate molar ratios). For example, an antibody that binds a given antibody target typically binds to at least 2/3 of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

Antibodies or fragments thereof may have functional groups which may be attractive targets for conjugation by compounds of Formula I or II having a -L-$R_x$, as described above. A compound incorporating -L-$R_x$ where maleimide is the reactive moiety may react with thiols of cysteine residues or disulfides formed from two cysteine side chains, where accessible on the antibody or fragment thereof. Alternatively, azido or iodoacetamidyl reactive moieties attached to a linker of the compound of Formula I or II can also form a conjugate with a thiol of cysteine residues or disulfides formed intramolecularly. Disulfides can be specifically targeted by use of a compound of Formula I or II having -L-$R_x$ where the reactive moiety is a bis-sulfone, which can attach to both side chains at once.

Lysine side chains of antibodies or fragments thereof can be conjugated with a compound of Formula I or II having a -L-$R_x$ where the reactive moiety is selected but not limited to isothiocyanate, succinimidyl ester, sulfonyl halide, carboxylic acid, sulfosuccinimidyl ester, 4-sulfotetrafluorophenyl ester, tetrafluorophenyl ester, and sulfodichlorophenol ester. When a carboxylic acid is the reactive moiety, the attachment reaction to the lysine side chain amino moiety is performed in the presence of a coupling reagent such as carbodiimide, which activates the carboxylic acid in situ.

Glutamine side chains may be targeted by an IQB-CBI having -L-$R_x$ where the reactive moiety is an aminoalkyl moiety. The amino moiety can be a substrate for modified transglutaminase to provide a glutaminyl conjugated IQB-CBI.

Aldehydes or ketones may be produced on a target binding agent such as an antibody or a fragment thereof, by oxidative treatments, often of the glycan portion of the antibody. Periodate or other oxidizing agents can be used to produce these carbonyl containing sites which may be targeted by a IQB-CBI compound of Formula I having a -L-Rx, where the reactive moiety is hydrazine, semihydrazide, carbohydrazide, or hydroxylamine.

Engineered functional moieties on the target binding agent, such as an antibody or fragment thereof, may also be conjugated by the compounds of Formula of I or II having a -L-$R_x$. Selenocysteine may be incorporated ribosomally in engineered antibody fragments, which may afford a highly discriminating conjugation reaction with either an IQB or CBI unit having a maleimide reactive moiety.

Azido or cyclooctyne moieties may be engineered into a target binding agent which can then permit the opposite reactive moiety, cyclooctynyl or azidyl reactive groups of an IQB having a -L-$R_x$, using copper-free click chemistry.

Introduction of unnatural amino acids via ribosomal incorporation can introduce a para-acetyl phenylalanine into a target binding agent. The acetyl group can be conjugated with an IQB or a CBI having a -L-Rx where the reactive moiety is an aminooxy reactive group, providing an oxime conjugation product of the target binding agent. Another unnatural amino acid introduced via this process, can provide an azidyl-derivative of lysine which can be reacted with an IQB or a CBI having a -L-$R_x$ where the reactive moiety is a cyclooctyne, and copper-free click chemistry is used.

These examples are in no way limiting; many other approaches to defined conjugation of a target binding agent such as an antibody or fragment thereof are envisioned by the use of the IQB-CBI compounds of Formula I having -L-$R_x$ to form conjugates of formula having -L-$S_c$.

In some embodiments, an antibody-drug conjugate may have a structure of Formula II as defined herein.

IV. Pharmaceutical Compositions

Dosage forms containing compounds of the present invention as the active ingredient may be advantageously used to treat or prevent proliferative diseases. The dosage forms may be administered or applied singly, or in combination with other agents. The formulations may also deliver a compound of the present invention to a subject in combination with another pharmaceutically active agent, including another compounds.

The formulations, for human medical use, of the present disclosure comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The terms "effective amount," "effective dose," "therapeutically effective amount," etc. refer to that amount of the therapeutic agent sufficient to ameliorate a disorder, as described herein. For example, for the given parameter, a therapeutically effective amount will show an increase or decrease of therapeutic effect of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosage forms can be prepared for mucosal (e.g., nasal, sublingual, vaginal, buccal, or rectal), parenteral (e.g., subcutaneous, intravenous, intramuscular, or intraarterial injection, either bolus or infusion), oral, or transdermal administration to a subject. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil-in-water emulsions, or a water-in-oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

Injectable (e.g., intravenous) compositions can comprise a solution of the IQB-CBI compounds or the antibody-drug conjugates of the present invention suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the composition can be formulated in a kit for intravenous administration.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of the IQB-CBI compounds or the antibody-drug conjugates of the present invention can be presented in unit-dose or multi-dose sealed containers, such as ampoules and vials.

The pharmacologically active compounds of the disclosure are useful in the manufacture of pharmaceutical compositions comprising an effective amount thereof in conjunction or admixture with the excipients or carriers suitable for either enteral or parenteral application. Preferred are tablets and gelatin capsules comprising the active ingredient together with one or more of the following: (a) diluents, such as lactose, dextrose, sucrose, mannitol, sorbitol, cellulose, glycine and the like; (b) lubricants, such as silica, talcum, stearic acid, its magnesium or calcium salt, polyethyleneglycol and the like; for tablets also; (c) binders, such as magnesium aluminum silicate, starch paste, gelatin, tragacanth, methylcellulose, sodium carboxymethyl-cellulose or polyvinylpyrrolidone and the like; and, if desired, (d) disintegrants, such as effervescent mixtures and the like; and (e) absorbents, colorants, flavors, and sweeteners and the like.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Said pharmaceutical compositions may be sterilized and/or contain adjuvants, such as preserving, stabilizing, wetting or emulsifying agents, solution promoters, salts for regulating the osmotic pressure, and/or buffers. In addition, they may also contain other therapeutically valuable substances. Said compositions are prepared according to conventional mixing, granulating, or coating methods, respectively, and contain about 0.1 to 75%, preferably about 1 to 50%, of the active ingredient.

The concentration of the active agent in the formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the subject and physician. The formulations will typically contain on the order of about 0.5 wt % to 50 wt % active agent, preferably about 0.5 wt % to 5 wt % active agent, optimally about 5 wt % to 20 wt % active agent.

An IQB-CBI compound or an IQB-CBI antibody-drug conjugate of the present invention can also be formulated to provide more than one active compound, e.g., additional chemotherapeutic or cytotoxic agents, cytokines, or growth inhibitory agents. The active ingredients may also be prepared as sustained-release preparations (e.g., semi-permeable matrices of solid hydrophobic polymers (e.g., polyesters, hydrogels (for example, poly (2-hydroxyethyl-methacrylate), or poly (vinylalcohol)) or polylactides). The antibodies and immuncongugates can be entrapped in a nanoparticle prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

IQB-CBIs or IQB-CBI antibody-drug conjugates of this disclosure may take the form of a pharmaceutically acceptable salt, e.g., a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, butyric acid, propionic acid, hexanoic acid, cyclopentanepropionic acid, glycolic acid, pyruvic acid, lactic acid, valeric acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like, made by conventional chemical means; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like, made by conventional chemical means.

V. Methods of Use

A. Treatment of Proliferative Disease

Compounds of this disclosure inhibit cell growth (proliferation), and thus are useful in pharmaceutical compositions to treat a subject, e.g., a vertebrate, e.g., a mammal, e.g., a human. IQB-CBIs can be administered alone or as antibody-drug conjugates wherein they are conjugated to a cell targeting agent such as an antibody.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically "patient" refers to an individual under medical supervision. A patient can be an individual that is seeking treatment, monitoring, adjustment or modification of an existing therapeutic regimen, etc. A "cancer patient" can refer to an individual that has been diagnosed with cancer, is currently following a therapeutic regimen, or is at risk of recurrence, e.g., after surgery to remove a tumor. In some embodiments, the cancer patient has been diagnosed with cancer and is a candidate for therapy. Cancer patients can include individuals that have not received treatment, are currently receiving treatment, have had surgery, and those that have discontinued treatment.

The terms "therapy," "treatment," and "amelioration" refer to any reduction in the severity of symptoms. In the case of treating cancer, treatment can refer to, e.g., reducing tumor size, number of cancer cells, growth rate, metastatic activity, reducing cell death of non-cancer cells, reduced nausea and other chemotherapy or radiotherapy side effects, etc. In the case of treating an inflammatory condition, the treatment can refer to, e.g., reducing blood levels of inflammatory cytokines, pain, swelling, recruitment of immune cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the present invention. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50/%, 75%, 80%, or 90%, or in some cases, no longer detectable using standard diagnostic techniques.

Compositions of this disclosure are useful in the treatment of proliferative diseases such as cancer. "Cancer", "tumor," "transformed" and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

The term "cancer" can refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, myelodisplastic syndromes (MDS), monocytic leukemia, myelogenous leukemia, acute lymphocytic leukemia, acute myelocytic leukemia (AML), chronic myeloid leukemia (CML), and multiple myeloma. In some embodiments, the compositions and methods of the present invention are useful for treating cancer.

Cancers that can be targeted include, for example, leukemia (e.g., acute lymphoblastic leukemia (ALL), acute myeloid leukemia (AML), chronic lymphocytic leukemia (CLL) and chronic myeloid leukemia (CML)), breast cancer, prostate cancer, colorectal cancer, brain cancer, esophageal cancer, head and neck cancer, bladder cancer, gynecological cancer, liposarcoma, and multiple myeloma. In some embodiments, the target binding domain within the CAR of the disclosed disclosure is capable of binding any of a broad group of targets, including but not limited to, GPR114, CLL-1, IL1RAP, TIM-3, CD19, CD20, CD22, ROR1, mesothelin, CD33, CD123/IL3Ra, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmel-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor, CD138, CEACAM5, CD56, CD70, CD74, GCC, 5T4, CD79b, Steap1, Napi2b, Lewis Y Antigen, LIV, c-RET, DLL3, EFNA4, Endosialin/CD248, Ly6e (RIG-e), CD79a, CD274 (PD-L1), CD38, DLL4, CD319 (SLAM7) and other targets known to one of skill in the art. In some embodiments, the cancer marker is CLL-1.

A "cancer target" or "cancer marker" is a molecule that is differentially expressed or processed in cancer, e.g., on a cancer cell or in the cancer milieu. Exemplary cancer targets are cell surface proteins such as IL1RAP (also, e.g., cell adhesion molecules and receptors), intracellular receptors, hormones, and molecules such as proteases that are secreted by cells into the cancer milieu. Markers for specific cancers are known in the art, e.g., MUC expression on colon and colorectal cancers, bombesin receptors in lung cancer, and prostate specific membrane antigen (PSMA) on prostate cancer.

The terms "overexpressed" or "upregulated" interchangeably refer to a protein or nucleic acid, generally a biomarker, that is transcribed or translated at a detectably greater level than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be at least any of 10%, 20%, 30%, 40%, 50%, 60%, 70%, 80%, 90% or more in comparison to a normal cell.

In some embodiments, the cancer target can be associated with a certain type of cancer cell, e.g., leukemia, myeloma, lymphoma, AML, CML, non-small cell lung cancer cells, prostate cancer, colorectal cancer, breast cancer or ovarian cancer. A cell type specific target is typically expressed at levels at least 2-fold greater in that cell type than in a reference population of cells. In some embodiments, the cell type specific marker is present at levels at least 3, 4, 5, 6, 7, 8, 9, 10 20, 50, 100, or 1000 fold higher than its average expression in a reference population. Thus, the target can be detected or measured to distinguish the cell type or types of interest from other cells. In some embodiments, the cancer treated is a leukemia, lymphoma or a solid tumor.

In some embodiments, the cancer treated is a cancer of myeloid origin, that is originating from myeloid cells. Chronic myeloproliferative disorders are a collection of conditions characterized by increased number of mature and immature granulocytes, erythrocytes, and platelets. Chronic myeloproliferative disorders can transition to other forms within this group, with a tendency to terminate in acute myeloid leukemia. Specific diseases within this group include cancers of myeloid origin, such as AML (acute myelogenous or myeloproliferative leukemia), MDS (myelodysplastic syndrome), myelofibrosis, CMML (chronic myelomonocytic leukemia), multiple myeloma, plasmacytoma, and CML (chronic myelogenous or myeloproliferative leukemia). Other myeloproliferative disorders include polycythemia vera, agnogenic myeloid leukemia, essential thrombocythemia, chronic myeloid leukemia, and chronic neutrophilic leukemia. In some embodiments, the cancer treated is a myeloproliferative cancer. In some embodiments, the myeloproliferative cancer is selected from the group consisting of acute myeloproliferative leukemia, myelodysplastic syndrome, chronic myeloproliferative leukemia, chronic myelomonocytic leukemia, multiple myeloma, plasmacytoma and myelofibrosis. In some embodiments, the cancer treated is a cancer of myeloid cell origin. In some embodiments, the cancer of myeloid cell origin is selected from the group consisting of acute myelogenous leukemia, myelodysplastic syndrome, chronic myelogenous leukemia, chronic myelomonocytic leukemia, multiple myeloma, plasmacytoma and myelofibrosis.

Specific diseases within this group include cancers of myeloid origin, such as AML (acute myelogenous or myeloproliferative leukemia), MDS (myelodysplastic syndrome), myelofibrosis, CMML (chronic myelomonocytic leukemia), multiple myeloma, plasmacytoma, and CML (chronic myelogenous or myeloproliferative leukemia). Other myeloproliferative disorders include polycythemia vera, agnogenic myeloid leukemia, essential thrombocythemia, chronic myeloid leukemia, and chronic neutrophilic leukemia. In some embodiments, the myeloproliferative cancer is selected from the group consisting of AML, CML, CMML, multiple myeloma, plasmacytoma and myelofibrosis.

Elevated CLL-1 levels are associated with cancer, in particular, in hematopoietic CSCs (e.g., LSCs), and in myeloproliferative disorders, including leukemias such as AML (acute myelogenous or myeloproliferative leukemia), MDS (myelodysplastic syndrome), myelofibrosis, CMML (chronic myelomonocytic leukemia), multiple myeloma, plasmacytoma, and CML (chronic myelogenous or myeloproliferative leukemia). See Bakker et al. (2004) Cancer Res. 64:8443; Van Rhenen et al. (2007) Blood 110:2659-66; Zhao et al. (2010) Haematologica (2010) 95:71; Van Rhenen et al. (2007) Leukemia 21:1700; and Herrmann et al. (2012) Haematologica 97:219.

A cancer stem cell (CSC) is a cell found in a tumor or blood cancer that can give rise to the cells that make up the bulk of the cancer. The CSC can also be self-renewing, similar to a normal (non-cancer) stem cell. CSCs can thus mediate metastasis by migrating to a non-tumor tissue in an individual and starting a "new" tumor. CSCs make up a very small percentage of any given cancer, depending on the stage that the cancer is detected. For example, the average frequency of CSCs in a sample of AML cells is believed to be about 1:10,000. Hematopoietic CSCs can be identified as CD34+, similar to normal hematopoietic stem cells (HSCs). Other CSC associated markers include CD44 (breast), CD133 (glial cancers), and Notch (e.g., myelomas and neuroblastoma).

One non-limiting example of a cancer target for which the IQB-CBIs described herein can be incorporated within an antibody-drug conjugate, is C type Lectin Like molecule1 ("CLL-1"). CLL-1 is expressed on AML blasts and LSCs, but not on normal hematopoietic stem cells. CLL-1 is expressed on leukemic cells within both the bone marrow and blood compartments. The target antigen is present across all AML French American British (FAB) classifications and cytogenetic risk categories and is expressed independent of FLT-3 status. The target is expressed in de novo and recurrent disease states. Expression of CLL-1 antigen in combination with multidrug resistance (MDR) is associated with poor disease prognosis and greater probability of relapse.

In addition to being expressed in AML, CLL-1 is expressed in MDS and other myeloproliferative disorders (e.g., polycythemia vera, essential thrombocythemia and polymyelofibrosis).

C-type Lectin-Like molecule 1 (CLL-1), also known as CLEC12A, DCAL-2, and MICL, is a type II membrane protein (ITIM domain—TM domain-stalk domain-lectin-like domain). The extracellular domain of CLL-1 is highly glycosylated, and it is expressed exclusively in cells of myeloid lineage.

The nucleotide and protein sequences of CLL-1 are known for many species. For example, the human sequences can be found at Genbank accession number AF247788.1 and Uniprot accession number Q5QGZ9. For the human CLL-1 protein, the extracellular domain comprises approximately amino acids 65-265, the transmembrane domain comprises approximately amino acids 44-64, and the cytoplasmic domain comprises approximately amino acids 1-43. The stalk domain of human CLL-1 spans amino acids 65-139, and the C lectin domain spans amino acids 140-249. One of skill will understand that CLL-1 variants (e.g., species homologs, allelic variants, etc.) can be optimally aligned, e.g., for identification of conserved residues and domains.

The terms "CLL-1 specific antibody," "anti-CLL-1 antibody," "CLL-1 antibody," "CLL-1 ADC" and "anti-CLL-1" are used synonymously herein to refer to an antibody (or antibody conjugate, depending on context) that specifically binds to CLL-1, including variously glycosylated forms of CLL-1. The CLL-1 antibodies described herein specifically bind the CLL-1 polypeptide expressed, e.g., on the surface of certain cancer cells, but not to HSCs. As discussed in more detail below, the present anti-CLL-1 antibodies can bind CLL-1 expressing cells, bind a larger percentage of AML cells compared to other AML-targeting antibodies, inhibit AML cell proliferation, and mediate their destruction.

A "CLL-1 associated disorder" (or CLL-1 related disorder, CLL-1 disorder, CLL-1 related condition or disease, etc.) refers to conditions and diseases correlated with elevated or reduced cell surface expression of CLL-1 as compared to CLL-1 expression in a standard control (e.g., a normal, non-disease, non-cancer cell). Elevated CLL-1 levels are associated with cancer cells, in particular, leukemias such as AML (acute myelogenous leukemia), MDS (myelodysplastic syndrome), and CML (chronic myelogenous leukemia), and in hematopoietic CSCs (e.g., LSCs).

One non-limiting example of an antibody that may be useful to target AML and cancer stem cells of involved lineages is an anti-CLL-1 antibody, and more specifically, a humanized anti-CLL1 antibody. Such antibodies are described, for example, in U.S. Patent Application Publication No. 2013/0295118 and PCT International Publication No. WO 2017/091615A1, both incorporated herein by reference. In some embodiments, the anti-CLL-1 antibody is optionally a chimeric (e.g., humanized) antibody referred to as "C6" and comprises light chain variable region:

```
                                     (SEQ ID NO: 1)
DIQMTQSPSSLSASVGDRVTLTCRATQELSGYLSWLQQKPGKAIKRLIYA
ASTLDSGVPSRFSGNRAGTDYTLTISSLQPEDFATYYCLQYAIYPYTFGQ
GTKLEIK
``` and heavy chain variable region:

```
                                     (SEQ ID NO: 2)
EVQLVQSGAEVKKPGASVKMSCKASGYTFTSYFIHWVRQAPGQGLEWIGF
INPYNDGSKYAQKFQGRATLTSDKSTSTVYMELSSLRSEDTAVYYCTRDD
GYYGYAMDYWGQGTLVTVSS,
``` respectively.

In another non-limiting example of an antibody that may be useful to target AML and cancer stem cells of involved lineages is an anti-IL1RAP antibody, and more specifically, a humanized anti-IL1RAP antibody. As used herein "IL1-RAP" refers to human interleukin 1 receptor accessory protein. A sequence of IL1-RAP can be as shown in Uniprot accession number Q9NPH3-1 (isoform 1). IL1RAP expression is elevated on cancer cells (e.g., B cell lymphoma, AML cells, and solid tumor cells described herein); CSCs (e.g., myeloid CSCs); and cells associated with the IL1RAP associated disorders provided herein. IL1RAP is not significantly expressed on normal hematopoietic stem cells (HSCs). IL1RAP antibodies are described, for example, in U.S. Provisional Patent Application No. 62/425,970 and U.S. Patent Application Publication No. 2015/0315279 both incorporated herein by reference.

In some embodiments, the anti-IL1RAP antibody is referred to as "3G7". In a chimeric antibody, 3G7 can have light chain variable and heavy chain variable sequences as follows (CDRs indicated in bold highlight):

```
3G7 light chain variable sequence:
                                     (SEQ ID NO: 5)
DIVLTQSPATLSVTPGDSVSLSCRASQSISNNLHWYQQKSHESPRLLIKY
ASQSISGIPSRFSGSGSGTDFTLSINSVETEDFGVYFCQQSHNWPHTFGG
GTKLEIKR,
and 3G7 heavy chain variable region sequence:
                                     (SEQ ID NO: 6)
QIQLVQSGPELKKPGETVKISCKASGYTFTNYGMHWVKQSPGEGLKWMGW
INTYTGEPTYADDFKGRFGFSLETSASSAYLQINDLKNEDMATYFCARYY
GNFDYWGQGTTLTVSS.
```

In some embodiments, the 3G7 anti-IL1RAP antibody is a humanized antibody and comprises:

```
light chain:
                                     (SEQ ID NO: 3)
EIVMTQSPATLSVSPGERATLSCRASQSISNNLHWYQQKPGQAPRLLIYY

ASQSISGIPARFSGSGSGTEFTLTISSLQSEDFAVYYCQQSHNWPHTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC, heavy chain:
                                     (SEQ ID NO: 4)
EVQLVQSGAEVKKPGASVKISCKASGYTFTNYGMHWVRQAPGQGLEWMGW

INTYTGEPTYAQKFQGRFTFTLDTSTSTAYLEIRSLRSDDTAVYYCARYY

GNFDYWGQGTLLTVSSASTKGPSVFPLAPSSKSTSGGTAALGCLVKDYFP

EPVTVCWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

CDRs and a cysteine substitution for attachment of the payload linker are set forth in bold and underline.

In certain embodiments, the antibody can include substitutions of a cysteine residue for another residue. Compositions of this disclosure can be attached to the antibodies through the cysteine residue. In one example, a serine residue at position 156 is substituted with cysteine (S156C). In another example, a serine residue at position 239 is substituted with cysteine (S239C). More than one IQB-CBI compound may be incorporated into antibodies so modified. In some embodiments, the number of IQB-CBI compounds attached to an antibody may be any number in the range from 1 to about 10, or any number in between, including a fractional number. In some embodiments, the number of IQB-CBI compounds attached to the antibody is in the range from 1 to about 3. Such an antibody incorporating the IQB-CBIs described herein have been found to be effective in invitro and invivo applications as described below.

B. Dosage

The amount of compounds that will be effective in the treatment or prevention of proliferative disorders in a subject will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the relative activity of the compounds, the age, body weight, general physical and mental health, genetic factors, environmental influences, sex, diet, time of administration, route of administration, rate of excretion, and the severity of the particular problem being treated.

The terms "dose" and "dosage" are used interchangeably herein. A dose refers to the amount of active ingredient given to an individual at each administration. For the present invention, the dose can refer to the concentration of the antibody or associated components. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

In certain embodiments, the compounds of the disclosure will be conjugated to a target binding moiety, such as an antibody. The target binding moiety can be specific to targets on cells targeted for elimination in order to treat a subject suffering from a condition caused by the presence of such cells. The target can be any biomolecule on a target cell. Target cells can include cancer cells. Therefore, the target can comprise, for example, a polypeptide expressed on a cancer cell, e.g., a tumor-associated antigen. In another embodiment, the target binding moiety can be a chimeric antigen receptor ("CAR") that can bind an antigen determinant comprising amino acids within the extracellular domain of a tumor-associated antigen, a viral antigen or a viral associated antigen or a fragment of such a polypeptide.

Suitable dosage ranges for oral administration are dependent on the potency of the particular compound or compound antibody conjugates, but are generally about 0.001 mg to about 500 mg of drug per kilogram body weight, preferably from about 0.1 mg to about 200 mg of drug per kilogram body weight, and more preferably about 1 to about 100 mg/kg-body wt. per day. Dosage ranges may be readily determined by methods known to the skilled artisan. The amount of active ingredient that may be, for instance, combined with carrier materials to produce a single dosage form will vary depending upon the subject treated and the particular mode of administration. Dosage unit forms will generally contain between about 1 mg to about 500 mg of active ingredient.

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The subject can be monitored to adjust the dosage and frequency of administration depending on therapeutic progress and any adverse side effects, as will be recognized by one of skill in the art.

Thus in some embodiments, additional administration is dependent on subject progress, e.g., the subject is monitored between administrations. For example, after the first administration or round of administrations, the subject can be monitored for rate of tumor growth, recurrence (e.g., in the case of a post-surgical subject), or general disease-related symptoms such as weakness, pain, nausea, etc.

C. Methods of Administration

Compositions comprising the IQB-CBI compound or the IQB-CBI antibody conjugate may be administered by any convenient route, for example, by infusion or bolus injection, or by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer the antibody conjugate compositions. Methods of administration include, but are not limited to, intradermal, intramuscular, intraperitoneal, intravenous, subcutaneous, intranasal, epidural, intranasal, and intracerebral.

The amount of compound antibody conjugates that will be effective in the treatment or prevention of proliferative disorders in a subject will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the relative activity of the compound antibody conjugates, the age, body weight, general physical and mental health, genetic factors, environmental influences, sex, diet, time of administration, route of administration, rate of excretion, and the severity of the particular problem being treated.

The IQB-CBI conjugates or the IQB-CBI antibody conjugate can be administered by injection or infusion through any suitable route including but not limited to intravenous, subcutaneous, intramuscular or intraperitoneal routes. An example of administration of a pharmaceutical composition includes storing the composition at 10 mg/ml in sterile isotonic aqueous saline solution for injection at 4° C., and diluting it in either 100 ml or 200 ml 0.9% sodium chloride for injection prior to administration to the subject. The composition is administered by intravenous infusion over the course of 1 hour at a dose of between 0.2 and 10 mg/kg. In other embodiments, the composition is administered by intravenous infusion over a period of between 15 minutes and 2 hours. In still other embodiments, the administration procedure is via sub-cutaneous bolus injection.

Thus in some embodiments, additional administration is dependent on the progress of the subject, e.g., the subject is monitored between administrations.

D. Kits

Also provided herein are kits comprising containers containing compositions as provided herein. In certain embodiments, the containers contain a unit dose of the composition. Kits can comprise boxes containing a plurality of composition-containing containers. In other embodiments, kits comprise a container, such as a bag or bottle, containing a composition of this disclosure connected to an insersion device, such as a needle, for example, through a tube that function as a conduit for the composition in the container.

The following examples are offered by way of illustration and not by way of limitation.

Examples

Example 1: Experimental Protocols for the Synthesis of IQB-CBI Dimers

General Methods:

$^1$H NMR spectra were recorded on a Varian Inova 300 or 500 MHz NMR instrument. Chromatographic purities were determined on an Agilent 1200 Series or 1100 Series LC/MS system using a Merck Chromolith RP-18e analytical HPLC column (monolithic, 50×2 mm) and the following analytical HPLC method: injection volume 5 μL; flow rate 1 mL/min; 5→95% acetonitrile in water with 0.05% AcOH over 5 mins; Agilent diode array detector at λ=254, 220 or 195 nm; room temperature.

Synthesis of IQB-acids 11a-e (Scheme 1)
(Referring to FIG. 1)

4-Benzyloxy-5-methoxy-2-nitro-benzoic acid methyl ester (2)

4-Benzyloxy-5-methoxy-benzoic acid methyl ester 1 (13.6 g, 50 mmol) was dissolved in acetic anhydride (130 mL). Copper nitrate trihydrate (15.1 g, 62.5 mmol) was added in small portions over period of 30 minutes. After stirring for 1 h reaction mixture was poured on ice and stirred for 1 h. Precipitate was filtered off, washed with water and dried thoroughly. Material was recrystallized from ethyl acetate to afford 9.1 g of 2 (57% yield).

$^1$H NMR (500 MHz, CDCl$_3$) δ: 7.52 (s, 1H), 7.36-7.46 (m, 5H), 7.09 (s, 1H), 5.22 (s, 2H), 3.99 (s, 3H), 3.91 (s, 3H).

LC/MS: retention time 3.18 min. (ESI) C$_{16}$H$_{16}$NO$_6$ calculated for [M+H]$^+$ 318; found 340 (M+Na).

4-Benzyloxy-5-methoxy-2-nitro-benzoic acid (3)

4-Benzyloxy-5-methoxy-benzoic acid methyl ester (9.1 g, 29 mmol) was dissolved in methanol (145 mL) and sodium hydroxide (6 M solution, 24 mL) was added at once. Reaction mixture was stirred for 1 h at 50 degrees and methanol was evaporated. Concentrated hydrochloric acid (12 mL) was added slowly to the residue with stirring. Formed precipitate was filtered off, washed with water and dried to afford 8.1 g of 3 (92% yield).

$^1$H NMR (500 MHz, DMSO-d6) δ: 7.69 (s, 1H), 7.36-7.47 (m, 5H), 7.31 (s, 1H), 5.24 (s, 2H), 3.91 (s, 3H).

(S)-1,2,3,4-Tetrahydro-isoquinoline-3-carboxylic acid methyl ester (5)

(S)-1,2,3,4-Tetrahydro-isoquinoline-3-carboxylic acid 4 (10.6 g, 60 mmol) was dissolved in anhydrous methanol (86 mL). Thionyl chloride (6.5 mL, 90 mmol) was added dropwise and reaction mixture was refluxed for 5 h. Methanol was evaporated and residue was partitioned in chloroform and saturated sodium bicarbonate solution. Water phase was additionally extracted with chloroform, and combined organics were dried over anhydrous MgSO$_4$, filtered and concentrated to dryness to afford 9.2 g of 5 (81% yield).

$^1$H NMR (500 MHz, CDCl$_3$) δ: 7.16 (br, 3H), 7.03 (br, 1H), 4.13 (br, 2H), 3.80 (br, 3H), 3.05 (br, 2H), 2.20 (br, 1H).

(S)-2-(4-Benzyloxy-5-methoxy-2-nitro-benzoyl)-1,2,3,4-tetrahydro-ioquinoline-3-carboxylic acid methyl ester (6)

Acid 3 (3.03 g, 10 mmol) was dissolved in dichloromethane (33 mL), and DIEA (2.6 mL, 15 mmol) was added followed by HATU (4.93 g, 13 mmol). Mixture was stirred for 30 minutes and amine 5 (2.29 g, 12 mmol) was added at once. Reaction mixture was allowed to stir overnight, then washed with 0.5 M HCl, saturated NaHCO$_3$ and concentrated to dryness. The residue was purified on a 110 g silica Teledyne Isco column (0→35% EtOAc in hexane). Evaporation of product containing fractions afforded 2.73 g of 6 (57% yield).

LC/MS: retention time 3.31 min. (ESI) C$_{26}$H$_{25}$N$_2$O$_7$ calculated for [M+H]$^+$ 477; found 477.

2-Benzyloxy-3-methoxy-11,11a-dihydro-6H,13H-5a,13-diaza-benzo[4,5]cyclohepta[1,2-b]naphthalene-5,12-dione (7)

Nitro derivative 6 (2.71 g, 5.7 mmol), zinc (7.41 g, 114 mmol) and NH$_4$Cl (12.2 g 228 mmol) were placed in flask with stirring bar and acetone/water (125 mL, 1:4 v/v) was added. The reaction mixture was stirred overnight and then filtered off through celite and concentrated. The residue was dissolved in methanol (100 mL) and stored for 24 hr at rt. Formed precipitate was filtered off, washed thoroughly with water and dried to afford 2.18 g of 7 (92% yield).

$^1$H NMR (500 MHz, DMSO-d6) δ: 7.46 (m, 2H), 7.42 (m, 2H), 7.36 (m, 1H), 7.21-7.33 (m, 5H), 6.80 (s, 1H), 5.09 (s, 2H), 4.86 (d, J=15.1 Hz, 1H), 4.42 (d, J=15.1 Hz, 1H), 4.21 (t, J=6.4 Hz, 1H), 3.77 (s, 3H), 3.27 (m, 1H), 2.99 (m, 1H).

LC/MS: retention time 2.82 min. (ESI) C$_{25}$H$_{23}$N$_2$O$_4$ calculated for [M+H]$^+$ 415; found 415.

2-Benzyloxy-3-methoxy-13-(2-trimethylsilanyl-ethoxymethyl)-11,11a-dihydro-6H,13H-5a,13-diaza-benzo[4,5]cyclohepta[1,2-b]naphthalene-5,12-dione (8)

To suspension of amide 7 (2.20 g, 5.3 mmol) in THF-DMF (40 mL, 3:1 v/v) sodium hydride in mineral oil (424 mg, 10.6 mmol) was added in small portions. After stirring for 30 minutes, reaction mixture was cooled to −78° C. and SEMCl (2.34 mL, 13.3 mmol) was added dropwise. Solution was allowed to warm to rt and stirred overnight. THF was removed under reduced pressure and residue was partitioned in chloroform-water. Water phase was additionally extracted with chloroform, and combined organics were dried over anhydrous $MgSO_4$, filtered, concentrated to dryness. The residue was purified on a 40 g silica Teledyne Isco column (0→50% EtOAc in hexane). Evaporation of product containing fractions afforded 2.55 g of 8 (88% yield).

$^1$H NMR (500 MHz, $CDCl_3$) δ: 7.46 (m, 2H), 7.37 (m, 2H), 7.31 (m, 4H), 7.25 (m, 3H), 5.43 (d, J=9.8 Hz, 1H), 5.21 (s, 2H), 5.14 (d, J=15.1 Hz, 1H), 4.49 (d, J=9.8 Hz, 1H), 4.41 (d, J=15.1 Hz, 1H), 4.27 (t, J=6.4 Hz, 1H), 3.92 (s, 3H), 3.70 (m, 1H), 3.56 (m, 2H), 2.99 (m, 1H), 0.97 (m, 2H), 0.05 (s, 9H).

LC/MS: retention time 3.92 min. (ESI) $C_{31}H_{37}N_2O_5Si$ calculated for $[M+H]^+$ 545; found 545.

2-Hydroxy-3-methoxy-13-(2-trimethylsilanyl-ethoxymethyl)-11,11a-dihydro-6H,13H-5a,13-diaza-benzo[4,5]cyclohepta[1,2-b]naphthalene-5,12-dione (9)

Solution of 8 (2.55 g, 4.7 mmol) in methanol (47 mL) was flushed with Ar and 10% Pd/C (375 mg) was added. Hydrogen (balloon) was bubbled through solution for 2 h and then reaction mixture was filtered off through celite, concentrated and purified on 24 g silica Teledyne Isco column (0→60% EtOAc in hexane). Evaporation of product containing fractions afforded 2.13 g of 9 (99% yield).

$^1$H NMR (500 MHz, $CDCl_3$) δ: 7.32 (m, 2H), 7.27 (m, 4H), 6.06 (br, 1H), 5.42 (d, J=9.8 Hz, 1H), 5.15 (d, J=15.1 Hz, 1H), 4.70 (d, J=9.8 Hz, 1H), 4.41 (d, J=15.1 Hz, 1H), 4.28 (t, J=6.4 Hz, 1H), 3.93 (s, 3H), 3.71 (m, 1H), 3.62 (m, 2H), 3.00 (m, 1H), 0.99 (m, 2H), 0.03 (s, 9H).

LC/MS: retention time 3.22 min. (ESI) $C_{24}H_{31}N_2O_5Si$ calculated for $[M+H]^+$ 455; found 455.

SEM-Protected IQB-Acid (10a)

To a solution of phenol 9 (90 mg, 0.2 mmol), 2-bromoacetic acid (83 mg, 0.6 mmol) in DMF (0.8 mL) cesium carbonate (197 mg, 0.6 mmol) was added and mixture was stirred overnight. No product was formed and MeOH (0.5 mL) was added and mixture was stirred for additional 24 hr after that LC/MS showed 100% conversion. Reaction mixture was diluted with water (10 mL) and saturated with solid $NH_4Cl$. After extraction with DCM:MeOH (15 mL, 10:1 v/v) organics were concentrated to dryness and purified on a 12 g silica Teledyne Isco column (0→15% MeOH with 0.1% AcOH in DCM). Evaporation of product containing fractions afforded 120 mg of 10a (>99% yield).

$^1$H NMR (500 MHz, $CDCl_3$) δ: 10.73 (br, 1H), 7.32 (s, 1H), 7.29 (m, 2H), 7.24 (m, 2H), 7.19 (s, 1H), 5.43 (d, J=9.8 Hz, 1H), 5.12 (d, J=15.1 Hz, 1H), 4.65 (d, J=9.8 Hz, 1H), 4.40 (d, J=15.1 Hz, 1H), 4.27 (t, J=6.8 Hz, 2H), 3.88 (s, 3H), 3.67 (m, 2H), 3.53 (m, 1H), 3.10 (m, 2H), 2.99 (m, 1H), 0.96 (m, 2H), 0.00 (s, 9H).

LC/MS: retention time 3.44 min. (ESI) $C_{26}H_{33}N_2O_7Si$ calculated for $[M+H]^+$ 513; found 513.

SEM-Protected IQB-Acid (10b)

To a solution of phenol 9 (136 mg, 0.3 mmol), 2-(2-bromoethyl)-1,3-dioxolane (108 mg, 0.6 mmol) in DMF (0.6 mL), cesium carbonate (295 mg, 0.9 mmol) was added and mixture was stirred for 2 hr. LC/MS showed 100% conversion. Reaction mixture was diluted with water (10 mL) and extracted with EtOAc (2×15 mL) organics were concentrated to dryness and dissolved in THF (8 mL). 6 M HCl (1 mL) was added and reaction mixture was stirred at rt for 24 hr and finally concentrated to dryness to produce crude aldehyde.

Crude aldehyde was dissolved in tBuOH/2-methyl-2-butene/water (3/1/1 v/v/v; 10 mL), sodium dihydrogen phosphate (420 mg, 2.1 mmol) followed by sodium chlorite (244 mg, 2.7 mmol). Reaction mixture was stirred vigorously for 30 minutes and LC/MS indicated reaction was complete. Organic layer was separated; water was extracted with EtOAc (2×20 mL). Combined organics were concentrated to dryness and purified on preparative TLC plates (Hexane:EtOAc:AcOH, 1:1:0.05). Silica gel containing product was scraped off and washed with DCM:MeOH (15:1, v/v) and organic solution evaporated to afford 78 mg of 10b (49% yield).

$^1$H NMR (500 MHz, $CDCl_3$) δ: 7.31 (br m, 8H), 5.49 (br m, 1H), 5.12 (br d, J=15.1 Hz, 1H), 4.69 (br m, 1H), 4.42 (br d, J=15.1 Hz, 1H), 4.28 (br m, 2H), 3.54-3.93 (br m, 7H), 2.99 (br m, 1H), 0.96 (br m, 2H), 0.00 (br s, 9H).

LC/MS: retention time 3.13 min. (ESI) $C_{27}H_{35}N_2O_7Si$ calculated for $[M+H]^+$; 527; found 527.

SEM-Protected IQB-Acid (10c)

To a solution of phenol 9 (90 mg, 0.2 mmol), ethyl 4-bromobutanoate (117 mg, 0.6 mmol) in DMF (0.4 mL), cesium carbonate (197 mg, 0.6 mmol) was added and mixture was stirred for 2 hr. LC/MS showed 100%/o conversion. Reaction mixture was diluted with water (10 mL) and extracted with EtOAc (2×15 mL), organicfractions were concentrated to dryness and dissolved in THF-MeOH—$H_2O$ (3-1-1, v/v/v, 2 mL). LiOH (32 mg, 1.3 mmol) was added and reaction mixture was stirred for 3 hr and then concentrated to dryness. The residue was dissolved in DMSO (1 mL) and loaded directly onto a 15.5 g $C_{18}$ Aq Isco column and purified (5→95% ACN in $H_2O$, each containing 0.05% of AcOH). Desired fractions were lyophilized to obtain 88 mg of 10c (81% yield).

$^1$H NMR (500 MHz, $CDCl_3$) δ: 7.31 (s, 1H), 7.30 (m, 2H), 7.27 (m, 2H), 7.21 (s, 1H), 5.49 (d, J=9.8 Hz, 1H), 5.15 (d, J=15.1 Hz, 1H), 4.69 (d, J=9.8 Hz, 1H), 4.42 (d, J=15.1 Hz, 1H), 4.28 (t, J=6.8 Hz, 2H), 4.11 (m, 2H), 3.88 (s, 3H), 3.77 (m, 1H), 3.67 (m, 1H), 3.56 (m, 1H), 3.01 (m, 1H), 2.60 (m, 2H), 2.19 (m, 2H), 0.97 (m, 2H), 0.00 (s, 9H).

LC/MS: retention time 3.29 min. (ESI) $C_{27}H_{37}N_2O_7Si$ calculated for $[M+H]^+$ 541; found 541.

SEM-Protected IQB-Acid (10d)

To a solution of phenol 9 (100 mg, 0.22 mmol), methyl-5-bromovalerate (129 mg, 0.66 mmol) in DMF (0.4 mL), cesium carbonate (215 mg, 0.66 mmol) was added and the mixture was stirred for 16 hr. LC/MS showed 100% conversion. Reaction mixture was diluted with water (10 mL) and extracted with EtOAc (2×15 mL) organic fractions were concentrated to dryness and dissolved in THF-MeOH—$H_2O$ (3-1-1, v/v/v, 2 mL). LiOH (17 mg, 0.69 mmol) was added and reaction mixture was stirred for 1 hr and then concentrated to dryness. The residue was dissolved in DMSO (1 mL) and loaded directly onto a 50 g $C_{18}$ Aq Isco column and purified (5→95% ACN in $H_2O$, each containing 0.05% of AcOH). Desired fractions were lyophilized to obtain 107 mg of 10d (83% yield).

$^1$H NMR (500 MHz, $CDCl_3$) δ: 7.36-7.14 (m, 6H), 5.50 (d, J=10.0 Hz, 1H), 5.15 (d, J=15.3 Hz, 1H), 4.67 (d, J=10.0 Hz, 1H), 4.41 (d, J=15.3 Hz, 1H), 4.28 (dd, J=7.4, 6.4 Hz, 1H), 4.15-4.00 (m, 2H), 3.89 (s, 3H), 3.79 (td, J=9.8, 6.7 Hz,

1H), 3.68 (td, J=9.7, 6.7 Hz, 1H), 3.56 (dd, J=15.4, 7.5 Hz, 1H), 3.00 (dd, J=15.5, 6.4 Hz, 1H), 2.47 (t, J=7.2 Hz, 2H), 1.94 (q, J=7.4 Hz, 2H), 1.86 (q, J=7.4 Hz, 2H), 1.05-0.87 (m, 2H), 0.03 (s, 9H).

LC/MS: retention time 3.34 min. (ESI) $C_{29}H_{37}N_2O_7Si$ calculated for [M–H]⁻ 543; found 543.

SEM-Protected IQB-Acid (10e)

To a solution of phenol 9 (227 mg, 0.5 mmol), methyl 6-bromohexanoate (313 mg, 1.5 mmol) in DMF (1 mL) cesium carbonate (313 mg, 1.5 mmol) was added and mixture was stirred for 2 hr. LC/MS showed 100% conversion. Reaction mixture was diluted with water (10 mL) and extracted with diethyl ether (2×15 mL) organics were concentrated to dryness and dissolved in THF-MeOH—H₂O (3-1-1, v/v/v, 4 mL). LiOH (64 mg, 2.6 mmol) was added and reaction mixture was stirred for 3 hr and then concentrated to dryness. The residue was dissolved in ACN-H₂O (1-1, v/v, 2 mL) and loaded directly onto a 50 g $C_{18}$ Aq Isco column and purified (5→95% ACN in $H_2O$, each containing 0.05% of AcOH). Desired fractions were lyophilized to obtain 260 mg of 10e (92% yield).

¹H NMR (500 MHz, CDCl₃) δ: 7.32 (m, 3H), 7.27 (m, 2H), 7.21 (m, 1H), 5.51 (d, J=9.8 Hz, 1H), 5.15 (d, J=15.1 Hz, 1H), 4.68 (d, J=9.8 Hz, 1H), 4.43 (d, J=15.1 Hz, 1H), 4.30 (t, J=6.8 Hz, 1H), 4.05 (m, 1H), 3.89 (s, 3H), 3.79 (m, 1H), 3.69 (m, 1H), 3.56 (m, 1H), 3.0.1 (m, 1H), 2.40 (m, 2H), 1.90 (m, 2H), 1.75 (m, 2H), 1.55 (m, 2H), 0.98 (m, 2H), 0.00 (s, 9H).

LC/MS: retention time 3.42 min. (ESI) $C_{30}H_{41}N_2O_7Si$ calculated for [M+H]⁺ 569; found 569.

IQB-Acid (11a)

SEM-protected IQB-acid 10a (102 mg, 0.2 mmol) was dissolved in anhydrous THF (4 mL) and mixture was cooled to −78° C. and superhydride solution (0.5 mL, 1 M in THF, 0.5 mmol) was added dropwise. Solution was kept at that temperature for 90 minutes and then warmed to rt before quenching with MeOH (1 mL). All volatiles were removed on rotovap, residue was dissolved in DMSO and loaded directly onto a 15.5 g $C_{18}$ Aq Isco column and purified (5→95% ACN in $H_2O$, each containing 0.05% of AcOH). Desired fractions were lyophilized to obtain 51 mg of 1a (70% yield).

¹H NMR (500 MHz, CDCl₃) δ: 7.57 (s, 1H), 7.48 (br, 1H), 7.32 (m, 5H), 6.89 (s, 1H), 5.02 (d, J=15.6 Hz, 1H), 4.78 (m, 2H), 4.48 (d, J=15.6 Hz, 1H), 4.01 (m, 1H), 3.98 (s, 3H), 3.28 (m, 1H), 3.16 (m, 1H).

LC/MS: retention time 2.10 min. (ESI) $C_{20}H_{19}N_2O_5$ calculated for [M+H]⁺ 367; found 367.

IQB-Acid (11b)

Procedure as described for 11a. Obtained 51 mg of 11b (60% yield).

¹H NMR (500 MHz, CDCl₃) δ: 7.54 (s, 1H), 7.46 (br, 1H), 7.32 (m, 5H), 6.94 (s, 1H), 5.02 (d, J=15.6 Hz, 1H), 4.53 (d, J=15.6 Hz, 1H), 4.35 (m, 2H), 3.92 (s, 3H), 3.27 (m, 1H), 3.15 (m, 1H), 2.90 (m, 2H).

LC/MS: retention time 2.10 min. (ESI) $C_{21}H_{21}N_2O_5$ calculated for [M+H]⁺ 381; found 381.

IQB-Acid (11c)

Procedure as described for 11s. Obtained 51 mg of 11e (61% yield).

¹H NMR (500 MHz, CDCl₃) δ: 7.53 (s, 1H), 7.46 (br, 1H), 7.34 (m, 5H), 6.88 (s, 1H), 5.02 (d, J=15.6 Hz, 1H), 4.54 (d, J=15.6 Hz, 1H), 4.11 (m, 2H), 3.93 (m, 4H), 3.27 (m, 1H), 3.16 (m, 1H), 2.58 (m, 2H), 2.18 (m, 2H).

LC/MS: retention time 2.10 min. (ESI) $C_{22}H_{23}N_2O_5$ calculated for [M+H]⁺ 395; found 395.

IQB-Acid (11d)

Procedure as described for 11a. Obtained 56 mg of 11d (49% yield).

¹H NMR (500 MHz, CDCl₃) δ 7.53 (s, 1H), 7.48 (d, J=5.1 Hz, 1H), 7.43-7.28 (m, 4H), 6.82 (s, 1H), 5.01 (d, J=15.5 Hz, 1H), 4.56 (d, J=15.5 Hz, 1H), 4.18-4.02 (m, 3H), 3.95 (s, 3H), 3.28 (dd, J=15.5, 5.6 Hz, 1H), 3.16 (dd, J=15.5, 4.1 Hz, 1H), 2.46 (t, J=7.2 Hz, 2H), 1.94 (q, J=7.0, 6.4 Hz, 2H), 1.86 (q, J 7.4 Hz, 2H).

LC/MS: retention time 2.18 min. (ESI) $C_{23}H_{25}N_2O_5$ calculated for [M+H]⁺ 409; found 409.

IQB-Acid (11e)

Procedure as described for 11a. Obtained 140 mg of 11e (72% yield).

¹H NMR (500 MHz, CDCl₃) δ: 7.54 (s, 1H), 7.48 (br, 1H), 7.32 (m, 5H), 6.82 (s, 1H), 5.02 (d, J=15.6 Hz, 1H), 4.57 (d, J=15.6 Hz, 1H), 4.01 (m, 2H), 3.98 (m, 4H), 3.28 (m, 1H), 3.16 (m, 1H), 2.39 (m, 2H), 1.90 (m, 2H), 1.73 (m, 2H), 1.54 (m, 2H).

LC/MS: retention time 2.24 min. (ESI) $C_{24}H_{27}N_2O_5$ calculated for [M+H]⁺ 423; found 423.

Figure 2:
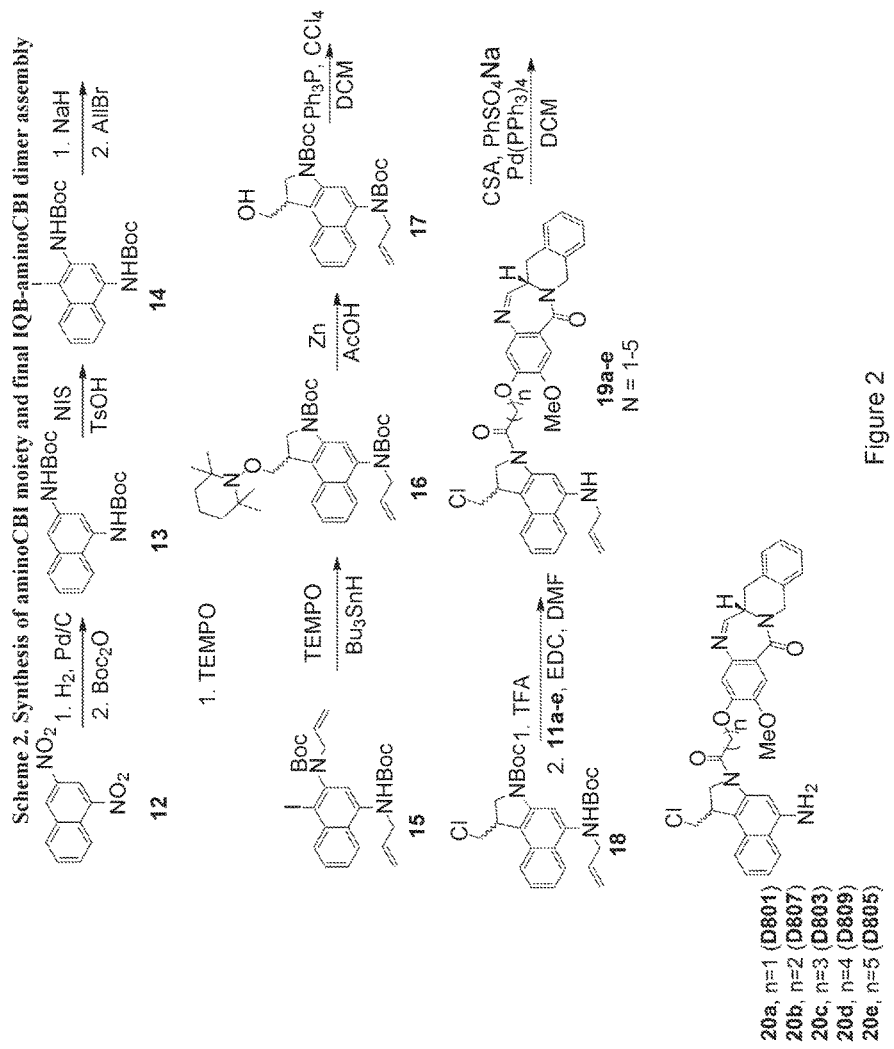
FIG. 2 shows the synthesis of aminoCBI moiety and final assembly of an IQB-aminoCBI dimer.

Synthesis of IQB-aminoCBI Dimers—20a-e
(Scheme 2, Referring to FIG. 2)

(3-tert-Butoxycarbonylamino-naphthalen-1-yl)-carbamic Acid Tert-Butyl Ester (13)

To an Ar purged solution of 1,3-dinitro-naphthalene 412) (20.0 g, 92.0 mmol) in methanol (400 mL) was added 10% Pd/C (2.0 g). The mixture was degassed and purged with H₂ (3×). The resulting reaction mixture was stirred under 1 atm of H₂ gas for 16 h at which time the reaction was judged complete by LC/MS. The catalyst was removed from the reaction mixture via filtration through celite. The reaction was concentrated in vacuo and the crude product was used without further purification.

Boc₂O (116 g, 535 mmol) was added to a solution of crude 1,3-diamino-naphthaline in THF (400 mL). The resulting mixture was stirred at 60° C., under Ar, until the reaction was judged complete by TLC and LC/MS. The reaction mixture was concentrated in vacuo. The resulting residue was purified by column chromatography (0→30% EtOAc in Hex) to afford 20.0 g of 13 (61% yield).

LC/MS: retention time 3.55 min. (ESI) calculated for $C_{12}H_{10}N_2O_4$: [M-2tBu]⁺ 247; found 247.

(4-tert-Butoxycarbonylamino-1-iodo-naphthalen-2-yl)-carbamic acid tert-butyl ester (14)

A degassed solution of (3-tert-butoxycarbonylamino-naphthalen-1-yl)-carbamic acid tert-butyl ester (13) (20.0 g, 56.0 mmol) in 1:1 THF/MeOH (150 mL), under Ar, was cooled to -78° C. A solution of NIS (14.4 g, 64.2 mmol) in THF (50 mL) was added, followed by a solution of p-TsOH (21.3 g, 112 mmol) in MeOH (50 mL). The mixture was stirred at −78° C. until the reaction was judged complete by LC/MS. The mixture was then allowed to warm to room temperature, diluted with EtOAc (200 mL) washed with H₂O (2×100 mL), then brine (2×100 mL), dried over MgSO₄, filtered and concentrated in vacuo. The resulting residue was purified by column chromatography (0→50% EtOAc in Hex) to afford 17.8 g of 12 (66% yield).

LC/MS: retention time 3.96 min. (ESI) calculated for $C_{20}H_{25}IN_2O_4Na$: [M+Na]$^+$ 507; found 507.

Allyl-[3-(allyl-tert-butoxycarbonyl-amino)-4-iodo-naphthalen-1-yl]-carbamic acid ten-butyl ester (15)

To a solution of (4-tert-butoxycarbonylamino-1-iodo-naphthalen-2-yl)-carbamic acid tert-butyl ester (14) (13.5 g, 27.9 mmol) in DMF (100 mL) under Ar, cooled to 0° C. was added NaH (60% in mineral oil) (3.34 g, 83.6 mmol). The mixture was stirred at 0° C. for 30 min followed by the addition of allyl bromide (24.0 mL, 279 mmol) over 5 min. The resulting mixture was allowed to warm to room temperature over 2 h, at which point the reaction was judged complete. The reaction was then diluted with EtOAc (500 mL) and washed with NaHCO$_3$ (sat, aq) (2×100 mL), H$_2$O (2×100 mL), then brine (2×100 mL), dried over MgSO$_4$, filtered and concentrated in vacuo. The resulting residue was purified by column chromatography (0→50% EtOAc in Hex) to afford 11.9 g of 15 (76% yield).

LC/MS: retention time 4.34 min. (ESI) calculated for $C_{26}H_{33}IN_2O_4Na$: [M+Na]$^+$ 587; found 587.

5-(Allyl-tert-butoxycarbonyl-amino)-1-(2,2,6,6-tetramethyl-piperidin-1-yloxymethyl)-1,2-dihydro-benzo[e]indole-3-carboxylic acid ter-butyl ester (16)

To a solution of (allyl-[3-(allyl-tert-butoxycarbonyl-amino)-4-iodo-naphthalen-1-yl]-carbamic acid tert-butyl ester (15) (11.0 g, 19.5 mmol) in benzene (400 mL), under Ar, was added TEMPO (9.0 g, 58 mmol) and Bu$_3$SnH (5.3 mL, 19.5 mmol). The mixture was stirred at 60° C. for 30 min, then another equivalent of Bu$_3$SnH (5.3 mL, 19.5 mmol) was added. After an additional 30 min, TEMPO (6.1 g, 39 mmol) and Bu$_3$SnH (5.3 mL, 19.5 mmol) were added and the mixture was stirred for another 30 min, at which point more TEMPO (6.1 g 39 mmol) was added. After another 20 min, a final portion of Bu$_3$SnH (5.3 mL, 19.5 mmol) was added. The resulting mixture was stirred for 45 min at 60° C. The reaction was cooled to room temperature and concentrated in vacuo. The resulting residue was purified by column chromatography (0→10% EtOAc in Hex, very slow gradient) to afford 10.5 g of 16 (91% yield).

LC/MS: retention time 5.33 min. (ESI) calculated for $C_{35}H_{51}N_3O_5$: [M+H]$^+$ 594; found 594.

tert-Butyl 5-(allyl(tert-butoxycarbonyl)amino)-1-(hydroxymethyl)-1,2-dihydro-3H-benzo[e]indole-3-carboxylate (17)

To a solution of 5-(allyl-tert-butoxycarbonyl-amino)-1-(2,2,6,6-tetramethyl-piperidin-1-yloxymethyl)-1,2-dihydro-benzo[e]indole-3-carboxylic acid tert-butyl ester (16) (1.0 g, 1.68 mmol) in THF (45 mL), HOAc (15 mL) and H$_2$O (15 mL) was added Zn dust (8.81 g, 134.7 mmol). The resulting mixture was stirred at 70° C. for 16 h, at which point the reaction was judged complete by LC/MS and TLC. The reaction was then cooled to room temperature, the reaction was filtered through a pad of celite and the solid residue was washed with DCM. The combined filtrate was concentrated in vacuo. Remaining water was removed by azeotrope with CHCl$_3$ (3×50 mL). The resulting residue was purified by column chromatography (0→50% EtOAc in Hex) to afford 636 mg of 17 (83% yield).

LC/MS: retention time 3.71 min. (ESI) calculated for $C_{26}H_{34}N_2O_5Na$: [M+Na]$^+$ 477; found 477.

tert-Butyl 5-(allyl(tert-butoxycarbonyl)amino)-1-(chloromethyl)-1,2-dihydro-3H-benzo[e]indole-3-carboxylate (18)

To a solution of tert-butyl 5-(allyl(tert-butoxycarbonyl)amino)-1-(hydroxymethyl)-1,2-dihydro-3H-benzo[e]indole-3-carboxylate (17) (1.0 g, 1.40 mmol) in DCM (5.6 mL), under Ar, was added PPh$_3$ (1.10 g, 4.20 mmol) followed by CCl$_4$ (1.22 mL, 12.6 mmol). The resulting mixture was stirred at 22° C. for 2 h, at which point the reaction was judged complete by LC/MS and TLC. The reaction was then concentrated in vacuo and resulting residue was purified by column chromatography (0→50% EtOAc in Hex) to afford 592 mg of 18 (89% yield).

LC/MS: retention time 4.42 min. (ESI) calculated for $C_{26}H_{33}ClN_2O_4Na$: [M+Na]$^+$ 495; found 495.

Allyl Protected IQB-CBI (19a)

TFA (5 mL) was precooled to 0° C. and then added to Boc-protected CBI (29 mg, 0.06 mmol). Solution was kept at 0° C. overnight and then concentrated to dryness. Residue was redissolved in anhydrous chloroform evaporated again and partitioned between saturated NaHCO$_3$ and DCM. Organic phase was dried over MgSO$_4$ and concentrated to obtain crude salt of aniline. It was dissolved in DMF (1.2 mL) and acid 11a (25 mg, 0.068 mmol) was added followed by EDC-HCl (30 mg, 0.16 mmol). Reaction mixture was stirred for 3 hr and then directly loaded onto a 15.5 g C$_{18}$ Aq Isco column and purified (5→95% ACN in H$_2$O, each containing 0.05% of AcOH). Desired fractions were lyophilized to obtain 22 mg of 19a (58% yield).

$^1$H NMR (500 MHz, CDCl$_3$) δ: 7.81 (d, J=8.3 Hz, 1H), 7.77 (s, 1H), 7.68 (d, J=8.8 Hz, 1H), 7.59 (s, 1H). 7.52 (m, 1H), 7.46 (m, 1H), 7.34 (m, 7H), 6.87 (m, 1H), 6.05 (m, 1H), 5.37 (d, J=17.1 Hz, 1H), 5.24 (d, J=10.3 Hz, 1H), 5.02 (d, J=15.1 Hz, 1H), 4.92 (m, 2H), 4.55 (d, J=15.1 Hz, 1H), 4.33 (m, 2H), 4.07 (m, 1H), 4.00 (s, 3H), 3.95 (m, 3H). 3.44 (m, 1H), 3.26 (m, 1H), 3.13 (m, 1H).

LC/MS: retention time 3.28 min. (ESI) $C_{36}H_{34}ClN_4O_4$ calculated for [M+H]$^+$ 622; found 622.

Allyl Protected IQB-CBI (19b)

Procedure as described for 19a, obtained 21 mg of 19b (45% yield).

$^1$H NMR (500 MHz, CDCl$_3$) δ: 7.81 (d, J=8.3 Hz, 1H), 7.80 (s, 1H), 7.68 (d, J=8.8 Hz, 1H), 7.54 (s, 1H). 7.49 (m, 3H), 7.31 (m, 7H), 6.94 (s, 1H), 6.05 (m, 1H), 5.39 (d, J=17.1 Hz, 1H), 5.36 (m, 1H), 5.24 (d, J=10.3 Hz, 1H), 5.02 (d, J=15.1 Hz, 1H), 4.55 (d, J=15.1 Hz, 1H), 4.54 (m, 1H), 4.31 (m, 2H), 4.07 (m, 1H), 3.98 (m, 3H), 3.94 (m, 3H). 3.41 (m, 1H), 3.26 (m, 1H), 3.18 (m, 2H), 3.13 (m, 1H).

LC/MS: retention time 3.24 min. (ESI) $C_{37}H_{36}ClN_4O_4$ calculated for [M+H]$^+$ 635; found 635.

Allyl Protected IQB-CBI (19c)

Procedure as described for 19a, obtained 20 mg of 19c (31% yield).

$^1$H NMR (500 MHz, CDCl$_3$) δ: 7.82 (d, J=8.3 Hz, 1H), 7.79 (s, 1H), 7.65 (d, J=8.8 Hz, 1H), 7.53 (s, 1H). 7.47 (m, 3H), 7.35 (m, 7H), 6.87 (s, 1H), 6.08 (m, 1H), 5.38 (d, J=17.1 Hz, 1H), 5.25 (d, J=9.1 Hz, 1H), 5.01 (d, J=10.3 Hz,

1H), 5.02 (d, J=15.1 Hz, 1H), 4.53 (d, J=15.1 Hz, 1H), 4.27 (m, 2H), 4.00 (m, 2H), 3.92 (m, 3H). 3.38 (m, 1H), 3.24 (m, 1H), 3.16 (m, 1H), 2.80 (m, 1H), 2.72 (m, 1H), 2.34 (m, 2H).

LC/MS: retention time 3.35 min. (ESI) $C_{38}H_{38}ClN_4O_4$ calculated for [M+H]$^+$ 649; found 649.

Allyl Protected IQB-CBI (19d)

Procedure as described for 19a, obtained 14 mg of 19d (15% yield).

$^1$H NMR (500 MHz, CDCl$_3$) δ 7.86-7.74 (m, 2H), 7.66 (d, J=8.3 Hz, 1H), 7.54-7.43 (m, 3H), 7.41-7.28 (m, 5H), 6.81 (d, J=1.1 Hz, 1H), 6.07 (ddt, J=16.4, 10.8, 5.4 Hz, 1H), 5.37 (dq, J=17.2, 1.7 Hz, 1H), 5.24 (ddq, J=10.3, 2.5, 1.4 Hz, 1H), 5.01 (dd, J=15.6, 1.3 Hz, 1H), 4.55 (d, J=15.5 Hz, 1H), 4.31-4.14 (m, 4H), 4.02-3.96 (m, 4H), 3.95-3.91 (m, 5H), 3.38 (td, J=10.9, 3.9 Hz, 1H), 3.33-3.06 (m, 2H), 2.78-2.65 (m Hz, 1H), 2.63-2.46 (m, 1H), 2.04-1.92 (m, 4H).

LC/MS: retention time 3.38 min. (ESI) $C_{39}H_{40}ClN_4O_4$ calculated for [M+H]$^+$ 663; found 663.

Allyl Protected IQB-CBI (19e)

Procedure as described for 19a, obtained 6 mg of 19e (12% yield).

$^1$H NMR (500 MHz, CDCl$_3$) δ 7.83 (s, 1H), 7.79 (d, J=8.5 Hz, 1H), 7.66 (d, J=8.3 Hz, 1H), 7.59-7.42 (m, 2H), 7.41-7.28 (m, 6H), 6.81 (s, 1H), 6.07 (ddd, J=16.1, 10.6, 5.3 Hz, 1H), 5.38 (dq, J=17.3, 1.7 Hz, 1H), 5.27-5.20 (m, 1H), 5.01 (d, J=15.5 Hz, 1H), 4.56 (d, J=15.5 Hz, 1H), 4.39-4.16 (m, 2H), 4.15-4.04 (m, 3H), 4.02-3.96 (m, 3H), 3.95-3.87 (m, 5H), 3.38 (t, J=10.9 Hz, 1H), 3.27 (dd, J=15.4, 5.6 Hz, 1H), 3.16 (dd, J=15.4, 4.2 Hz, 1H), 2.62 (dt, J=15.6, 7.4 Hz, 1H), 2.50 (dt, J=15.6, 7.4 Hz, 1H), 1.96 (q, J=7.2 Hz, 2H), 1.85 (q, J=7.9 Hz, 2H), 1.63 (p, J=7.9 Hz, 2H).

LC/MS: retention time 3.46 min. (ESI) $C_{40}H_{42}ClN_4O_4$ calculated for [M+H]$^+$ 677; found 677.

Synthesis of D801 (20a)

19a (22 mg, 0.04 mmol) was dissolved in anhydrous DCM (0.8 mL). Camphorsulfonic acid (6.4 mg, 0.12 mmol) and benzenesulfinic acid sodium salt (16.4 mg, 0.1 mmol) were added. Vial was flushed with Ar before adding palladium tetrakistriphenylphosphine (4.6 mg, 0.004 mmol). Reaction mixture was stirred for 30 minutes and concentrated to dryness. Residue was dissolved in DMSO (0.5 mL) and loaded directly onto 15.5 g $C_{18}$ Aq Isco column and purified (5→95% ACN in H$_2$O, each containing 0.05% of AcOH). Desired fractions were lyophilized to obtain 9 mg of 20a (39% yield).

$^1$H NMR (500 MHz, CDCl$_3$) δ: 7.88 (s, 1H), 7.80 (d, J=8.3 Hz, 1H), 7.68 (d, J=8.8 Hz, 1H), 7.59 (s, 1H). 7.52 (m, 1H), 7.46 (m, 1H), 7.34 (m, 6H), 6.87 (m, 1H), 5.02 (d, J=15.1 Hz, 1H), 4.92 (m, 2H), 4.55 (d, J=15.1 Hz, 1H), 4.33 (m, 2H), 4.07 (m, 1H), 4.00 (s, 3H), 3.95 (m, 3H). 3.44 (m, 1H), 3.26 (m, 1H), 3.13 (m, 1H).

LC/MS: retention time 2.93 min. (ESI) $C_{33}H_{30}ClN_4O_4$ calculated for [M+H]$^+$ 581; found 581.

Synthesis of D807 (20b)

Procedure as described for 20a, to obtain 2.1 mg of 20b (11% yield).

$^1$H NMR (500 MHz, CDCl$_3$) δ: 7.93. (s, 1H), 7.81 (d, J=8.3 Hz, 1H), 7.69 (d, J -8.8 Hz, 1H), 7.54 (s, 1H). 7.49 (m, 2H), 7.35 (m, 6H), 6.94 (m, 1H), 5.02 (d, J=15.1 Hz, 1H), 4.56 (d, J=15.1 Hz, 1H), 4.54 (m, 2H), 4.30 (m, 3H), 4.05 (m, 1H), 3.95 (m, 5H). 3.41 (m, 1H), 3.25 (m, 1H), 3.18 (m, 2H). 3.11 (m, 1H).

LC/MS: retention time 2.90 min. (ESI) $C_{34}H_{32}ClN_4O_{04}$ calculated for [M+H]$^+$ 595; found 595.

Synthesis of D803 (20c)

Procedure as described for 20s, to obtain 5.0 mg of 20c (26% yield).

$^1$H NMR (500 MHz, CDCl$_3$) δ: 7.94 (d, J=8.3 Hz, 1H), 7.80 (d, J=8.8 Hz, 1H), 7.67 (d, J=8.8 Hz, 1H), 7.48 (m, 4H), 7.34 (m, 6H), 6.87 (m, 1H), 5.02 (d, J=15.1 Hz, 1H), 4.56 (d, J=15.1 Hz, 1H), 4.28 (m, 4H), 4.05 (m, 1H), 3.92 (m, 5H). 3.39 (m, 1H), 3.26 (m, 1H), 3.14 (m, 1H). 2.75 (m, 2H), 2.34 (m, 2H).

LC/MS: retention time 2.98 min. (ESI) $C_{35}H_{34}ClN_4O_4$ calculated for [M+H]$^+$ 609; found 609.

Synthesis of D809 (20d)

Procedure as described for 20s, to obtain 2.0 mg of 20d (15% yield).

$^1$H NMR (500 MHz, CDCl$_3$) δ 7.92 (s, 1H), 7.79 (dd, J=8.5, 5.4 Hz, 1H), 7.66 (d, J=8.4 Hz, 1H), 7.54-7.44 (m, 3H), 7.42-7.28 (m, 5H), 6.82 (d, J=1.5 Hz, 1H), 5.01 (dd, J=15.5, 2.4 Hz, 1H), 4.56 (d, J=15.5 Hz, 1H), 4.27 (d, J=10.1 Hz, 1H), 4.19 (dt, J=13.3, 7.5 Hz, 3H), 4.12 (t, J=7.3 Hz, 2H), 4.02 (d, J=9.8 Hz, 1H), 3.97-3.82 (m, 5H), 3.39 (td, J=10.9, 3.5 Hz, 1H), 3.27 (dd, J=15.4, 5.6 Hz, 1H), 3.15 (dt, J=15.4, 3.7 Hz, 1H), 2.71-2.62 (m, 1H), 2.61-2.57 (m, 1H), 2.11-1.91 (m, J=7.1, 6.6 Hz, 4H).

LC/MS: retention time 3.03 min. (ESI) $C_{36}H_{36}ClN_4O_4$ calculated for [M+H]$^+$ 623; found 623.

Synthesis of D80S (20e)

Procedure as described for 20s, to obtain 1.7 mg of 20e (30% yield).

$^1$H NMR (500 MHz, CDCl$_3$) δ 7.94 (s, 1H), 7.79 (d, J=8.4 Hz, 1H), 7.67 (d, J=8.3 Hz, 1H), 7.53 (d, J=0.7 Hz, 1H), 7.52-7.44 (m, 2H), 7.41-7.29 (m, 5H), 6.81 (s, 1H), 5.01 (d, J=15.5 Hz, 1H), 4.56 (d, J=15.5 Hz, 1H), 4.27 (d, J=10.9 Hz, 2H), 4.23-4.16 (m, 1H), 4.15-4.05 (m, 1H), 4.01 (t, J==9.4 Hz, 1H), 3.97-3.87 (m, 5H), 3.39 (t, J=10.9 Hz, 1H), 3.27 (dd, J=15.4, 5.6 Hz, 1H), 3.16 (dd, J=15.4, 4.2 Hz, 1H), 2.68-2.55 (m, 1H), 2.55-2.43 (m, 1H), 1.97 (p, J=6.9 Hz, 2H), 1.86 (p, J 7.4 Hz, 2H), 1.63 (p, J=7.9 Hz, 2H).

LC/MS: retention time 3.10 min. (ESI) $C_{37}H_{38}ClN_4O_4$ calculated for [M+H]$^+$ 637; found 637.

Figure 3:
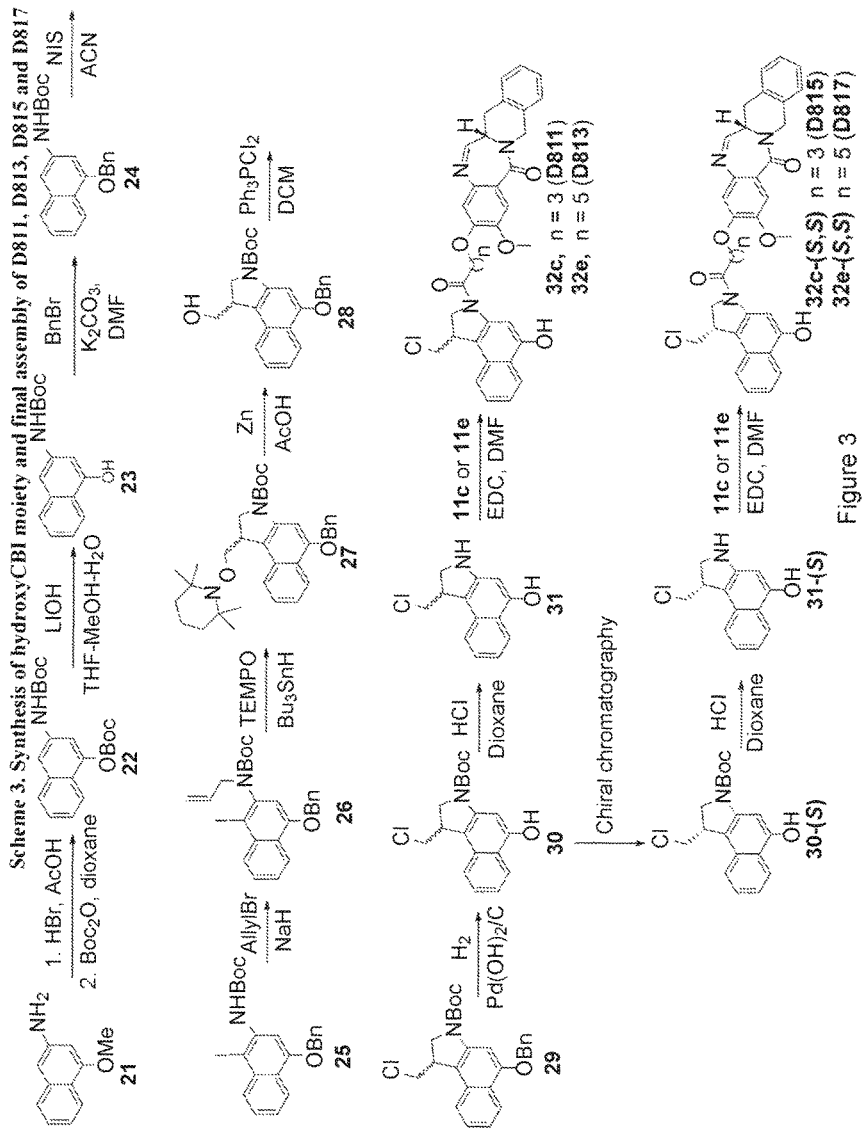
FIG. 3 shows the synthesis of a hydroxyCBI moiety and final assembly of D811, D813, D815, and D817.
Figure 4:
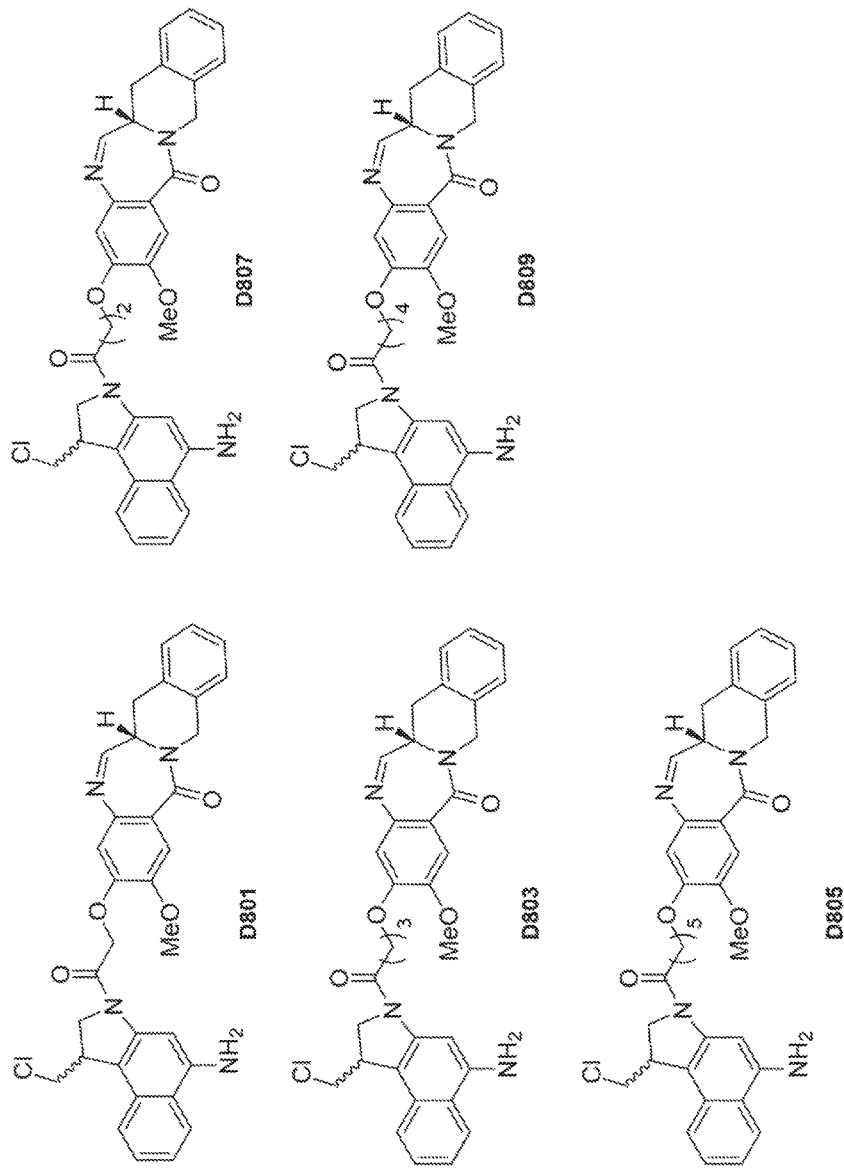
FIG. 4 shows structures of IQB-amino- and hydroxy-CBI dimer compounds.
Figure 4:
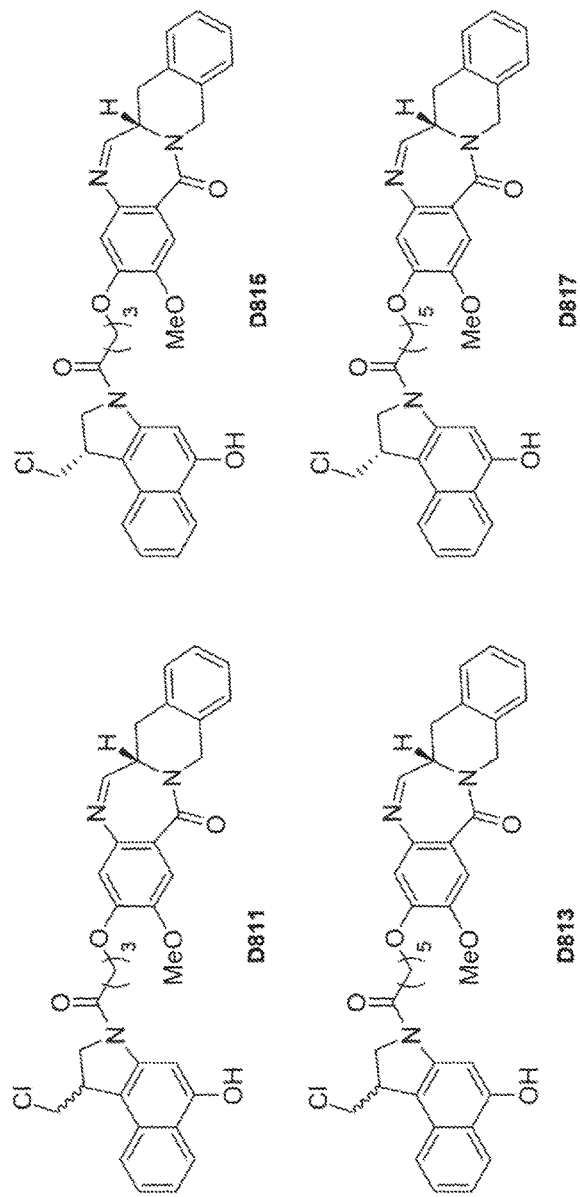

Synthesis of IQB-hydroxyCBI dimers-33c; 33c-S,S; 33e and 33e-S,S (Scheme 3, Referring to FIG. 3)

Tert-butyl (4-((tert-butoxycarbonyl)oxy)naphthalen-2-yl)carbamate (22)

4-methoxynaphthalen-2-amine (5.7 g, 33 mmol) was dissolved in mixture of AcOH and 48% HBr in water (2-3, v/v, 330 mL). The mixture was heated at 100° C. under Ar atmosphere for 24 hr and then concentrated to dryness. The residue was partitioned in EtOAc and saturated NaHCO$_3$. Organic layer was separated and concentrated to dryness. The residue was dissolved in dioxane (66 mL) and Boc$_2$O (8.6 g, 40 mmol) was added. The mixture was heated at 100° C. under Ar atmosphere for 2 hr and additional amount of Boc$_2$O (4.3 g, 20 mmol) was added. After another 2 hr reaction mixture was concentrated to dryness, dissolved in small amount of DCM and purified on 120 g a silica Teledyne Isco column (0→50% EtOAc in hexane). Evaporation of product containing fractions afforded 6.5 g of 22 (55% yield).

LC/MS: retention time 3.87 min. (ESI) $C_{20}H_{28}NO_6$ calculated for $[M+H_2O+H]^+$ 378; found 378.

Tert-butyl (4-hydroxynaphthalen-2-yl)carbamate (23)

Diboc derivative 22 (6.5 g, 18 mmol) was dissolved in THF-MeOH—$H_2O$ (3-1-1, v/v/v, 180 mL). LiOH (650 mg, 27 mmol) was added and reaction mixture was stirred for 3 hr and then concentrated to dryness. After dilution with saturated $NH_4Cl$, the product was extracted with EtOAc (2×100 mL). The organic layer was concentrated to dryness, dissolved in small amount of DCM and purified on 80 g a silica Teledyne Isco column (0→20% EtOAc in hexane). Evaporation of product containing fractions afforded 3.2 g of 23 (67% yield).

$^1$H NMR (500 MHz, $CDCl_3$) δ: 8.07 (d, J=8.3 Hz, 1H), 7.68 (d, J=8.3 Hz, 1H), 7.44 (t, J=7.3 Hz, 1H), 7.36 (m, 1H), 7.29 (s, 1H), 7.14 (br, 1H), 6.60 (br, 1H), 5.69 (br, 1H), 1.56 (s, 9H).

LC/MS: retention time 2.96 min. (ESI) $C_{15}H_{18}NO_3$ calculated for $[M+H]^+$ 260; found 260.

Tert-butyl (4-(benzyloxy)naphthalen-2-yl)carbamate (24)

To a solution of phenol 23 (3.2 g, 12 mmol), BnBr (1.75 mL, 15 mmol) in DMF (25 mL) cesium carbonate (8.1 g, 25 mmol) was added and mixture was stirred for 30 minutes Reaction mixture was diluted with water (100 mL) and extracted with diethyl ether (3×50 mL), combined organics were concentrated to dryness and purified on 80 g a silica Teledyne Isco column (0→10% EtOAc in hexane). Evaporation of product containing fractions afforded 3.2 g of 24 (77% yield).

LC/MS: retention time 3.98 min. (ESI) $C_{22}H_{24}NO_3$ calculated for $[M+H]^+$ 350; found 350.

Tert-butyl (4-(benzyloxy)-1-iodonaphthalen-2-yl) carbamate (25)

To a 24 (3.2 g, 9.2 mmol) and TsOH-$H_2O$ (50 mg) in THF-MeOH (1-1, v/v, 150 mL), NIS (2.23 g, 10 mmol) in THF (5 mL) was added dropwise at −78° C. (dry ice/acetone cooling bath). Mixture was stirred at that temperature for 1 hr and then concentrated to dryness on rotary evaporator. The residue was purified on 120 g a silica Teledyne Isco column (0→10% EtOAc in hexane). Evaporation of product containing fractions afforded 3.2 g of 25 (73% yield).

LC/MS: retention time 4.57 min. (ESI) $C_{22}H_{23}INO_3$ calculated for $[M+H]^+$ 476; found 476.

Tert-butyl allyl(4-(benzyloxy)-1-iodonaphthalen-2-yl)carbamate (26)

To solution of 25 (3.2 g, 6.7 mmol) in DMF (13 mL) sodium hydride in mineral oil (536 mg, 13.4 mmol) was added in small portions. After stirring for 5 minutes AllylBr (2.9 mL, 33 mmol) was added dropwise. After stirring for 30 minutes reaction mixture was diluted with water (100 mL) and extracted with diethyl ether (3×50 mL), combined organics were concentrated to dryness and purified on 80 g a silica Teledyne Isco column (0→10% EtOAc in hexane). Evaporation of product containing fractions afforded 3.4 g of 26 (98% yield).

$^1$H NMR (500 MHz, $CDCl_3$) δ mixture of rotamers in ratio 3:1, signals for major one are reported: 8.32 (d, J=8.3 Hz, 1H), 8.22 (d, J=8.3 Hz, 1H), 7.61 (m, 1H), 7.36 (m, 1H), 7.49 (m, 3H), 7.42 (m, 3H), 6.70 (s, 1H), 5.93 (m, 1H), 5.27 (m, 1H), 5.04 (m, 2H), 4.56 (m, 1H), 3.82 (m, 1H), 1.32 (s, 9H).

LC/MS: retention time 4.52 min. (ESI) $C_{25}H_{26}INO_3Na$ calculated for $[M+Na]^+$ 538; found 538.

Tert-butyl 5-(benzyloxy)-1-(((2,2,6,6-tetramethylpiperidin-1-yl)oxy)methyl)-1,2-dihydro-3H-benzo[e]indole-3-carboxylate (27)

To a solution of 26 (3.4 g, 6.6 mmol) in benzene (220 mL), under Ar, was added TEMPO (3.1 g, 20 mmol) and $Bu_3SnH$ (1.8 mL, 6.6 mmol). The mixture was stirred at 70° C. for 15 min, then additional amount of $Bu_3SnH$ (1 mL) and TEMPO (1 g) were added. After an additional 15 min, TEMPO (1 g) and $Bu_3SnH$ (1 mL) were added and the mixture was stirred for another 15 min, at which point more TEMPO (1 g 39 mmol) and $Bu_3SnH$ (1 mL) were added. After another 15 min, a final portion of $Bu_3SnH$ (1 mL, 19.5 mmol) and TEMPO (1 g) were added. The resulting mixture was stirred for additional 30 min at 70° C. and concentrated to dryness. The resulting residue was purified by column chromatography (0→10% EtOAc in Hex) to afford 5 g of crude 27, containing TEMPO as impurity. Used as is in the next step.

LC/MS: retention time 5.29 min. (ESI) $C_{34}H_{45}N_2O_4$ calculated for $[M+H]^+$ 545; found 545.

Tert-butyl 5-(benzyloxy)-1-(hydroxymethyl)-1,2-dihydro-3H-benzo[e]indole-3-carboxylate (28)

To solution of crude 27 (5 g, 6 mmol) in AcOH-THF-$H_2O$ (3-1-1, v/v/v, 120 mL) Zn powder (4.7 g, 72 mmol) was added in small portions. The mixture was stirred at 80° C. for 3 hr and then concentrated to dryness. Residue was carefully quenched with saturated $NaHCO_3$ and extracted with diethyl ether (2×100 mL). Organic solution was concentrated to dryness and purified on 80 g a silica Teledyne Isco column (0→60%/EtOAc in hexane). Evaporation of product containing fractions afforded 1.69 g of 28 (63% yield over 2 steps).

$^1$H NMR (500 MHz, $CDCl_3$) δ: 8.30 (d, J=8.3 Hz, 1H), 7.92 (br, 1H), 7.72 (d, J=8.3 Hz, 1H), 7.55 (m, 2H), 7.48 (m, 1H), 7.44 (m, 2H), 7.34 (m, 2H), 5.28 (br s, 2H), 4.23 (m, 1H), 4.14 (m, 1H), 3.96 (m, 1H), 3.86 (m, 1H), 3.79 (m, 1H), 1.61 (s, 9H).

LC/MS: retention time 3.77 min. (ESI) $C_{25}H_{28}NO_4$ calculated for $[M+H]^+$ 406; found 406.

Tert-butyl 5-(benzyloxy)-1-(chloromethyl)-1,2-dihydro-3H-benzo[e]indole-3-carboxylate (29)

Alcohol 28 (406 mg, 1 mmol) was dissolved in anhydrous DCM (10 mL) and $Ph_3PCl_2$ (500 mg, 1.5 mmol) was added at once. After stirring for 1 hr reaction mixture was quenched with saturated $NaHCO_3$ and extracted with chloroform. Combined organics were dried over $MgSO4$ and concentrated. The residue was purified 12 g a silica Teledyne Isco column (0→50% EtOAc in hexane). Evaporation of product containing fractions afforded 230 g of 29 (54% yield).

¹H NMR (500 MHz, CDCl₃) δ: 8.32 (d, J=8.79 Hz, 1H), 7.90 (br, 1H), 7.66 (d, J=8.30 Hz, 1H), 7.55 (m, 3H), 7.46 (t, J=7.57 Hz, 2H), 7.37 (m, 2H), 5.30 (s, 2H), 4.28 (br s, 1H), 4.15 (t, J=10.50 Hz, 1H), 3.98 (m, 2H), 3.46 (t, J=10.50 Hz, 1H), 1.64 (s, 9H).

LC/MS: retention time 4.50 min. (ESI) $C_{25}H_{27}ClNO_3$ calculated for $[M+H]^+$ 424; found 424.

Tert-butyl 1-(chloromethyl)-5-hydroxy-1,2-dihydro-3H-benzo[e]indole-3-carboxylate (30) and chiral separation to (30-(S))

Flask containing solution of 29 (232 mg, 0.55 mmol) in EtOAc (6 mL) was flushed with Ar and Pd(OH)₂/C (10% by weight, 50 mg) was added. Hydrogen (balloon) was bubbled through solution for 24 hr and then reaction mixture was filtered off through celite, concentrated and purified on 12 g silica Teledyne Isco column (0→50% EtOAc in hexane). Evaporation of product containing fractions afforded 145 mg of 30 (78% yield).

Racemic 30 was dissolved in 5 mL hexane-IPA (9-1, v/v, 5 mL) and injected in 1 mL portions on chiral HPLC with OD-H column (20×250 mm, 5 μm), 25 mL/min, 0→5% IPA in hexane over 20 minutes. $t_r$(30–(R))=12 min; $t_r$(30–(S)) =14 min (*J. Am. Chem. Soc.* 1994, 116, 7996-8006). Fractions containing desired enantiomer were combined and concentrated to dryness to afford 51 mg of 30-(S).

¹H NMR (500 MHz, CDCl₃) δ: 8.22 (d, J=8.20 Hz, 1H), 7.82 (br s, 1H), 7.64 (d, J=8.20 Hz, 1H), 7.50 (m, 1H), 7.34 (ddd, J=8.34, 6.88, 1.17 Hz, 2H), 4.26 (m, 1H), 4.14 (m, 1H), 3.96 (m, 2H), 3.43 (m, 1H), 1.61 (m, 9H).

LC/MS: retention time 3.55 min. (ESI) $C_{18}H_{21}ClNO_3$ calculated for $[M+H]^+$ 334; found 334.

Synthesis of D811 (32c)

(6aS)-3-(4-(1-(chloromethyl)-5-hydroxy-1,2-dihydro-3H-benzo[e]indol-3-yl)-4-ozobutoxy)-2-methoxy-7,12-dihydrobenzo[5,6][1,4]diazepino[1,2-b]isoquinolin-14(6aH) one (32c/D811)

4 M HCl in dioxane (1 mL) was added to Boc-protected CBI racemic 30 (15 mg, 0.03 mmol). Solution was kept at rt for 2 hr and then concentrated to dryness to afford hydrochloride of 31. Residue was redissolved in anhydrous chloroform (2 mL) evaporated again, procedure was repeated twice. Then it was dissolved in DMF (0.8 mL) and acid 11e (15 mg, 0.039 mmol) was added followed by EDC-HCl (16 mg, 0.09 mmol). Reaction mixture was stirred for 1 hr and then directly loaded onto a 15.5 g $C_{18}$ Aq Isco column and purified (5→95% ACN in H₂O, each containing 0.05% of AcOH). Desired fractions were lyophilized to obtain 2.5 mg of 32c (12% yield).

¹H NMR (500 MHz, CDCl₃) δ: 8.26 (d, J=8.30 Hz, 1H), 8.23 (s, 1H), 8.17 (s, 1H), 7.51 (m, 3H), 7.33 (m, 5H), 6.88 (m, 1H), 4.98 (d, J=15.1 Hz, 1H), 4.53 (d, J=15.1 Hz, 1H), 4.28 (m, 4H), 4.04 (m, 2H), 3.95 (m, 2H), 3.86 (m, 4H), 3.41 (m, 1H), 3.18 (m, 1H), 3.07 (m, 1H), 2.84 (m, 1H), 2.40 (m, 2H).

LC/MS: retention time 3.07 min. (ESI) $C_{35}H_{33}ClN_3O_5$ calculated for $[M+H]^+$ 610; found 610.

Synthesis of D813 (32e)

(6aS)-3-((6-(1-(chloromethyl)-5-hydroxy-1,2-dihydro-3H-benzo[e]indol-3-yl)-6-oxohexyl)oxy)-2-methoxy-7,12-dihydrobenzo[5,6][1,4]diazepino[1,2-b]isoquinolin-14(6aH)-one (32e/D813)

Procedure as described for 32c but staring with 11e. Obtained 3.0 mg of 32e (14% yield).

¹H NMR (500 MHz, CDCl₃) δ: 8.26 (d, J=8.30 Hz, 1H), 7.65 (m, 1H), 7.53 (m, 3H), 7.33 (m, 5H), 6.83 (m, 1H), 5.02 (d, J=15.1 Hz, 1H), 4.56 (d, J=15.1 Hz, 1H), 4.30 (m, 2H), 4.10 (m, 3H), 3.90 (m, 4H), 3.42 (m, 1H), 3.25 (m, 1H), 3.14 (m, 1H), 3.07 (m, 1H), 2.66 (m, 1H), 2.59 (m, 1H), 2.84 (m, 1H), 1.99 (m, 2H), 1.92 (m, 2H).

LC/MS: retention time 3.34 min. (ESI) $C_{37}H_{37}ClN_3O_5$ calculated for $[M+H]^+$ 638; found 638.

Synthesis of D815 (32c-S,S)

(S)-3-(4-((S)-1-(chloromethyl)-5-hydroxy-1,2-dihydro-3H-benzo[e]indol-3-yl-4-oxobutoxy)-2-methoxy-7,12-dihydrobenzo[5,6][1,4]diazepino[1,2-b]isoquinolin-14(6aH)-one (32c-(S,S))

Procedure as described for 32c but staring with 11c and 30-(S). Obtained 3.3 mg (16% yield).

¹H NMR (500 MHz, CDCl₃) δ: 8.26 (d, J=8.30 Hz, 1H), 8.20 (s, 1H), 7.64 (m, 1H), 7.51 (m, 3H), 7.33 (m, 5H), 6.87 (s, 1H), 5.00 (d, J=15.1 Hz, 1H), 4.54 (d, J=15.1 Hz, 1H), 4.27 (m, 4H), 4.02 (m, 1H), 3.92 (m, 2H), 3.86 (m, 3H), 3.78 (m, 1H), 3.71 (m, 1H), 3.65 (m, 1H), 3.39 (m, 1H), 3.19 (m, 1H), 3.08 (m, 1H), 2.88 (m, 1H), 2.78 (m, 1H), 2.40 (m, 2H).

LC/MS: retention time 3.07 min. (ESI) $C_{35}H_{33}ClN_3O_5$ calculated for $[M+H]^+$ 610; found 610.

Synthesis of D817 (32e-S,S)

(S)-3-((6-(((S)-1-(chloromethyl)-5-hydroxy-1,2-dihydro-3H-benzo[e]indol-3-yl)-6-oxohexyl)oxy)-2-methoxy-7,12-dihydrobenzo[5,6][1,4]diazepino[1,2-b]isoquinolin-14(6aH)-one (32e-(S,S))

Procedure as described for 32c but staring with 11e and 30-(S). Obtained 2.5 mg (12% yield).

¹H NMR (500 MHz, CDCl₃) δ: 8.26 (d, J=8.30 Hz, 1H), 8.23 (m, 1H), 7.65 (m, 1H), 7.53 (m, 3H), 7.33 (m, 5H), 6.85 (s, 1H), 5.02 (d, J=15.1 Hz, 1H), 4.57 (d, J=15.1 Hz, 1H), 4.30 (m, 2H), 4.14 (m, 2H), 4.04 (m, 1H), 3.90 (m, 6H), 3.41 (m, 1H), 3.26 (m, 1H), 3.16 (m, 1H), 2.66 (m, 1H), 2.59 (m, 1H), 1.99 (m, 2H), 1.92 (m, 2H), 1.65 (m, 2H).

LC/MS: retention time 3.34 min. (ESI) $C_{37}H_{37}ClN_3O_5$ calculated for $[M+H]^+$ 638; found 638.

Example 2: Experimental Protocols for the Synthesis of IQB-CBI with Various Linking Groups (Schemes 5 and 6, Referring to FIGS. 5 and 6)

Figure 5:
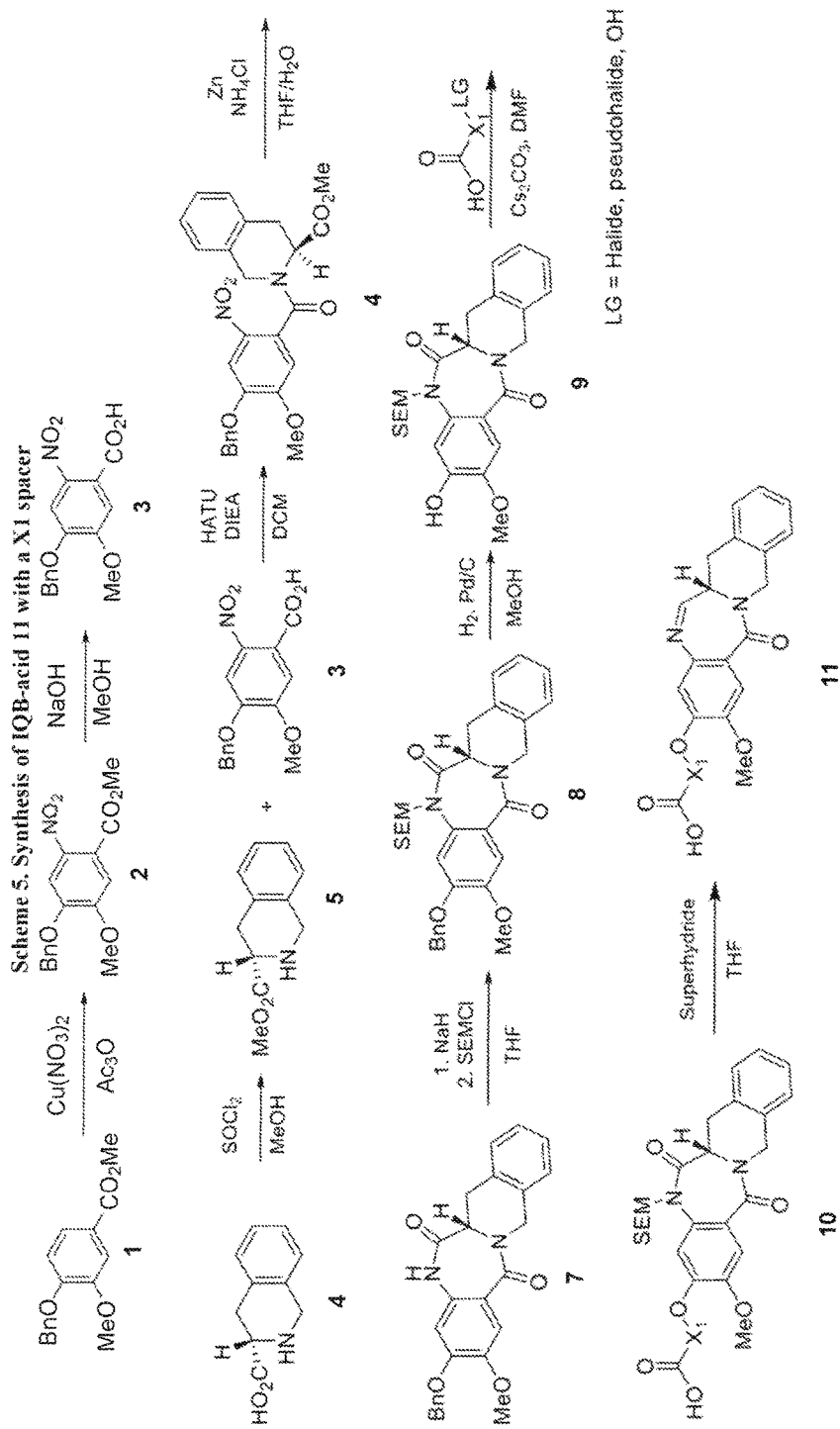
FIG. 5 shows the synthesis of an IQB-acid 11 in which the spacer group X1 is selected from the X1 spacers disclosed, for example, in Table I.
Figure 6:
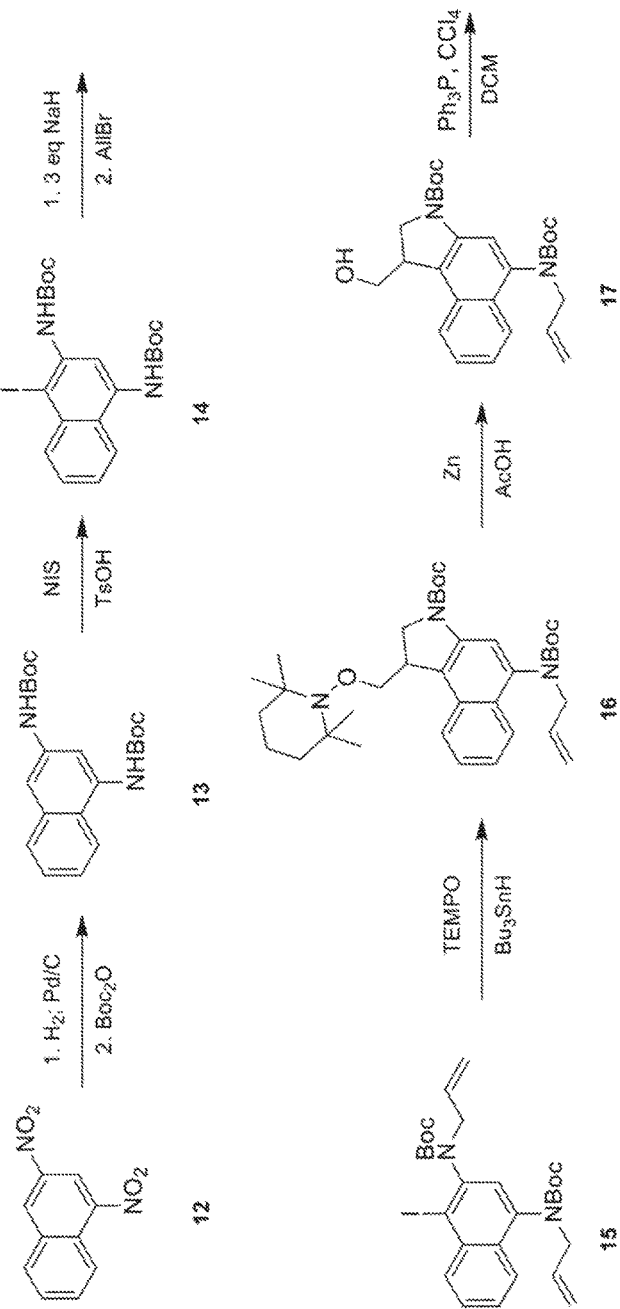
FIG. 6 shows the synthesis of a CBI moiety and assembly of IQB-CBI dimer variant in which the X1 spacer is selected from the X1 spacers disclosed, for example, in Table I.
Figure 6:
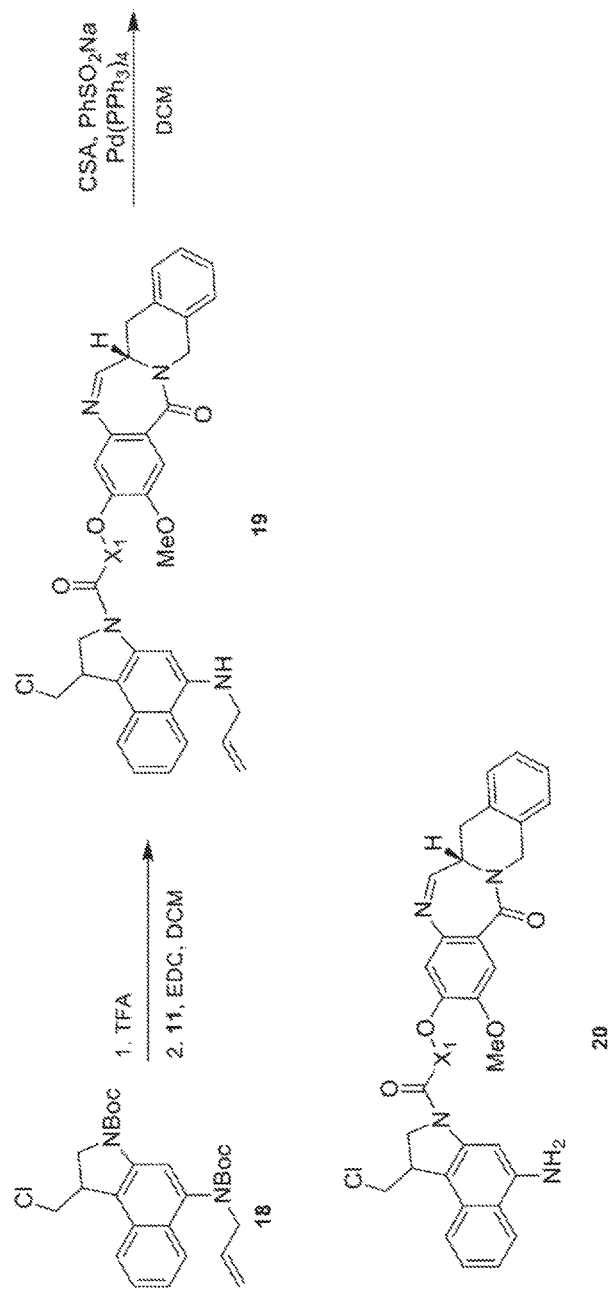

The synthesis protocol used to produce CLT-D801 can be modified to introduce various spacer groups between the IQB moiety and the CBI moiety. Referring to FIGS. 5 and 6, the protocol can proceed in an identical fashion, with a modification introduced at the step between compounds 9 and 10. More specifically, rather than 2-bromoacetic acid, a carboxylic acid incorporating a moiety X1, as described herein, in used.

Example 3: Cytotoxicity of IQB-aminoCBI and IQB-hydroxyCBI Dimers

Cytotoxicity of D801, D803, D05, D807, D809, D811, D813, D815 and D817 were tested against AML2 and HL60 cell lines. Results are shown in Table 1. Cell killing assay was performed after 3-day incubation with various IQB-CBI dimers.

TABLE 1

| IC50 pg/mL | D211 | D801 | D803 | D805 | D807 | D809 | D811 | D813 | D815 | D817 |
|---|---|---|---|---|---|---|---|---|---|---|
| AML2 | 0.19 | 16.2 | 14.6 | 52.2 | 132 | 286 | 0.13 | 0.28 | 0.07 | 0.13 |
| HL60 | 0.47 | 44.5 | 40.6 | 142.6 | 557 | 1850 | 0.29 | 0.72 | 0.12 | 0.19 |

General Methods:

$^1$H NMR spectra were recorded on a Varian Inova 300 or 500 MHz NMR instrument. Chromatographic purities were determined on an Agilent 1200 Series, 1100 Series or 6130 Series LC/MS system using a Merck Chromolith RP-18e analytical HPLC column (monolithic, 50×2 mm) and the following analytical HPLC method: injection volume 5 μL; flow rate 1 mL/min; 5→95% acetonitrile in water with 0.05% AcOH over 5 mins; Agilent diode array detector at λ=254, 220 or 195 nm; room temperature.

Figure 7:
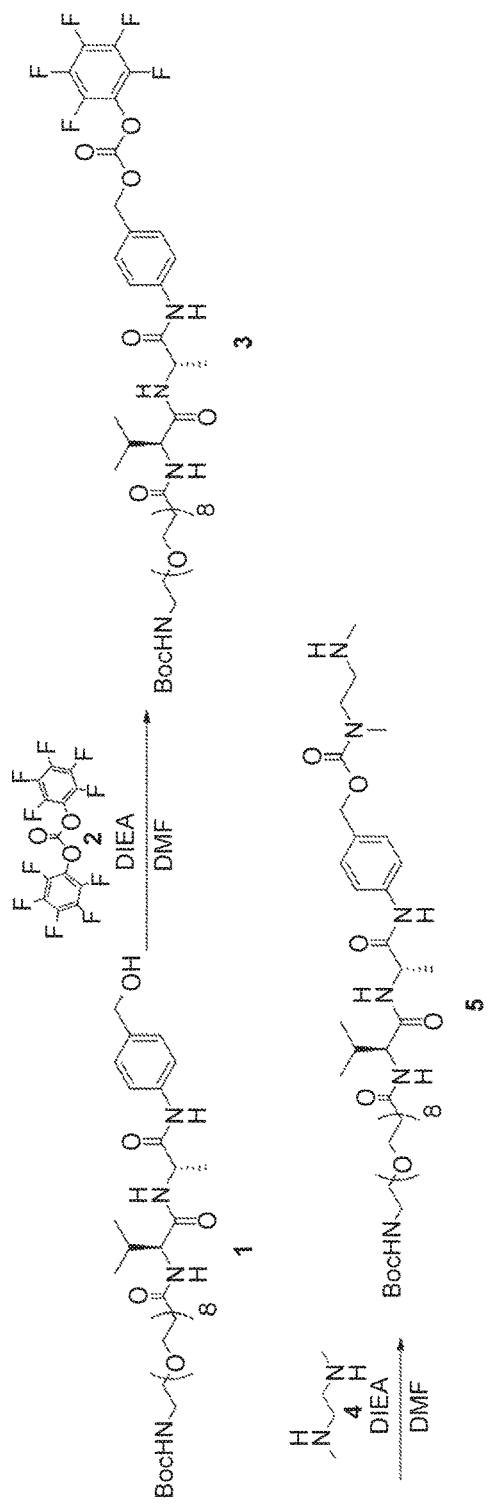
FIG. 7 shows synthesis of the linkers L.

1.0 Synthesis of Linkers (Scheme 7) (Referring to FIG. 7)

1.1 t-boc-N-amido-dPEG®$_8$-Val-Ala-4-aminobenzyl-pentafluorophenyl carbonate (3)

To an Ar purged solution of t-boc-N-amido-dPEG®$_8$-Val-Ala-4-aminobenzyl-alcohol (1) (350 mg, 0.428 mmol) in DMF (2.1 mL), added DIEA (149 μL, 0.856 mmol), followed by bis-(pentafluorophenyl)-carbonate (253 mg, 0.643 mmol). The reaction was then stirred at 22° C. for 45 min. The resulting reaction mixture was then directly loaded and purified via reverse phase column chromatography (0→100% ACN in H$_2$O, each containing 0.05% AcOH) and desired fractions lyophilized to afford (3) as a yellow foam (347 mg, 79% yield, 0.338 mmol).

$^1$H NMR (500 MHz, CDCl$_3$): δ 8.69 (bs, 1H), 7.78 (d, J=8.4 Hz, 2H), 7.36 (d, J=8.4 Hz, 2H), 6.98 (bs, 1H), 6.86 (bs, 1H), 5.27 (s, 2H), 5.02 (bs, 1H), 4.70-4.64 (m, 1H), 4.20 (t, J=5.9 Hz, 1H), 3.86 (td, J=9.9, 2.9 Hz, 1H), 3.69-3.61 (m, 29H), 3.53 (t, J=4.8 Hz, 2H), 3.31 (bd, J=4.3 Hz, 2H), 2.70-2.65 (m, 1H), 2.49-2.45 (m, 1H), 2.30 (dq, J=12.7, 6.4 Hz, 1H), 1.45 (d, J=11.5 Hz, 3H), 1.44 (s, 9H), 1.01 (dd, J=15.0, 6.8 Hz, 6H).

LC/MS: retention time 2.98 min. (ESI) C$_{46}$H$_{67}$F$_5$N$_4$O$_{16}$Na: [M+Na]$^+$ 1049; found 1049.

1.2 t-boc-N-amido-dPEG®$_8$-Val-Ala-4-aminobenzyl-N$^1$,N$^2$-dimethylethane-1,2-diamine Carbamate (5)

To a solution of N,N$^2$-dimethylethane-1,2-diamine (4) (142 μL, 1.32 mmol) in DMF (0.33 mL) under Ar, was added a crude solution of (5) reaction mixture (described above) (0.0661 mmol) in 0.33 mL DMF, dropwise. An additional 100 μL of DMF was used to wash the transfer flask and added to the reaction mixture to ensure a complete transfer of (3) to the reaction mixture. The resulting mixture was then stirred at 22° C. for 1 h. The reaction mixture was diluted with 0.5 mL H$_2$O then directly loaded and purified via reverse phase column chromatography (0→100% ACN in H$_2$O, each containing 0.05% AcOH) and desired fractions lyophilized to afford (5) as an off-white foam (37.1 mg, 60% yield, 0.0398 mmol).

$^1$H NMR (500 MHz, CDCl$_3$): δ 8.56 (bs, 1H), 7.68 (d, J=8.3 Hz, 2H), 7.30 (d, J=8.3 Hz, 2H), 6.95 (bs, 1H), 6.81 (bs, 1H), 5.04 (s, 2H), 4.65 (quintet, J=7.4 Hz, 1H), 4.20 (t, J=6.3 Hz, 1H), 3.88-3.83 (m, 1H), 3.70-3.59 (m, 29H), 3.53 (t, J=5.0 Hz, 2H), 3.43-3.37 (m, 2H), 3.31-3.30 (m, 2H), 2.94 (s, 3H), 2.80-2.78 (m, 1H), 2.73-2.71 (m, 1H), 2.68-2.63 (m, 1H), 2.50-2.45 (m, 4H), 2.40 (s, 2H), 2.29 (dt, J=7.1, 6.3 Hz, 1H), 1.45 (d, J=7.4 Hz, 3H), 1.44 (s, 9H), 1.00 (dd, J=15.1, 6.9 Hz, 6H).

LC/MS: retention time 2.15 min. (ESI) C$_{44}$H$_{79}$N$_6$O$_{15}$: [M+H]$^+$ 932; found 932.

Figure 8:
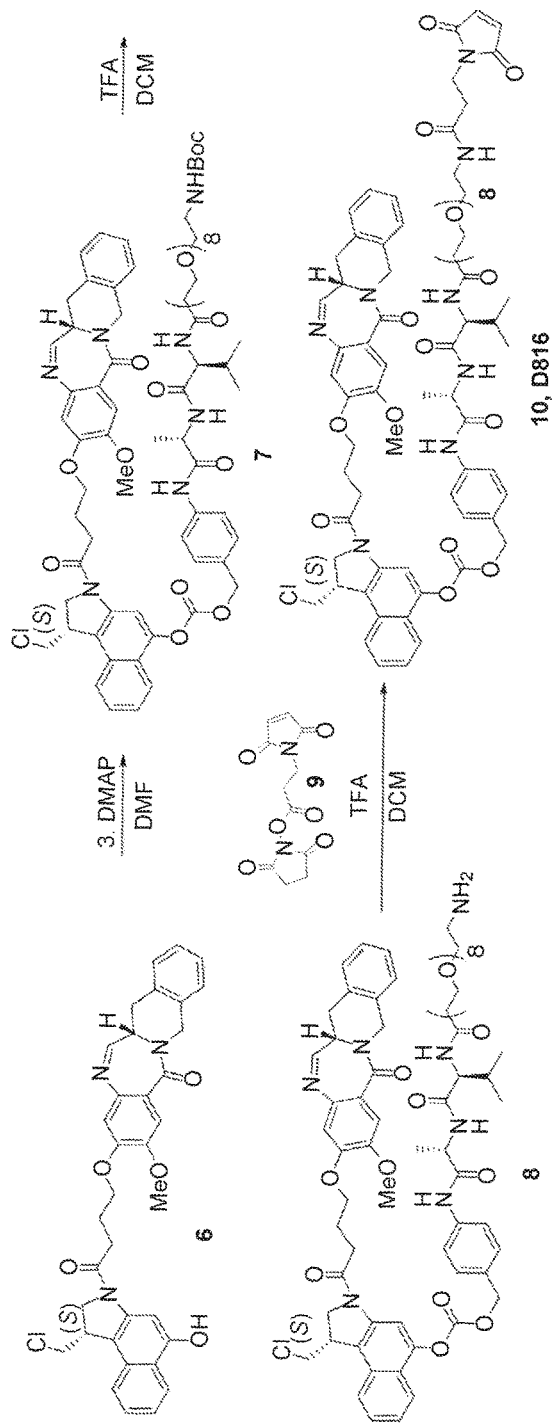
FIG. 8 shows synthesis of Carbonate D816.

2.0 Synthesis of Carbonate D816 (Scheme 8) (Referring to FIG. 8)

2.1 t-boc-N-amido-dPEG®$_8$-Val-Ala-4-aminobenzyl Carbonate of OxoDuocarmycin-IQB-3C spacer (7)

To a solution of (6aS)-3-(4-(1-(chloromethyl)-5-hydroxy-1,2-dihydro-3H-benzo[e]indol-3-yl)-4-oxobutoxy)-2-methoxy-7,12-dihydrobenzo[5,6][1,4]diazepino[1,2-b]isoquinolin-14(6aH)-one (6) (20.3 mg, 0.333 mmol) in DMF (1.1 mL), under Ar, added t-boc-N-amido-dPEG®$_8$-Val-Ala-4-aminobenzyl-pentafluorophenyl carbonate (3) (34.2 mg, 0.0333 mmol) and DMAP (10.2 mg, 0.0833 mmol). The resulting mixture was stirred at 22° C. for 1 h. The resulting reaction mixture was then directly loaded and purified via reverse phase column chromatography (0→100% ACN in H$_2$O, each containing 0.05% AcOH) and desired fractions lyophilized to afford (7) as a white solid (29.6 mg, 61% yield, 0.0204 mmol).

LC/MS: retention time 3.01 min. (ESI) C$_{75}$H$_{99}$ClN$_7$O$_{20}$: [M+H]$^+$ 1452; found 1452.

2.2 Amino-dPEG®$_8$-Val-Ala-4-aminobenzyl Carbonate of OxoDuocarmycin-IQB-3C Spacer (8)

To t-boc-N-amido-dPEG®$_8$-Val-Ala-4-aminobenzyl carbonate of OxoDuocarmycin-IQB-3C spacer (7) (29.6 mg, 0.0204 mmol), under Ar, added a solution on 10:1 DCM/TFA solution (1.0 mL). The resulting mixture was stirred at 22° C. for 30 min. The resulting reaction mixture was then directly loaded and purified via reverse phase column chromatography (0→100% ACN in H$_2$O, each containing 0.05% AcOH) and desired fractions lyophilized to afford (8) as a white solid (11.8 mg, 44% yield, 0.00872 mmol).

LC/MS: retention time min. (ESI) C$_{70}$H$_{91}$ClN$_7$O$_{18}$: [M+H]$^+$ 1352; found 1352.

2.3 Maleimido PROPIONATE-Amido-dPEG®$_8$-Val-Ala-4-Aminobenzyl Carbonate of OxoDuocarmycin-IQB-3C Spacer, (D816) (10)

To a solution of amino-dPEG®$_8$-Val-Ala-4-aminobenzyl carbonate of OxoDuocarmycin-IQB-3C spacer (8) (11.8 mg, 0.00872 mmol) in DCM (0.5 mL) under Ar, was added TEA (12.2 μL, 0.0872 mmol), and maleimido propionate NHS ester (8). The resulting mixture was stirred at 22° C. for 1 h. The reaction mixture was then concentrated, dissolved in DMSO and directly loaded and purified via reverse phase column chromatography (0→100% ACN in H$_2$O, each containing 0.05% AcOH) and desired fractions lyophilized to afford (10) as a white solid (6.8 mg, 52% yield, 0.00452 mmol).

LC/MS: retention time 2.74 min. (ESI) $C_{77}H_{96}ClN_8O_{21}$: [M+H]$^+$ 1503; found 1503.

Figure 9:
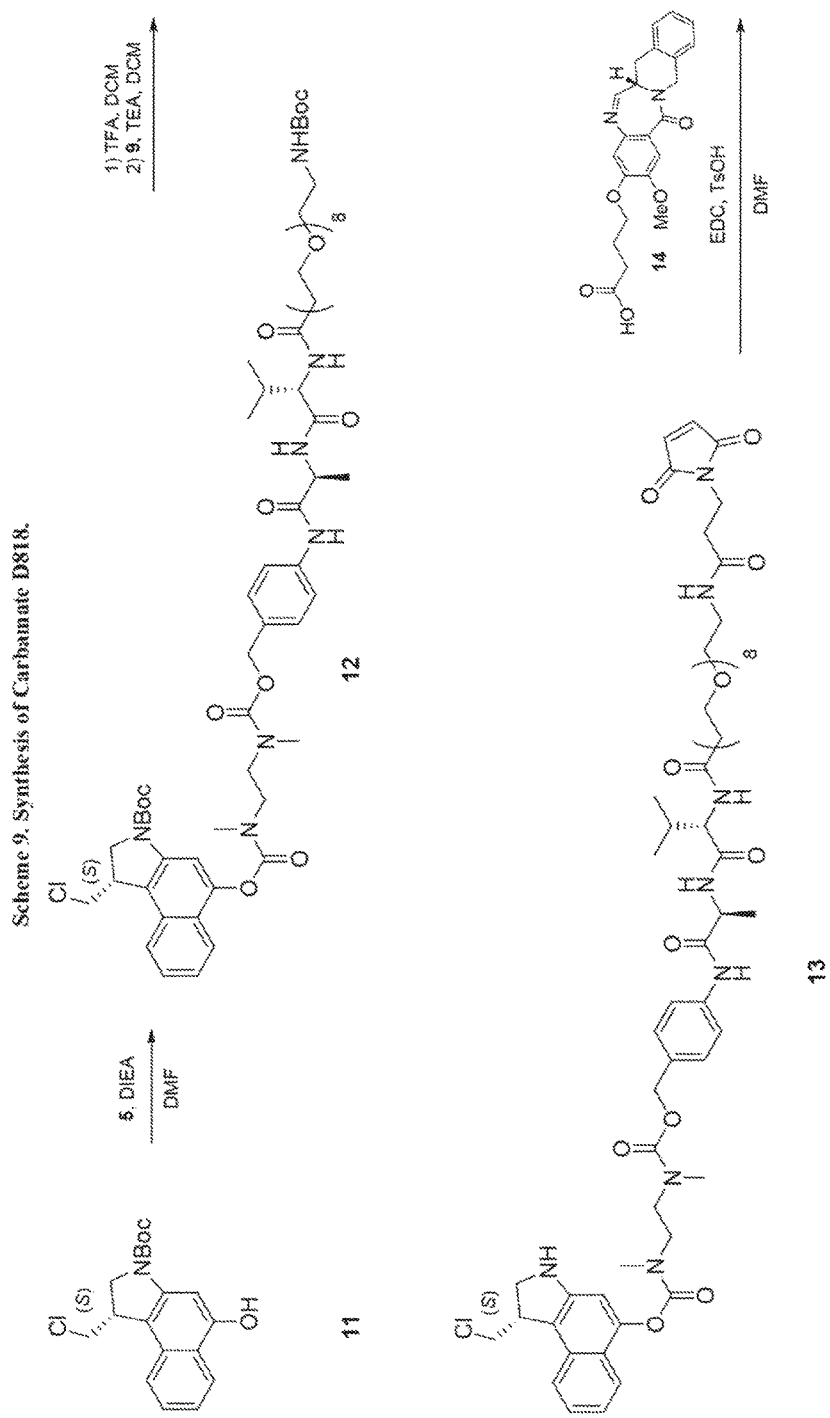
FIG. 9 shows synthesis of Carbamate D818.
Figure 9:
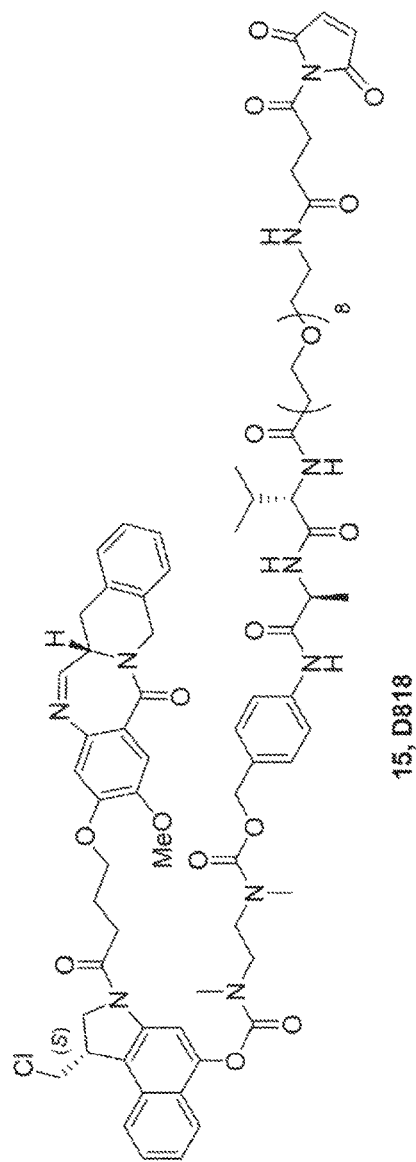

3.0 Synthesis of Carbamate D818 (Scheme 9) (Referring to FIG. 9)

3.1 t-boc-N-amido-dPEG®$_8$-Val-Ala-4-aminobenzyl Dicarbamate of Dimethyldiamine and OxoDuocarmycin-IQB-3C Spacer (12)

To a solution of tert-butyl (S)-1-(chloromethyl)-5-hydroxy-1,2-dihydro-3H-benzo[e]indole-3-carboxylate (11) (83 mg, 0.25 mmol) in ACN (1.3 mL), under Ar, added p-nitrophenoxychloroformate (55 mg, 0.28 mmol) and DIEA (0.112 mL, 0.65 mmol). The resulting mixture was stirred at 22° C. for 1 h and 5 (200 mg, 0.21 mmol) was added. The reaction mixture was stirred for 30 minutes was then directly loaded and purified via reverse phase column chromatography (0→100% ACN in H$_2$O, each containing 0.05% AcOH) and desired fractions lyophilized to afford (12) as a white solid (161 mg, 58% yield).

LC/MS: retention time 3.79 min. (ESI) $C_{63}H_{98}ClN_7O_{20}$: [M+H$_2$O+H]$^+$ 1308; found 1308.

3.2 Maleimido Propionate-Amido-dPEG®$_8$-Val-Ala-4-Aminobenzyl Dicarbamate of Dimethyldiamine and OxoDuocarmycin-IQB-3C Spacer (13)

To 12 (161 mg, 0.125 mmol), under Ar, added a solution on 10:1 DCM/TFA solution (1.0 mL). The resulting mixture was stirred at 22° C. for 30 min. The resulting reaction mixture was then directly loaded and purified via reverse phase column chromatography (0→100% ACN in H$_2$O, each containing 0.05% AcOH) and desired fractions lyophilized to afford free amine intermediate.

To a solution of deprotected amine (42 mg, 0.0382 mmol) in DCM (1.5 mL) under Ar, was added DIEA (13 μL, 0.076 mmol), and maleimido propionate NHS ester (15 mg, 0.057 mmol). The resulting mixture was stirred at 22° C. for 1 h. The reaction mixture was then concentrated, dissolved in DMSO and directly loaded and purified via reverse phase column chromatography (0→100% ACN in H$_2$O, each containing 0.05% AcOH) and desired fractions lyophilized to afford (13) as a white solid (38 mg, 81% yield).

LC/MS: retention time 2.87 min. (ESI) $C_{60}H_{86}ClN_8O_{18}$: [M+H]$^+$ 1241; found 1241.

3.3 (S)-1-(chloromethyl)-3-(4-(((S)-2-methoxy-4-oxo-6a,7,12,14-tetrahydrobenzo[5,6]-[1,4]diazepino[,2-b]isoquinolin-3-yl)oxy)butanoyl)-2,3-dihydro-1H-benzo[e]indol-5-yl (4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl) ethane-1,2-diylbis(methylcarbamate) (D818) (15)

To 13 (11 mg, 0.009 mmol) in anhydrous DMF (0.1 mL) and IQB acid (14) (4.3 mg, 0.011 mmol), pTsOH (1 mg, 0.005 mmol) and EDC.HCl (6.2 mg, 0.032 mmol) were added to the reaction. The resulting mixture was stirred at 22° C. for 10 min, then directly loaded and purified via reverse phase column chromatography (0→100% ACN in H$_2$O, each containing 0.05% AcOH) and product containing fractions were lyophilized then repurified on EZ Prep (Gemini 30×150 mm column) (5→95% ACN in H$_2$O, each containing 0.05% AcOH) to afford (15) as a white solid (1.6 mg, 11% yield).

LC/MS: retention time 2.64 min. (ESI) $C_{82}H_{106}ClN_{10}O_{22}$: [M+H]$^+$ 1618; found 1618.

Figure 10:
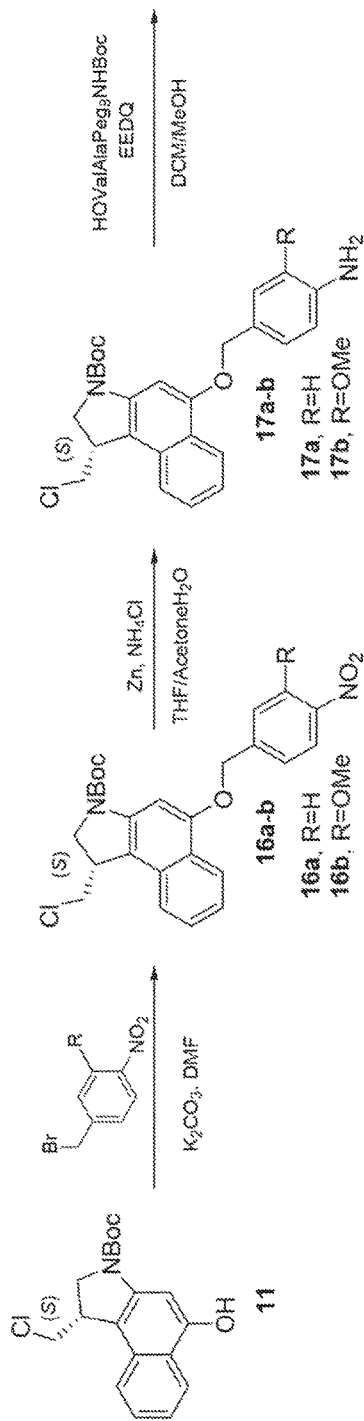
FIG. 10 shows synthesis of ether derivatives (D820 and D820b.
Figure 10:
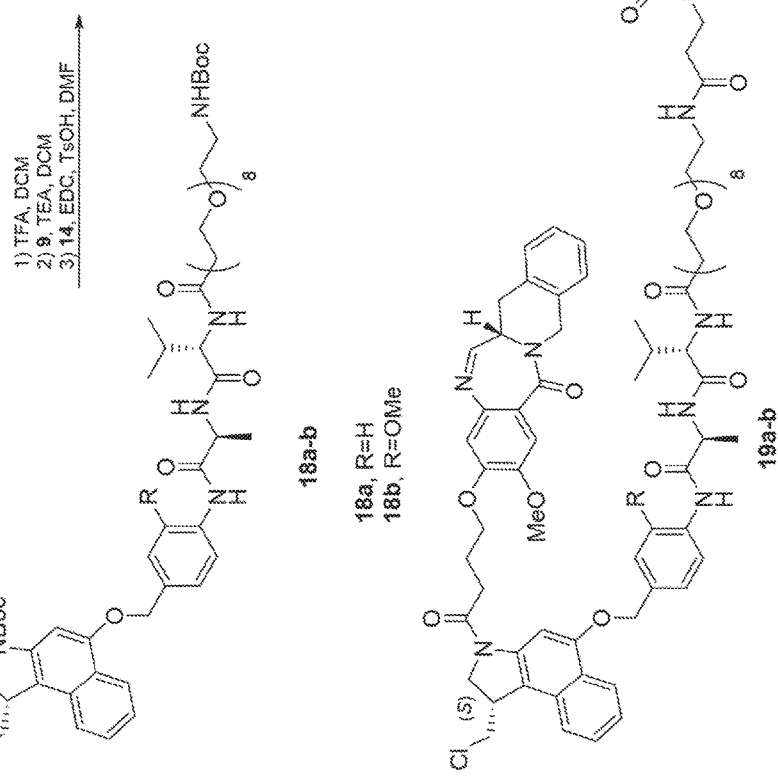

4.0 Synthesis of Ether Linked Derivatives (Scheme 10) (Referring to FIG. 10)

4.1a t-Butyl (S)-1-(chloromethyl)-5-((4-nitrobenzyl)oxy)-1,2-dihydro-3H-benzo[e]indole-3-carboxylate (16a)

To a solution of t-butyl (S)-1-(chloromethyl)-5-hydroxy-1,2-dihydro-3H-benzo[e]indole-3-carboxylate (11) (200 mg, 0.599 mmol) in anhydrous DMF (1.20 mL), under Ar, was added 4-nitrobenzyl bromide (518 mg, 2.40 mmol) and K$_2$CO$_3$ (585 mg, 1.80 mmol). The resulting mixture was stirred at 22° C. for 2 h. The reaction mixture was then partitioned between EtOAc and H$_2$O, and extracted with EtOAc (3×20 mL). The combined organics were washed with H$_2$O (4×20 mL), dried over MgSO$_4$, filtered and concentrated. The crude residue was purified via column chromatography (0→10% EtOAc in Hexanes) to afford the desired product (16a) as a yellow solid (208 mg, 74% yield, 0.443 mmol).

$^1$H NMR (500 MHz, CDCl$_3$): δ 8.29 (t, J=7.5 Hz, 3H), 7.86 (bs, 1H), 7.73 (d, J=7.9 Hz, 2H), 7.67 (d, J=8.6 Hz, 1H), 7.54 (t, J=7.4 Hz, 1H), 7.40-7.37 (m, 1H), 5.39 (s, 2H), 4.26 (bd, J=10.3 Hz, 1H), 4.14 (t, J=10.0 Hz, 1H), 3.99 (t, J=9.8 Hz, 1H), 3.94 (d, J=9.6 Hz, 1H), 3.45 (t, J=10.6 Hz, 1H), 1.60 (s, 9H).

LC/MS: retention time 3.93 min. (ESI) $C_{25}H_{26}ClN_2O_5$: [M+H]$^+$ 469; found 469.

4.1b t-Butyl (S)-1-(chloromethyl)-5-((3-methoxy-4-nitrobenzyl)oxy)-1,2-dihydro-3H-benzo[e]indole-3-carboxylate (16b)

OxoDuocarmycin 16b was synthesized according to the same procedure as 16a but starting with 3-methoxy-4-nitro benzyl bromide.

$^1$H NMR (500 MHz, CDCl$_3$) δ: 8.29 (d, J=7.5 Hz, 1H), 7.92 (d, J=7.9 Hz, 2H), 7.68 (d, J=8.6 Hz, 1H), 7.55 (t, J=7.4 Hz, 1H), 7.40-7.37 (m, 1H), 7.30 (s, 1H), 7.22 (d, J=7.5 Hz, 1H), 5.34 (s, 2H), 4.26 (bd, J=10.3 Hz, 1H), 4.15 (t, J=10.0 Hz, 1H), 4.02 (s, 3H), 3.96 (t, J=9.8 Hz, 1H), 3.93 (d, J=9.6 Hz, 1H), 3.46 (t, J=10.6 Hz, 1H), 1.61 (s, 9H).

LC/MS: retention time 3.93 min. (ESI) $C_{26}H_{27}ClN_2O_6Na$: [M+Na]$^+$ 521; found 521.

4.2a t-Butyl (S)-1-(chloromethyl)-5-((4-aminobenzyl)oxy)-1,2-dihydro-3H-benzo[e]indole-3-carboxylate (17a)

To a solution of t-butyl (S)-1-(chloromethyl)-5-((4-nitrobenzyl)oxy)-1,2-dihydro-3H-benzo[e]indole-3-carboxylate (16a) (208 mg, 0.443 mmol) in THF/Acetone (11.1 mL/8.9 mL, respectively), under Ar, was added H$_2$O (4.5 mL), Zn dust (868 mg, 13.3 mmol) and NH$_4$Cl (1.42 mg, 26.6 mmol). The resulting mixture was stirred at 22° C. for 45 min. The reaction mixture was then filtered through a pad of Celite® and washed with DCM (20 mL). The filtrate was concentrated then partitioned between DCM and H$_2$O. The organics were then dried over MgSO$_4$, filtered and concentrated. The isolated crude residue was deemed pure desired product (17a) as a yellow foam (191 mg, 98% yield, 0.435 mmol).

$^1$H NMR (500 MHz, CDCl$_3$): δ 8.25 (d, J=8.2 Hz, 1H), 7.85 (bs, 1H), 7.63 (d, J=8.2 Hz, 1H), 7.50-7.47 (m, 1H), 7.32-7.30 (m, 3H), 6.73 (d, J=8.2 Hz, 2H), 5.13 (s, 2H), 4.25 (bs, 1H), 4.12 (t, J=10.0 Hz, 1H), 3.95 (q, J=9.9 Hz, 2H), 3.73 (s, 2H), 3.43 (t, J=10.3 Hz, 1H), 1.61 (s, 9H).

LC/MS: retention time 3.44 min. (ESI) C$_{25}$H$_{27}$ClN$_2$O$_3$Na: [M+Na]$^+$ 461; found 461.

4.2b t-Butyl (S)-1-(chloromethyl)-5-((3-methoxy-4-aminobenzyl)oxy)-1,2-dihydro-3H-benzo[e]indole-3-carboxylate (17b)

OxoDuocarmycin 17b was synthesized according to the same procedure as 17a but starting with t-butyl (S)-1-(chloromethyl)-5-((3-methoxy-4-nitrobenzyl)oxy)-1,2-dihydro-3H-benzo[e]indole-3-carboxylate 17a.

LC/MS: retention time 3.44 min. (ESI) C$_{26}$H$_{30}$ClN$_2$O$_4$: [M+H]$^+$ 469; found 469.

4.3a t-Butyl (S)-1-(chloromethyl)-((4-((34S,37S)-34-isopropyl-2,2,37-trimethyl-4,32,35-trioxo-3,8,11,14,17,20,23,26,29-nonaoxa-5,33,36-triazaoctatriacontan-38-amido)benzyl)oxy)-1,2-dihydro-3H-benzo[e]indole-3-carboxylate (18a)

To a solution of t-butyl (S)-1-(chloromethyl)-5-((4-aminobenzyl)oxy)-1,2-dihydro-3H-benzo[e]indole-3-carboxylate (17a) (51.5 mg, 0.117 mmol) and HOAlaValPeg$_8$NHBoc (91.9 mg, 0.129 mmol) in 10:1 DCM/MeOH (550 μL), under Ar, was added EEDQ (55.0 mg, 0.222 mmol). The resulting mixture was stirred at 22° C. for 3.5 h. The reaction mixture was then concentrated, dissolved in DMSO and directly loaded and purified via reverse phase column chromatography (0→100% ACN in H$_2$O, each containing 0.05% AcOH) and desired fractions lyophilized to afford (18a) as a white solid (49.2 mg, 38% yield, 0.00439 mmol).

$^1$H NMR (500 MHz, CDCl$_3$): δ 8.59 (bs, 1H), 8.25 (d, J=8.7 Hz, 1H), 7.86 (bs, 1H), 7.76 (d, J=8.0 Hz, 2H), 7.64 (d, J=8.1 Hz, 1H), 7.51-7.46 (m, 3H), 7.32 (t, J=7.2 Hz, 1H), 6.96 (s, 1H), 6.82 (s, 1H), 5.20 (s, 2H), 5.02 (bs, 1H), 4.67 (t, J=7.0 Hz, 1H), 4.28-4.21 (m, 2H), 4.13 (t, J=10.5 Hz, 1H), 3.95 (q, J=10.6 Hz, 2H), 3.88 (dt, J=10.6, 5.2 Hz, 1H), 3.71-3.61 (m, 28H), 3.53 (t, J=4.7 Hz, 2H), 3.43 (t, J=10.4 Hz, 2H), 3.30 (bs, 2H), 2.67 (t, J=13.3 Hz, 1H), 2.50-2.47 (m, 1H), 2.31-2.30 (m, 1H), 1.61 (s, 9H), 1.47 (d, J=7.2 Hz, 3H), 1.44 (s, 9H), 1.01 (dd, J=15.0, 6.9 Hz, 6H).

LC/MS: retention time 3.44 min. (ESI) C$_{57}$H$_{86}$ClN$_5$O$_{16}$Na: [M+Na]$^+$ 1154; found 1154.

4.3b t-Butyl (S)-1-(chloromethyl)-5-((4-((34S,37S)-34-isopropyl-2,2,37-trimethyl-4,32,35-trioxo-3,8,11,14,17,20,23,26,29-nonaoxa-5,33,36-triazaoctatriacontan-38-amido-3-methoxybenzyl)oxy)-1,2-dihydro-3H-benzo[e]indole-3-carboxylate (18b)

OxoDuocarmycin 18b was synthesized according to the same procedure as 18a but starting with t-butyl (S)-1-(chloromethyl)-5-((3-methoxy-4-aminobenzyl)oxy)-1,2-dihydro-3H-benzo[e]indole-3-carboxylate 17b.

$^1$H NMR (500 MHz, CDCl$_3$) δ: 8.37 (bs, 1H), 8.34 (d, J=8.7 Hz, 1H) 8.25 (d, J=8.7 Hz, 1H), 7.86 (bs, 1H), 7.64 (d, J=8.1 Hz, 1H), 7.51 (t, J=8.0 Hz, 1H), 7.33 (t, J=7.2 Hz, 1H), 7.12 (d, J=8.0 Hz, 1H), 7.07 (s, 1H), 6.94 (d, J=8.0 Hz, 1H), 6.84 (br, 1H), 5.22 (s, 2H), 5.07 (bs, 1H), 4.65 (t, J=7.0 Hz, 1H), 4.35-4.24 (m, 2H), 4.13 (t, J=10.5 Hz, 1H), 3.95 (m, 2H), 3.92 (s, 3H), 3.77 (m, 2H), 3.71-3.61 (m, 28H), 3.54 (t, J=4.7 Hz, 2H), 3.43 (t, J=10.4 Hz, 1H), 3.31 (m, 2H), 2.55 (m, 1H), 2.21 (m, 1H), 1.81 (br, 3H), 1.61 (s, 9H), 1.48 (d, J=7.2 Hz, 3H), 1.45 (s, 9H), 0.98 (dd, J=15.0, 6.9 Hz, 6H).

LC/MS: retention time 3.46 min. (ESI) C$_{58}$H$_{88}$ClN$_5$O$_{17}$: [M+Na]$^+$ 1184; found 1184.

4.4a N—((S)-1-(((S)-1-((4-((((S)-1-(chloromethyl)-3-(4-(((S)-2-methoxy-14-oxo-6a,7,12,14-tetrahydrobenzo[5,6][1,4]diazepino[1,2-b]isoquinolin-3-yl)oxy)butanoyl)-2,3-dihydro-1H-benzo[e]indol-5-yl)oxy)methyl)phenyl)amino)-1-oxopropan-2-yl)amino)-3-methyl-1-oxobutan-2-yl)-1-(3-(2,5-dioxo-2,5-dihydro-1H-pyrrol-1-yl)propanamido)-3,6,9,12,15,18,21,24-octaoxaheptacosan-27-amide (19a) (D820b)

To t-butyl (S)-1-(chloromethyl)-5-((4-((34S,37S)-34-isopropyl-2,2,37-trimethyl-4,32,35-trioxo-3,8,11,14,17,20,23,26,29-nonaoxa-5,33,36-triazaoctatriacontan-38-amido)benzyl)oxy)-1,2-dihydro-3H-benzo[e]indole-3-carboxylate (18a) in a 20 mL vial, cooled to 0° C., was added 2:1 DCM/TFA (0.75 mL, precooled to −20° C.). The reaction mixture was stirred at 0° C. for 30 min, at which time the reaction was judged complete by LC/MS. The reaction was concentrated in vacuo, then azeotroped with CHCl$_3$ (4×5 mL) and left on high vac for 16 h. The residue was then dissolved in DCM (1 mL) and TEA (6 μL, 0.0422 mmol) was then added. An additional 2 μL of TEA was added to basify the reaction to pH-8, then maleimine NHS ester (9) (9.8 mg, 0.0369 mmol) was added and the resulting mixture was stirred at 22° C. for 15 min, at which point the reaction was judged complete by LC/MS. The reaction mixture was then concentrated and azeotroped with CHCl$_3$ (3×5 mL) and left on high vac for 1 h. The residue was then dissolved in anhydrous DMF (1 mL) and IQB acid (14) (20.8 mg, 0.0528 mmol), pTsOH (10 ms, 0.053 mmol) and EDC.HCl (30.3 mg, 0.158 mmol) were added to the reaction. The resulting mixture was stirred at 22° C. for 10 min, then directly loaded and purified via reverse phase column chromatography (0→100% ACN in H$_2$O, each containing 0.05% AcOH) and product containing fractions were lyophilized then repurified on EZ Prep (Gemini 30×150 mm column) (5→95% ACN in H$_2$O, each containing 0.05% AcOH) to afford (19a) as a white solid (1.7 mg, 5.5% yield over 3 steps, 0.00116 mmol).

LC/MS: retention time 2.73 min. (ESI) C$_{76}$H$_{96}$ClN$_8$O$_{19}$: [M+H]$^+$ 1459; found 1459.

4.4b N—((S)-1-(((S)-1-((4-((((S)-1-(chloromethyl)-3-(4-(((S)-2-methoxy-14-oxo-6a,7,12,14-tetrahydrobenzo[5,6][1,4]diazepino[1,2-b]isoquinolin-3-yl)oxy)butanoyl)-2,3-dihydro-1H-benzo[e]indol-5-yl)oxy)methyl)-2-methoxyphenyl)amino)-1-oxopropan-2-yl)amino)-3-methyl-1-oxobutan-2-yl)-1-(3-(2,5-dioxo-2,5-dihydro-1H-pyrrol-1-yl)propanamido)-3,6,9,12,15,18,21,24-octaoxaheptacosan-27-amide (19b) (D820)

OxoDuocarmycin 19b was synthesized according to the same procedure as 19a but starting t-butyl (S)-1-(chloromethyl)-5-((4-((34S,37S)-34-isopropyl-2,2,37-trimethyl-4,32,35-trioxo-3,8,11,14,17,20,23,26,29-nonaoxa-5,33,36-triazaoctatriacontan-38-amido)-3-methoxybenzyl)oxy)-1,2-dihydro-3H-benzo[e]indole-3-carboxylate 18b.

LC/MS: retention time 2.77 min. (ESI) $C_{77}H_{98}ClN_8O_{20}$: [M+H]$^+$ 1491; found 1491.

Example 4: General Experimental Protocols for the Synthesis of IQB-Oxoduocarmycins Analogs: D822, D824, D826 and D828

General Methods:

$^1$H NMR spectra were recorded on a Varian Inova 300 or 500 MHz NMR instrument. Chromatographic purities were determined on an Agilent 1200 Series, 1100 Series or 6130 Series LC/MS system using a Merck Chromolith RP-18e analytical HPLC column (monolithic, 50×2 mm) and the following analytical HPLC method: injection volume 5 μL; flow rate 1 mL/min; 5→95% acetonitrile in water with 0.05% AcOH over 5 mins; Agilent diode array detector at λ=254, 220 or 195 nm; room temperature.

Figure 11:
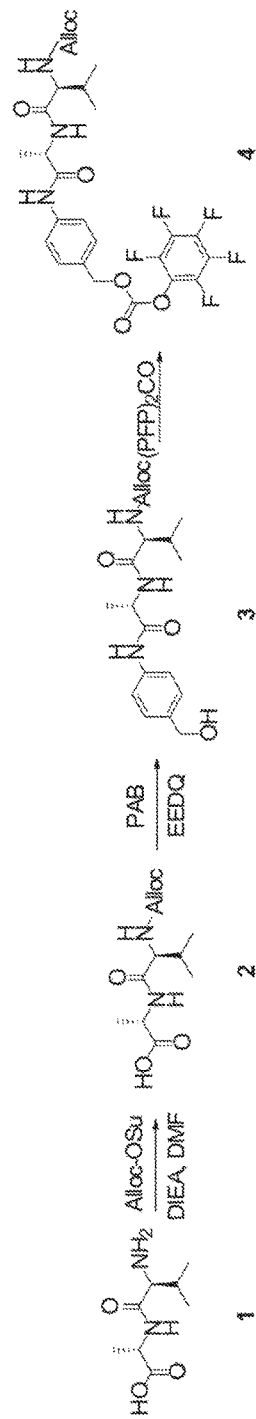
FIG. 11 shows synthesis of a linker L.

1.0 Synthesis of Linker (Scheme II) (Referring to FIG. 11)

1.1 ((Allyloxy)carbonyl)-L-valyl-L-alanine (2)

To a solution NH$_2$-Val-Ala-OH (941 mg, 5 mmol) in DMF (10 mL), added DIEA (1.73 mL, 10 mmol) and N-(Allyloxycarbonyloxy)succinimide (1.15 mL, 7.5 mmol). Reaction mixture was stirred for 3 hr, quenched with water (3 mL) and stirred overnight. Solvent was removed in vacuo and the residue was diluted with HCl in water (40 mL, 0.25 M). After sonication, the precipitate was filtered off and dried thoroughly to afford 2 (600 mg, 44% yield).

$^1$H NMR (500 MHz, DMSO-d6): δ 12.48 (bs, 1H), 8.18 (d, J=7.0 Hz, 1H), 7.16 (d, J=9.4 Hz, 1H), 5.95-5.83 (m, 1H), 5.28 (d, J=15.8 Hz, 1H), 5.17 (d, J=10.5 Hz, 1H), 4.47 (m, 2H), 4.18 (m, 1H), 3.87 (m, 1H), 1.94 (m, 1H), 1.26 (d, J=7.6 Hz, 3H), 0.86 (dd, J=14.6, 6.7 Hz, 6H).

LC/MS: retention time 0.25 min. (ESI) $C_{12}H_{21}N_2O_5$: [M+H]$^+$ 273; found 273.

1.2 Allyl ((S)-1-(((S)-1-((4-(hydroxymethyl)phenyl) amino)-1-oxopropan-2-yl)amino)-3-methyl-1-oxobutan-2-yl)carbamate (3)

To a solution of ((Allyloxy)carbonyl)-L-valyl-L-alanine (2) (3.00 g, 11.0 mmol) and p-aminobenzyl alcohol (1.56 g, 12.7 mmol) in DCM (110 mL) and MeOH (55 mL), under Ar, added EEDQ (5.12 g, 20.7 mmol). The reaction mixture was stirred at 22° C. for 19 hr, then concentrated and purified via column chromatography (0→10% MeOH in DCM) to afford 3 (2.48 g, 60% yield).

$^1$H NMR (500 MHz; CD$_3$OD): δ 7.57 (d, J=8.3 Hz, 2H), 7.32 (d, J=8.3 Hz, 2H), 6.00-5.92 (m, 1H), 5.33 (d, J=17.4 Hz, 1H), 5.20 (d, J=10.5 Hz, 1H), 4.57 (s, 2H), 4.51 (q, J=7.1 Hz, 1H), 3.97 (d, J=6.6 Hz, 1H), 3.37 (s, 2H), 2.11 (dq, J=13.7, 6.8 Hz, 1H), 1.46 (d, J=7.1 Hz, 3H), 0.99 (dd, J=17.8, 6.8 Hz, 6H).

LC/MS: retention time 2.02 min. (ESI) $C_{19}H_{28}N_4O_5$: [M+H]$^+$ 378; found 378.

1.3 Allyl ((S)-3-methyl-1-oxo-1-(((S)-1-oxo-1-((4-((((perfluorophenoxy)carbonyl)-oxy)-methyl)-phenyl)-amino)-propan-2-yl)-amino)-butan-2-yl)carbamate (4)

To a solution of allyl ((S)-1-(((S)-1-((4-(hydroxymethyl) phenyl)amino)-1-oxopropan-2-yl)amino)-3-methyl-1-oxobutan-2-yl)carbamate (3) (417 mg, 1.10 mmol) in DMF (5.5 mL), under Ar, added DIEA (383 μL, 2.20 mmol) and bis(pentafluorophenyl)carbonate (653 mg, 1.66 mmol). The reaction was stirred at 22° C. for 1 hr, then additional DIEA (190 ml, 1.10 mmol) and bis(pentafluorophenyl)carbonate (433 mg, 1.10 mmol) were added and the mixture was stirred for an additional 1 hr. The mixture was then loaded directly and purified via reverse phase column chromatography (0→100% ACN in H$_2$O, each containing 0.05% AcOH) and desired fractions lyophilized to afford 4 (442 mg, 68% yield).

$^1$H NMR (500 MHz; CDCl$_3$): δ 8.51 (s, 1H), 7.65 (d, J=7.8 Hz, 2H), 7.40 (d, J=8.5 Hz, 2H), 6.34 (d, J=7.3 Hz, 1H), 5.98-5.89 (m, 1H), 5.36-5.25 (m, 2H), 5.30 (s, 2H), 5.19-5.18 (m, 1H), 4.67 (t, J=7.1 Hz, 1H), 4.62 (d, J=4.9 Hz, 2H), 4.01 (t, J=6.4 Hz, 1H), 2.27-2.20 (m, 1H), 1.52 (d, J=7.1 Hz, 3H), 1.00 (dd, J=23.2, 6.9 Hz, 6H).

LC/MS: retention time 3.44 min. (ESI) $C_{26}H_{27}F_5N_3O_7$: [M+H]$^+$ 588; found 588.

Figure 12:
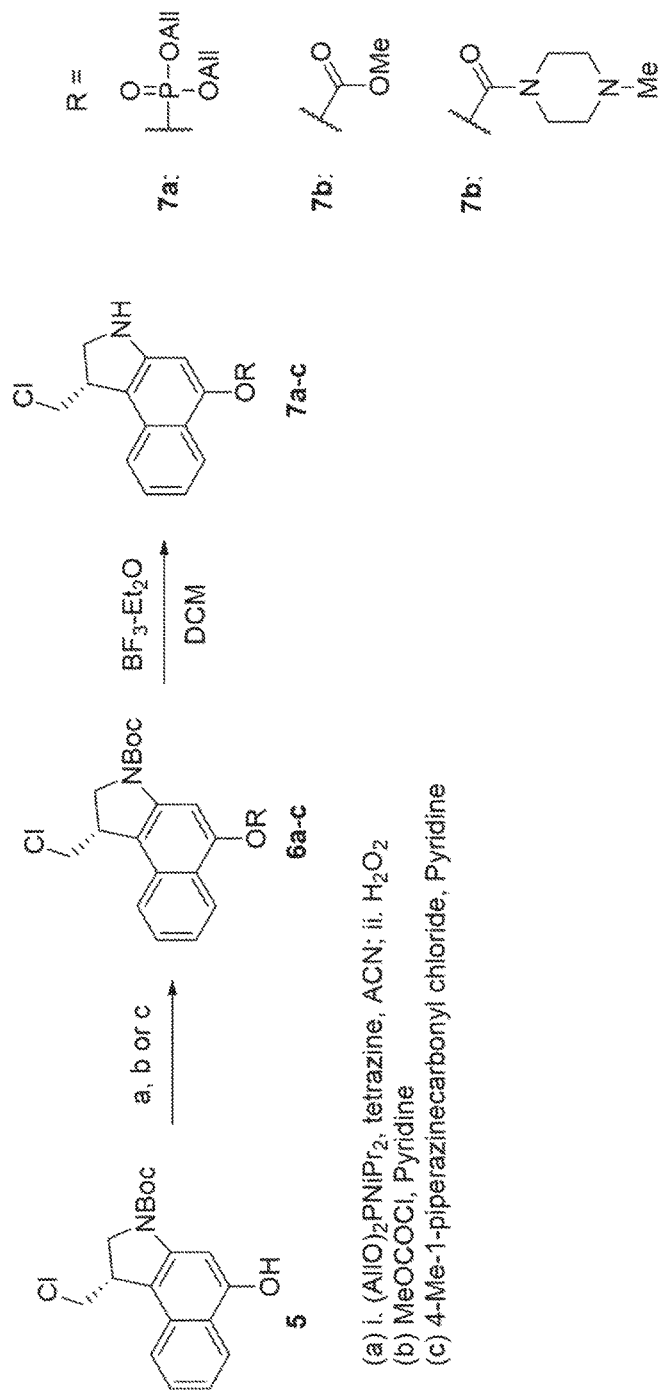
FIG. 12 shows synthesis of a CBI moiety.

2.0 Synthesis of CBI Moiety (Scheme 12) (Referring to FIG. 12)

2.1 Tert-butyl (S)5-((bisallyloxy)phosphoryl)oxy)-1-(chloromethyl)-1,2-dihydro-3H-benzo[e]indole-3-carboxylate (6a)

To a solution of 5 (67 mg, 0.2 mmol) in THF (1 mL), under Ar, added tetrazine (0.9 mL, 0.45 M solution in ACN) and diallyloxyphosphoramide (0.11 mL, 0.4 mmol). The resulting mixture was stirred at 22° C. for 2 hr, then hydrogen peroxide (0.045 mL, 50% in water) was added at once. After stirring for 45 minutes, the mixture was concentrated to dryness, dissolved in 1 mL DMSO and purified via reverse phase column chromatography (0→100% ACN in H$_2$O, each containing 0.05% AcOH) and desired fractions lyophilized to afford 6a (72 mg, 73% yield).

$^1$H NMR (500 MHz, CDCl$_3$): 8.13 (d, J=8.3 Hz, 1H), 7.69 (d, J=8.3 Hz, 1H), 7.53 (t, J=7.6 Hz, 1H), 7.40 (t, J=7.6 Hz, 1H), 5.96 (m, 2H), 5.39 (d, J=17.1 Hz, 1H), 5.26 (m, 2H), 4.71 (m, 4H), 4.30 (m, 1H), 4.14 (m, 1H), 3.99 (m, 1H), 3.91 (d, J=10.7 Hz, 1H), 3.46 (t, J=10.7 Hz, 1H), 1.62 (bs, 9H).

LC/MS: retention time 3.75 min. (ESI) $C_{24}H_{29}ClNO_6PNa$: [M+Na]$^+$ 516; found 516.

2.2 Tert-butyl (S)-1-(chloromethyl)-5-((methoxycarbonyl)oxy)-1,2-dihydro-3H-benzo[e]indole-3-carboxylate (6b)

To a solution of 5 (67 mg, 0.2 mmol) in DCM (2 mL), under Ar, added a solution pyridine (0.081 mL, 1 mmol) and methyl chloroformate (0.046 mL, 0.6 mmol). After 30 minutes, the reaction mixture was concentrated to dryness, dissolved on small amount of DCM and loaded on 12 g silica Isco column (0→50% EtOAc in hexane). Desired fractions were concentrated to afford 6b (71 mg, 91% yield)

$^1$H NMR (500 MHz, CDCl$_3$): 8.16 (bs, 1H), 7.93 (d, J=8.8 Hz, 1H), 7.72 (d, J=8.8 Hz, 1H), 7.54 (m, 1H), 7.40 (m, 1H), 4.30 (bs, 1H), 4.16 (m, 1H), 4.03 (m, 1H), 3.97 (m, 4H), 3.49 (t, J=11.0 Hz, 1H), 1.61 (s, 9H).

LC/MS: retention time 3.72 min. (ESI) $C_{20}H_{22}ClNO_5Na$: [M+Na]$^+$414; found 414.

2.3 Tert-butyl (S)-1-(chloromethyl)-5-((4-methylpiperazine-1-carbonyl)oxy)-1,2-dihydro-3H-benzo[e] indole-3-carboxylate (6c)

To a solution of 5 (100 mg, 0.3 mmol) in DCM (2 mL), under Ar, added pyridine (0.073 mL, 0.90 mmol) and 4-methylpiperazine-1-carbonyl chloride (0.061 mL, 0.45 mmol). After 16 h, the reaction mixture was concentrated to dryness, dissolved on 1 mL of DMSO purified via reverse phase column chromatography (0→100% ACN in $H_2O$, each containing 0.05% AcOH) and desired fractions lyophilized to afford 6c (133 mg, 97% yield).

$^1$H-NMR (500 MHz; $CDCl_3$): δ 8.09 (bs, 1H), 7.86 (d, J=8.3 Hz, 1H), 7.72 (d, J=8.5 Hz, 1H), 7.52 (t, J=7.6 Hz, 1H), 7.39 (t, J=7.7 Hz, 1H), 4.28 (bs, 1H), 4.16 (t, J=10.2 Hz, 1H), 4.05-4.01 (m, 1H), 3.97-3.95 (m, 1H), 3.87 (bs, 2H), 3.66 (bs, 2H), 3.49 (t, J=10.8 Hz, 1H), 2.54 (bd, J=16.6 Hz, 4H), 2.41 (s, 3H), 1.61 (s, 9H).

LC/MS: retention time 2.31 min. (ESI) $C_{24}H_{31}ClN_3O_4$: $[M+H]^+$ 460; found 460.

2.4 General Procedure for Removal of Boc Group (7a-c)

6a, 6b, or 6c (0.05 mmol) was dissolved in anhydrous DCM (1.6 mL) and boron trifluoride etherate (0.031 mL, 0.25 mmol) was added at once. After stirring for 40 minutes, the reaction mixture was concentrated to dryness and thoroughly dried on hi-vacuum before next step. No purification, material used as is in subsequent step.

Figure 13:
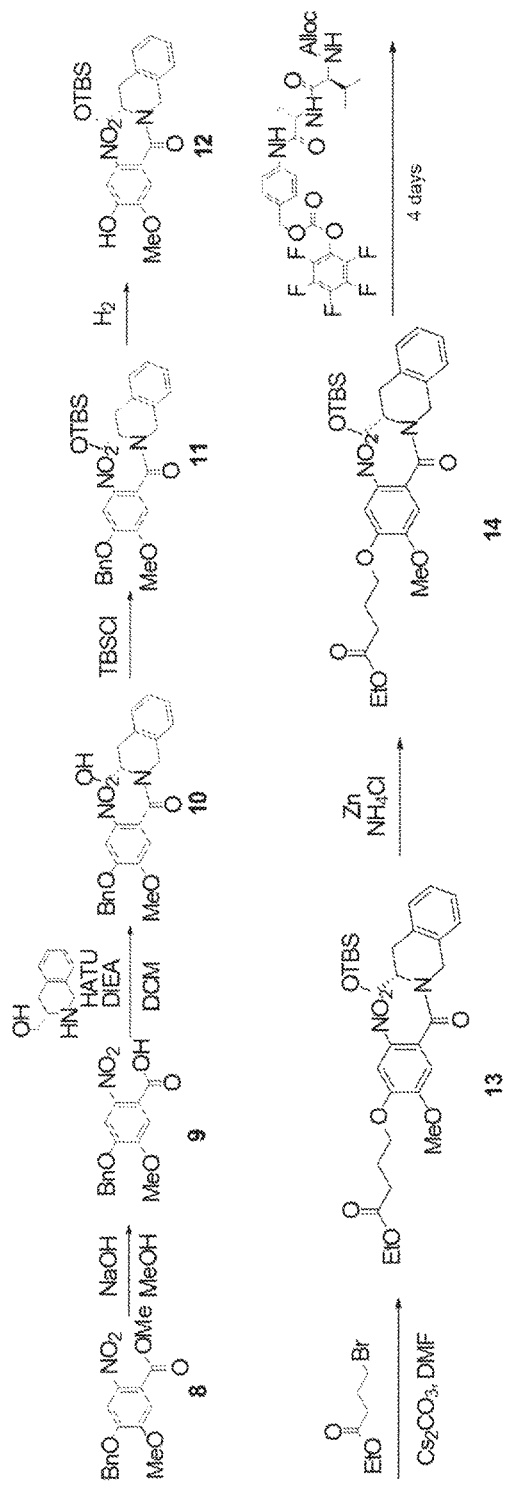
FIG. 13 shows synthesis of IQB moiety and final assembly (Part 1).
Figure 13:
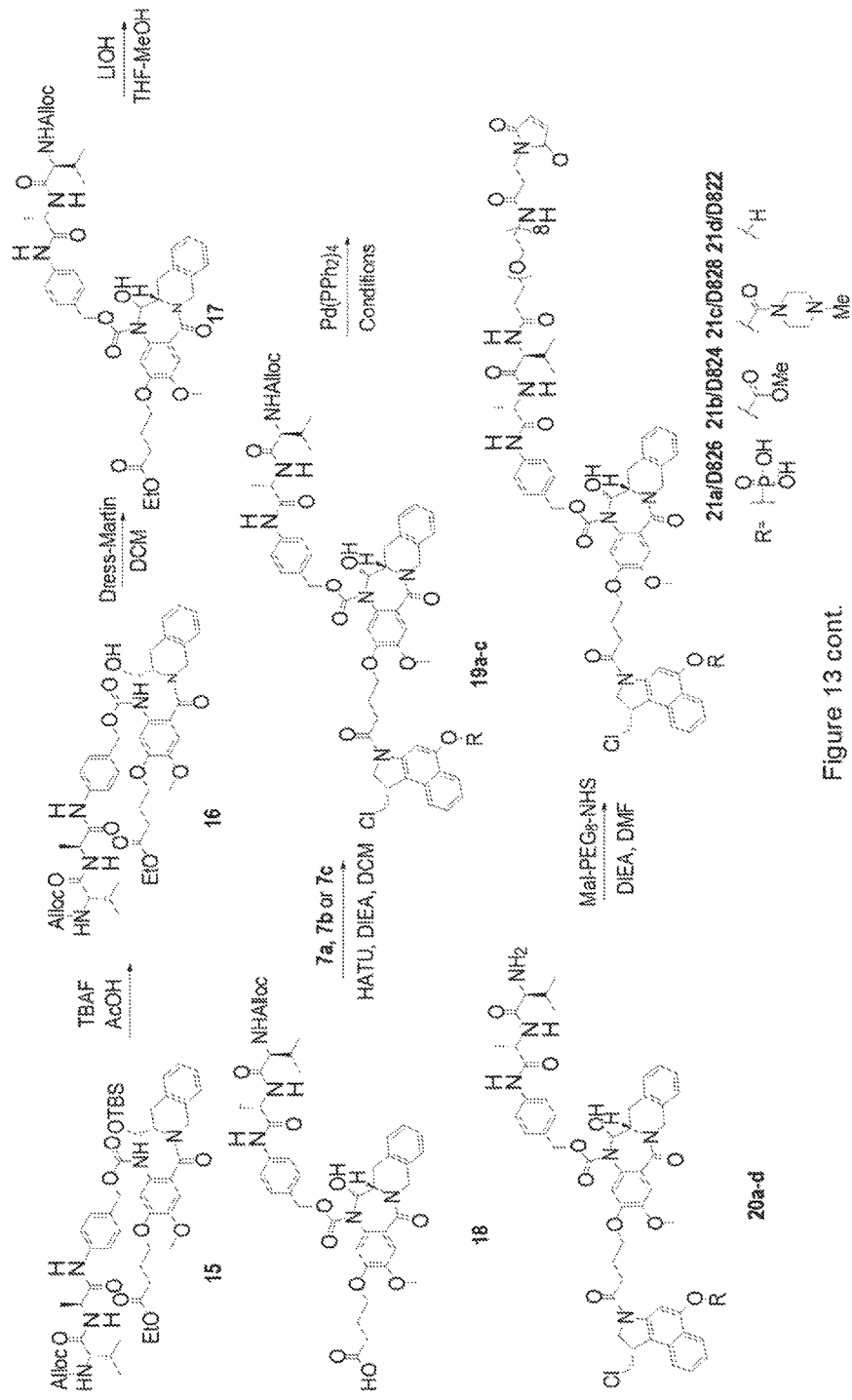
Figure 14:
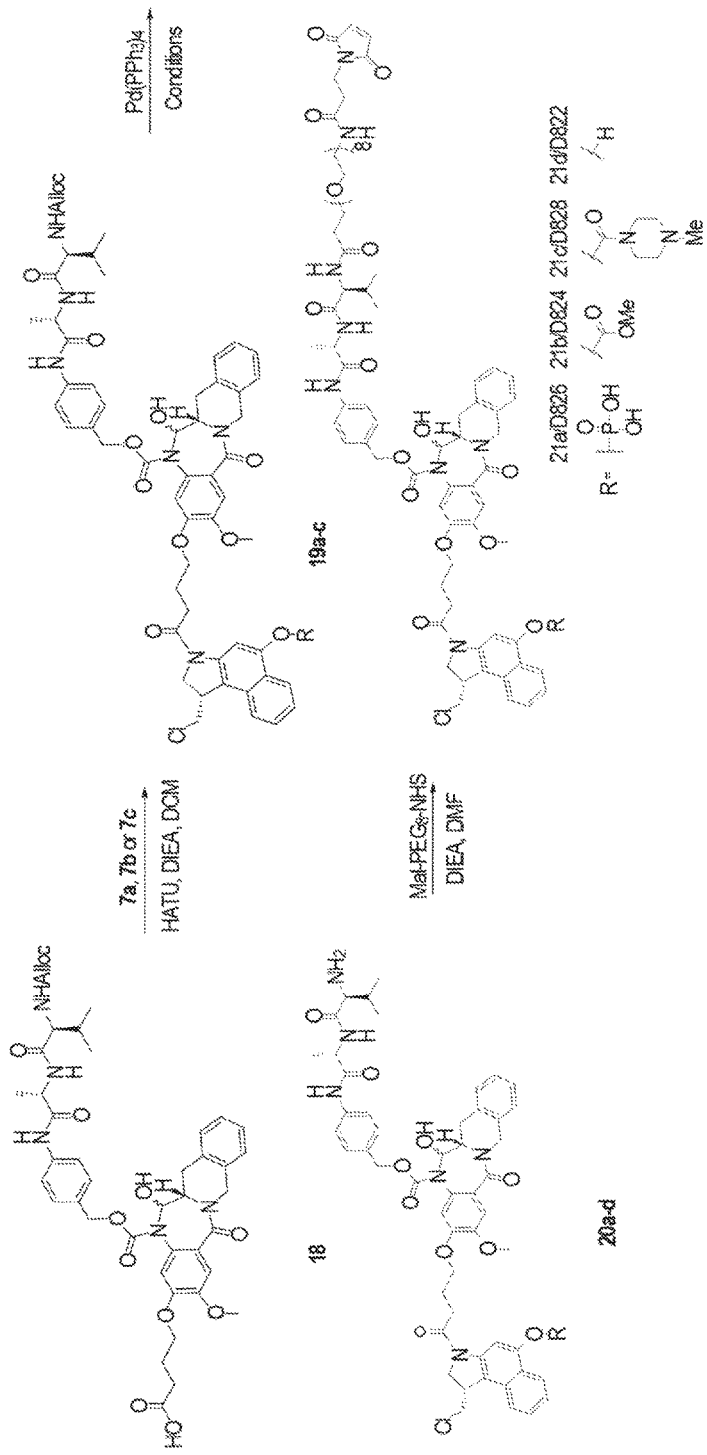
FIG. 14 shows synthesis of IQB moiety and final assembly (Part 2).

3.0 Synthesis of IQB Moiety and Final Assembly (Scheme 13) (Referring to FIGS. 13 and 14)

3.1 4-(Benzyloxy)-5-methoxy-2-nitrobenzoic acid (9)

4-Benzyloxy-5-methoxy-benzoic acid methyl ester (9.1 g, 29 mmol) was dissolved in methanol (145 mL) and sodium hydroxide (6 M solution, 24 mL) was added at once. The reaction mixture was stirred for 1 hr at 50° C., then methanol was evaporated. Concentrated hydrochloric acid (12 mL) was added slowly to the residue with stirring. Formed precipitate was filtered off, washed with water and dried to afford 8.1 g of 3 (92% yield).

$^1$H NMR (500 MHz, DMSO-d6) δ: 7.69 (s, 1H), 7.36-7.47 (m, 5H), 7.31 (s, 1H), 5.24 (s, 2H), 3.91 (s, 3H).

LC/MS: retention time 2.40 min (ESI) $C_{15}H_{13}NO_6Na$: $[M+Na]^+$ 326; found 326.

3.2 (S)-(4-(Benzyloxy)-5-methoxy-2-nitrophenyl)(3-(hydroxymethyl)-3,4-dihydroisoquinolin-2(1H)-yl)methanone (10)

To a solution of 4-(benzyloxy)-5-methoxy-2-nitrobenzoic acid (9) (10.0 g, 33.0 mmol) in DCM (100 mL) added HATU (16.3 g, 42.9 mmol) and DIEA (8.61 mL, 49.5 mmol). The mixture was stirred at 22° C. for 15 min, then added (S)-(1,2,3,4-tetrahydroisoquinolin-3-yl)methanol (6.46 g, 39.6 mmol). The resulting mixture was stirred at 22° C. for 2 hr, under Ar, then MeOH (50 mL) was added and the resulting precipitate was filtered and washed with DCM (100 mL). The resulting filtrate was concentrated and purified via column chromatography (25→85% EtOAc in hexane) to afford impure 10 (15.3 g 34.1 mmol) as a yellow foam.

$^1$H NMR (500 MHz; $CDCl_3$) (contains rotamers and impurities): δ 8.67 (d, J=4.6 Hz, 0.3H), 8.43 (d, J=8.5 Hz, 0.3H), 7.85-7.82 (m, 2H), 7.79 (s, 0.3H ), 7.50 (t, J=5.4 Hz, 5H), 7.46-7.43 (m, 4H), 7.40-7.38 (m, 2H), 7.26-7.22 (m, 2H), 7.19-7.16 (m, 1H), 7.11-7.06 (m, 0.3H), 6.87 (d, J=7.0 Hz, 1H), 6.75 (dd, J=1.8, 0.5 Hz, 0.3H), 6.67 (s, 1H), 5.62-5.52 (m, 1H), 5.26 (s, 2H), 5.25-5.25 (m, 1H), 5.11 (s, 0.3H), 4.98-4.96 (m, 1H), 4.46-4.41 (m, 1H), 4.34 (d, J=15.4 Hz, 1H), 4.28-4.23 (m, 1H), 4.03 (s, 2H), 3.97 (s, 3H), 3.93-3.91 (m, 3H), 3.80-3.75 (m, 1H), 3.68-3.62 (m, 1H), 3.49-3.48 (m, 1H), 3.28-3.22 (m, 0.3H), 3.19-3.10 (m, 1H), 3.08-3.03 (m, 1H), 2.82 (s, 14H).

LC/MS: retention time 3.15 min. (ESI) $C_{25}H_{25}N_2O_6$: $[M+H]^+$ 449; found 449.

3.3 (S)-(4-(Benzyloxy)-5-methoxy-2-nitrophenyl)(3-(((tert-butyldimethylsilyl)oxy)methyl)-3,4-dihydroisoquinolin-2(1H)-yl)methanone (11)

To a solution of (S)-(4-(benzyloxy)-5-methoxy-2-nitrophenyl)(3-(hydroxymethyl)-3,4-dihydroisoquinolin-2(1H)-yl)methanone (10) (15.3 g, 34.1 mmol) in DCM (155 mL), under Ar, added imidazole (4.64 g, 68.2 mmol) then TBSCl (7.71 g, 51.2 mmol). The resulting mixture was stirred at 22° C. for 15 min, then was quenched with $H_2O$ (100 mL), extracted with DCM (3×150 mL), dried over $MgSO_4$, filtered and concentrated. The residue was purified via column chromatography (0→50% EtOAc in hexane) to afford 11 (14.0 g, 76% yield) as a yellow foam.

$^1$H NMR (500 MHz; $CDCl_3$) (contains a mixture of rotamers): δ 7.85 (s, 0.4H), 7.82-7.81 (m, 0.6H), 7.50-7.49 (m, 2H), 7.45-7.42 (m, 2H), 7.41-7.36 (m, 1H), 7.24-7.20 (m, 3H), 7.16-7.12 (m, 1H), 6.91 (s, 0.3H), 6.85-6.82 (m, 1H), 6.75 (bs, 0.3H), 6.67 (s, 0.3H), 5.42-5.37 (m, 0.3H), 5.26 (s, 2H), 5.10 (bs, 0.2H), 5.01 (bs, 0.3H), 4.43 (d, J=17.1 Hz, 0.5H), 4.32 (d, J=15.3 Hz, 0.6H), 4.24-4.19 (m, 0.5H), 4.00 (d, J=12.1 Hz, 2H), 3.91 (s, 1H), 3.85 (s, 0.4H), 3.78-3.74 (m, 0.6H), 3.68-3.64 (m, 0.4H), 3.50 (bs, 0.6H), 3.38 (s, 0.3H ), 3.21 (bd, J=16.5 Hz, 0.5H), 3.10 (dd, J=16.8, 5.9 Hz, 0.4), 2.99 (d, J=17.3 Hz, 0.6H), 2.77 (bd, J=15.0 Hz, 0.2), 0.92 (s, 2H), 0.87 (d, J=7.6 Hz, 3H), 0.81-0.76 (m, 4H), 0.04 (dd, J=22.9, 12.2 Hz, 3H), -0.11-0.18 (m, 2H).

LC/MS: retention time 4.47 min. (ESI) $C_{31}H_{39}N_2O_6Si$: $[M+H]^+$ 563; found 563.

3.4 (S)-(3-(((Tert-butyldimethylsilyl)oxy)methyl)-3,4-dihydroisoquinolin-2(1H)-yl)(4-hydroxy-5-methoxy-2-nitrophenyl)methanone (12)

To a solution of (S)-(4-(benzyloxy)-5-methoxy-2-nitrophenyl)(3-(((tert-butyldimethylsilyl)oxy)methyl)-3,4-dihydroisoquinolin-2(1H)-yl)methanone (11) (14.0 g, 24.9 mmol) in EtOAc (500 mL), vacuum purged with Ar (3×), added Pd(OH)2/C (710 mg). The reaction mixture was then vacuum purged with Ar (3×), followed by $H_2$ (3×). The mixture was stirred at 22° C. under $H_2$ for 2.5 hr, with vigorous agitation. The mixture was then vacuum purged with Ar, and the mixture filtered through Celite®, washed with EtOAc and the filtrate was concentrated. The residue was purified via column chromatography (10→100% EtOAc in hexane) to afford 12 (11.3 g, 97% yield) as a yellow foam, containing ~6% overreduction (aniline) impurity.

$^1$H NMR (500 MHz; $CDCl_3$) (contains rotamers and aniline impurity): δ 7.86-7.81 (m, 1H), 7.24-7.21 (m, 2H), 7.17-7.11 (m, 0.7H), 6.93-6.89 (m, 0.2H), 6.86-6.85 (m, 0.7H), 6.82 (dt, J=1.8, 0.8 Hz, 0.2H), 6.69 (t, J=0.9 Hz, 0.2H), 5.90 (s, 1H), 5.43 (bs, 0.4H), 5.09 (s, 0.3H), 5.05-5.00 (m, 0.3H), 4.42 (dd, J=17.1, 0.7 Hz, 0.5H), 4.32 (t, J=13.2 Hz, 0.5H), 4.25-4.21 (m, 0.6H), 4.05 (dd, J=2.1, 1.5 Hz, 0.8H), 4.02 (s, 1.7H), 3.95 (d, J=0.5 Hz, 1H), 3.90-3.83 (m, 0.8H), 3.77-3.66 (m, 1H), 3.55-3.48 (m, 0.4H), 3.41-3.38

(m, 0.1H), 3.22 (d, J=16.1 Hz, 0.5H), 3.13-2.99 (m, 0.8H), 0.92 (s, 2H), 0.87 (d, J=7.0 Hz, 4H), 0.81 (s, 4H), 0.07-0.03 (m, 4H), -0.10 (s, 3H).
LC/MS: retention time 4.42 min. (ESI) $C_{24}H_{33}N_2OSi$: [M+H]$^+$ 473; found 473.

3.5 Ethyl (S)-4-(4-(3-(((tert-butyldimethylsilyl)oxy) methyl)-1,2,3,4-tetrahydroisoquinoline-2-carbonyl)-2-methoxy-5-nitrophenoxy)butanoate (13)

To a solution of (S)-(3-(((tert-butyldimethylsilyl)oxy) methyl)-3,4-dihydroisoquinolin-2(1H)-yl)(4-hydroxy-5-methoxy-2-nitrophenyl)methanone (12) (2.57 g, 5.44 mmol) and $Cs_2CO_3$ (5.32 g, 16.3 mmol) in DMF (27 mL) added ethyl 4-bromobutanoate (2.34 mL 16.3 mmol). The reaction mixture was stirred at 22° C. for 2.5 hr, then quenched with $H_2O$ (100 mL) and extracted with EtOAc (3×100 mL). The combined organics were washed with $H_2O$ (3×50 mL), dried over $MgSO_4$, filtered, and concentrated. The residue was purified via column chromatography (0→50% EtOAc in hexane) to afford 13 (2.68 g, 84% yield).
$^1$H NMR (500 MHz; CDCl$_3$)(contains rotamers): δ 7.79-7.74 (m, 1H), 7.25-7.20 (m, 2H), 7.14 (dtd, J=4.5, 1.9, 0.9 Hz, 0.5H), 6.89-6.84 (m, 0.6H), 6.80 (d, J=0.9 Hz, 0.1H), 6.66 (s, 0.2H), 5.42-5.39 (m, 0.3H), 5.10 (bs, 0.2H), 5.01 (bs, 0.3H), 4.44-4.40 (m, 0.5H), 4.34-4.29 (m, 0.6H), 4.22-4.18 (m, 5H), 3.99-3.96 (m, 2H), 3.89 (s, 1H), 3.78-3.74 (m, 0.5H), 3.66 (bs, 0.2H), 3.51-3.48 (m, 0.4H), 3.38 (bs, 0.2H), 3.22 (dd, J=17.0, 1.8 Hz, 0.5H ), 3.13-3.09 (m, 0.3H), 3.01-2.98 (m, 0.6H), 2.79 (bt, J=2.1 Hz, 0.2H), 2.60-2.57 (m, 2H), 2.26-2.23 (m, 2H), 1.29 (dd, J=14.3, 9.9 Hz, 3H), 0.92 (s, 2H), 0.86 (s, 3H), 0.81-0.78 (m, 4H), 0.05 (t, J=8.5 Hz, 3H), -0.11 (bs, 2H).
LC/MS: retention time 4.24 min. (ESI) $C_{30}H_{43}N_2O_8Si$: [M+H]$^+$ 587; found 587.

3.6 Ethyl (S)-4-(5-amino-4-(3-(((tert-butyldimethylsilyl)oxy)methyl)-,2,3,4-tetrahydroisoquinoline-2-carbonyl)-2-methoxyphenoxy)butanoate (14)

To a solution of ethyl (S)-4-(4-(3-(((tert-butyldimethylsilyl)oxy)methyl)-1,2,3,4-tetrahydroisoquinoline-2-carbonyl)-2-methoxy-5-nitrophenoxy)butanoate (13) (2.68 g, 4.57 mmol) in THF (91 mL) and $H_2O$ (9.1 mL) added $NH_4Cl$ (4.89 g, 91.4 mmol) and Zn dust (2.99 g, 45.7 mmol). The resulting mixture was stirred at 22° C. for 2.5 hr, then filtered through Celite®, washed with EtOAc and the filtrate was concentrated. The residue was purified via column chromatography (0→75% EtOAc in hexane) to afford 14 (2.14 g, 84% yield).
$^1$H NMR (500 MHz; CDCl$_3$): δ 7.21-7.16 (m, 4H), 7.09-7.07 (m, 1H), 6.79 (s, 1H), 6.33 (s, 1H), 4.49 (bs, 1H), 4.18 (q, J=7.1 Hz, 2H), 4.07 (t, J=6.3 Hz, 2H), 3.79 (s, 3H), 3.68 (bs, 2H), 3.18 (dd, J=16.2, 5.9 Hz, 1H), 2.86-2.82 (m, 1H), 2.56 (t, J=7.3 Hz, 2H), 2.21-2.16 (m, 2H), 1.57 (bs, 3H) 1.29 (t, J=7.1 Hz, 3H), 0.87 (s, 9H), 0.01 (s, 6H).
LC/MS: retention time 3.94 min. (ESI) $C_{30}H_{45}N_2O_6Si$: [M+H]$^+$ 557; found 557.

3.7 Ethyl 4-(5-(((((4-((S)-2-((S)-2-(((allyloxy)carbonyl)amino)-3-methylbutanamido)-propanamido)-benzyl)-oxy)-carbonyl)-amino)-4-((S)-3-(((tert-butyldimethylsilyl)oxy)methyl)-1,2,3,4-tetrahydrosoquinoioine-2-carbonyl)-2-methoxyphenoxy)butanoate (15)

To a solution of ethyl (S)-4-(5-amino-4-(3-(((tert-butyldimethylsilyl)oxy)methyl)-1,2,3,4-tetrahydroisoquinoline-2-carbonyl)-2-methoxyphenoxy)butanoate (14) (545 mg, 0.978 mmol) in THF (1.5 mL) added a solution of allyl ((S)-3-methyl-1-oxo-1-(((S)-1-oxo-1-((4-((((perfluorophenoxy)carbonyl)-oxy)-methyl)-phenyl)-amino)-propan-2-yl)-amino)-butan-2-yl)carbamate (4) (442 mg, 0.752 mmol) in THF (0.5 mL). The reaction vessel was purged with Ar, sealed, and the reaction mixture was stirred at 22° C. for 4 days. The mixture was then concentrated, and the residue was purified via reverse phase chromatography (0→100% ACN in $H_2O$, each containing 0.05% AcOH). The desired fractions were lyophilized and impure product was purified via column chromatography (0→100% EtOAc in hexane) to afford 15 (520 mg, 72% yield).
$^1$H NMR (500 MHz; CDCl$_3$, 50° C.): δ 8.25-8.23 (m, 2H), 7.81 (bs, 1H), 7.51 (d, J=8.0 Hz, 2H), 7.31 (d, J=8.3 Hz, 2H), 7.19-7.18 (m, 2H), 7.14 (ddd, J=4.4, 2.2, 1.0 Hz, 1H), 7.07-7.04 (m, 1H), 6.82 (s, 1H), 6.29 (d, J=7.8 Hz, 1H), 5.94-5.88 (m, 1H), 5.31 (d, J=17.7 Hz, 1H), 5.22 (d, J=10.5 Hz, 1H), 5.14-5.04 (m, 3H), 4.62 (dt, J=16.7, 7.6 Hz, 3H), 4.38 (d, J=16.9 Hz, 1H), 4.16 (q, J=7.1 Hz, 2H), 4.11 (t, J=6.0 Hz, 2H), 3.98 (t, J=6.5 Hz, 1H), 3.81 (s, 3H), 3.65 (bs, 2H), 3.11 (dd, J=16.1, 6.4 Hz, 1H), 2.82 (bd, J=15.1 Hz, 1H), 2.53 (t, J=7.5 Hz, 2H), 2.18 (dq, J=13.0, 6.2 Hz, 3H), 1.27 (t, J=7.1 Hz, 3H), 0.97 (dd, J=18.8, 6.8 Hz, 6H), 0.82 (s, 9H), -0.03 (d, J=4.7 Hz, 6H).
LC/MS: retention time 4.27 min. (ESI) $C_{50}H_{69}N_5O_{12}SiNa$: [M+Na]$^+$ 982; found 982.

3.8 Ethyl 4-(5-(((((4-((S)-2-((S)-2-(((allylozy)carbonyl)amino)-3-methylbutanamido-propanamido)-benzyl)-oxy)-carbonyl)-amino)-4-((S)-3-(hydroxymethyl)-1,2,3,4-tetrahydroisoquinoline-2-carbonyl)-2-methoxyphenoxy)butanoate (16)

To a solution of ethyl 4-(5-((((4-((S)-2-((S)-2-(((allyloxy)carbonyl)amino)-3-methylbutanamido)-propanamido)-benzyl)-oxy)-carbonyl)amino)-4-((S)-3-(((tert-butyldimethylsilyl)oxy)methyl)-1,2,3,4-tetrahydroisoquinoline-2-carbonyl)-2-methoxyphenoxy)butanoate (15) (457 mg, 0.476 mmol), under Ar, in anhydrous THF (4.2 mL), added AcOH (55 μL, 0.952 mmol) then TBAF (0.83 mL of a 1.0 M solution in THF, 0.83 mmol) and the reaction was stirred at 22° C. for 22 hr. The reaction mixture was diluted with EtOAc (10 mL) and the organics were washed with $H_2O$, $NaHCO_3$(sat), and brine (each, 1×5 mL), then dried over $MgSO_4$, filtered and concentrated. The residue was purified via column chromatography (20→100% EtOAc in hexane) to afford 16 (385 mg, 96% yield).
$^1$H NMR (500 MHz; CDCl$_3$): δ 8.42 (bs, 1H), 8.05 (bs, 1H), 7.67 (bs, 1H), 7.51 (d, J=7.6 Hz, 2H), 7.29 (d, J=8.0 Hz, 2H), 7.19 (t, J=3.2 Hz, 2H), 7.14 (bs, 1H), 7.04 (bs, 1H), 6.76 (s, 1H), 6.46 (bs, 1H), 5.90 (bs, 1H), 5.31 (d, J=17.5 Hz, 1H), 5.23 (d, J=10.7 Hz, 2H), 5.08 (s, 2H), 4.65-4.56 (m, 3H), 4.36 (d, J=16.4 Hz, 2H), 4.15 (q, J=7.1 Hz, 2H), 4.10 (s, 2H), 3.99 (t, J=6.3 Hz, 1H), 3.79 (s, 3H), 3.63 (t, J=8.8 Hz, 1H), 3.17-3.12 (m, 1H), 2.72 (bs, 1H), 2.53 (t, J=7.4 Hz, 2H), 2.17 (t, J=6.3 Hz, 3H), 1.45 (d, J=6.9 Hz, 3H), 1.27 (t, J=7.1 Hz, 3H), 0.95 (dd, J=22.0, 6.8 Hz, 6H).
LC/MS: retention time 3.05 min. (ESI) $C_{44}H_{56}N_5O_{12}$: [M+H]$^+$ 846; found 846.

3.10 4-((S)-2-((S)-2-(((allyloxy)carbonyl)amino)-3-methylbutanamido)propanamido)benzyl (6aS)-3-(4-ethoxy-4-oxobutoxy)-6-hydroxy-2-methoxy-14-oxo-6,6a,7,12-tetrahydrobenzo[5,6][1,4]diazepino[1,2-b]isoquinoline-5(14H)-carboxylate (17)

To a solution of ethyl 4-(5-((((4-((S)-2-((S)-2-(((allyloxy)carbonyl)amino)-3-methylbutanamido)-propanamido)-benzyl)-oxy)-carbonyl)-amino)-4-((S)-3-(hydroxymethyl)-1,2,3,4-tetrahydroisoquinoline-2-carbonyl)-2-methoxyphenoxy)butanoate (16) (253 mg, 0.299 mmol) in DCM (3.0 mL), under Ar, added Dess-Martin periodinane (190 mg, 0.449 mmol). The resulting mixture was stirred at 22° C. for 3 hr, then quenched with 3 mL of 0.5 M $Na_2S_2O_3$, diluting with DCM (5 mL). The mixture was stirred for 5 min, then added 3 mL of aqueous $NaHCO_3$(sat) and stirred for an additional 5 min before extracting with DCM (3×5 mL). The combined organics were dried over $MgSO_4$, filtered and concentrated. The residue was purified via column chromatography (0→10% MeOH in DCM) to afford 17 (222 mg, 88% yield).

$^1$H NMR (500 MHz; $CDCl_3$): δ 8.48 (bs, 1H), 7.55-7.53 (m, 2H), 7.28 (s, 3H), 7.19-7.18 (m, 3H), 6.82-6.79 (m, 1H), 6.32 (bs, 1H), 5.90 (bs, 1H), 5.41 (d, J=10.9 Hz, 1H), 5.33-5.19 (m, 4H), 4.83 (d, J=15.7 Hz, 1H), 4.69-4.59 (m, 3H), 4.55 (d, J=15.9 Hz, 2H), 4.15 (q, J=7.1 Hz, 2H), 4.02 (dd, J=6.6, 5.9 Hz, 1H), 3.87 (s, 3H), 3.73-3.70 (m, 2H), 3.32 (bs, 1H), 3.16 (dd, J=15.1, 2.6 Hz, 1H), 3.07 (dd, J=15.0, 5.4 Hz, 1H), 2.44-2.38 (m, 2H), 2.24-2.20 (m, 1H), 1.97 (bs, 2H), 1.46 (d, J=6.8 Hz, 3H), 1.27 (t, J=7.1 Hz, 3H), 0.98 (dd, J=27.7, 6.8 Hz, 6H).

LC/MS: retention time 2.97 min. (ESI) $C_{44}H_{54}N_5O_{12}$: [M+H]$^-$ 844; found 844.

3.11 4-(((6aS)-5-(((4-((S)-2-((S)-2-(((allyloxy)carbonyl)amino)-3-methylbutanamido)-propanamido)-benzyl)-oxy)carbonyl)-6-hydroxy-2-methoxy-14-oxo 5,6,6a,7,12,14-hexahydrobenzo[5,6][1,4]diazepino[1,2-b]isoquinolin-3-yl)oxy)butanoic acid (18)

To a solution of 4-((S)-2-((S)-2-(((allyloxy)carbonyl)amino)-3-methylbutanamido)propanamido)benzyl (6aS-3-(4-ethoxy-4-oxobutoxy)6-hydroxy-2-methoxy-14-oxo-6,6a,7,12-tetrahydrobenzo[5,6][1,4]diazepino[1,2-b]isoquinoline-5(14H)-carboxylate (17) (222 mg, 0.263 mmol) in 3:1:1 THF/MeOH/$H_2O$ (2.2 mL) added LiOH (31.6 mg, 1.32 mmol). The resulting mixture was stirred at 22° C. for 1 hr, then quenched with 5% citric acid$_{(aq)}$ (5 mL) and extracted with 2-MeTHF (3×5 mL). Combined organics were concentrated and purified via column chromatography (0→10% MeOH, containing 0.1% HOAc, in DCM) to afford 18 (162 mg, 76% yield).

$^1$H NMR (500 MHz; CD3OD): δ 7.49 (d, J=8.2 Hz, 2H), 7.26 (d, J=7.1 Hz, 4H), 7.15-7.10 (m, 2H), 6.99-6.75 (m, 1H), 6.63 (s, 1H), 5.90 (ddt, J=16.7, 10.9, 5.5 Hz, 1H), 5.29-5.25 (m, 2H), 5.14 (d, J=10.4 Hz, 2H), 4.77-4.72 (m, 2H), 4.52-4.45 (m, 4H), 4.03 (s, 1H), 3.92 (d, J=5.8 Hz, 2H), 3.84 (s, 3H), 3.74 (bs, 1H), 3.60 (bs, 1H), 3.09 (d, J=3.2 Hz, 2H), 2.48-2.38 (m, 2H), 2.00 (bd, J=42.2 Hz, 3H), 1.40 (d, J=4.9 Hz, 3H), 0.94 (dd, J=17.7, 6.2 Hz, 6H).

LC/MS: retention time 2.67 min. (ESI) $C_{42}H_{50}N_5O_{12}$: [M+H]$^+$ 816; found 816.

3.12 4-((S)-2-((S)-2-(((allyloxy)carbonyl)amino)-3-methylbutanamido)propanamido)benzyl (6aS)-3-(4-((S)-5-((bis(allyloxy)phosphoryl)oxy)-1-(chloromethyl)-1,2-dihydro-3H-benzo[e]indol-3-yl)-4-oxobutoxy)-6-hydroxy-2-methoxy-14-oxo-6,6a,7,12-tetrahydrobenzo[5,6][1,4]diazepino[1,2-b]isoquinoline-5(14H)-carboxylate (19a)

Crude 7a (0.05 mmol), 18 (0.02 mmol) and DIEA (0.035 mL, 0.1 mmol) were dissolved in anhydrous DMF (0.2 mL). HATU (30 mg, 0.08 mmol) was added and the mixture was stirred overnight. The reaction mixture was not worked up and used as is in the next step.

3.13 4-((S)-2-((S)-2-amino-3-methylbutanamido)propanamido)benzyl (6aS)-3-(4-((S)-1-(chloromethyl)-5-(phosphonooxy)-1,2-dihydro-3H-benzo[e]indol-3-yl)-4-oxobutoxy)-6-hydroxy-2-methoxy-14-oxo-6,6a,7,12-tetrahydrobenzo[5,6][1,4]diazepino[1,2-b]isoquinoline-5(14H)-carboxylate (20a)

Reaction mixture of 19a was diluted with DMF (1 mL) and pyrrolidine (0.008 mL, 0.1 mmol) was added followed by palladium tetrakis triphenylphosphine (5.6 mg, 0.005 mmol). After 30 minutes reaction mixture was purified on EZ Prep (Gemini 30×150 mm column) (5→95% ACN in $H_2O$, each containing 0.05% TFA) to afford 20a (20.5 mg, 99% yield), contains unknown impurities. Used as is in the next step.

LC/MS: retention time 2.56 min. (ESI) $C_{51}H_{57}ClN_6O_{13}P$: [M+H]$^+$ 1027; found 1027.

3.14 4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl (6aR-3-(4-((S)-1-(chloromethyl)-5-(phosphonooxy)-1,2-dihydro-3H-benzo[e]indol-3-yl)-4-oxobutoxy)-6-hydroxy-2-methoxy-13-oxo-6,6a,7,12,12a,13-hexahydro-5H-benzo[b]naphtho[2,3-e]azepine-5-carboxylate (21a/D826)

Crude 20a (20.5 mg, 0.02 mmol) was dissolved DMF (0.4 mL) and DIEA (0.01 mL, 0.06 mmol) was added followed by MAL-dPEG®8-NHS ester (20.7 mg, 0.03 mmol). After 2 hr, the reaction mixture was directly loaded and purified on EZ Prep (Gemini 30×150 mm column) (5→95% ACN in $H_2O$, each containing 0.05% TFA) to afford 21a (3.9 mg, 12% yield).

LC/MS: retention time 2.42 min. (ESI) $C_{77}H_{98}ClN_8O_{25}PNa$: [M+Na]$^+$ 1624; found 1624.

3.15 4-((S)-2-((S)-2-(((allyloxy)carbonyl)amino)-3-methylbutanamido)propanamido)benzyl (6aS)-3-(4-((S)-1-(chloromethyl)-5-((methoxycarbonyl)oxy)-1,2-dihydro-3H-benzo[e]indol-3-yl)4-oxobutoxy)-6-hydroxy-2-methoxy-14-oxo-6,6a,7,12-tetrahydrobenzo[5,6][1,4]diazepino[1,2-b]isoquinoline-5(14H)-carboxylate (19b)

Crude 7b (0.04 mmol), 18 (0.03 mmol) and DIEA (0.027 mL, 0.16 mmol) were dissolved in anhydrous DMF (0.2 mL). HATU (60 mg, 0.16 mmol) was added and the mixture was stirred overnight. The reaction mixture was directly loaded and purified via reverse phase chromatography (0→100% ACN in $H_2O$, each containing 0.05% HOAc) to afford 19b (16.4 mg, 48% yield).

LC/MS: retention time 3.38 min. (ESI) $C_{57}H_{61}ClN_6O_{14}Na$: [M+Na]$^+$ 1111; found 1111.

3.16 4-((S)-2-((S)-2-amino-3-methylbutanamido)propanamido)benzyl (6aS)-3-(4-((S)-1-(chloromethyl)-5-((methoxycarbonyl)oxy)-1,2-dihydro-3H-benzo[e]indol-3-yl)-4-oxobutoxy)-6-hydroxy-2-methozy-14-oxo-6,6a,7,12-tetrahydrobenzo[5,6][1,4]dizepino[,2-b]isoquinoline-5(14H)-carboxylate (20b)

To a solution of 19b in DCM (2 mL), under Ar, $Bu_3SnH$ (0.005 mL, 0.02 mmol) was added followed by palladium tetrakis triphenylphosphine (8 mg, 0.007 mmol). After 30 minutes reaction mixture was concentrated, dissolved in DMSO (1 mL) and purified via reverse phase chromatography (0→100% ACN in H$_2$O, each containing 0.05% HOAc) to afford 20b (7.7 mg, 52% yield).

LC/MS: retention time 2.53 min. (ESI) C$_{53}$H$_{58}$ClN$_6$O$_{12}$: [M+H]$^+$ 1005; found 1005.

3.17 4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl (6aS)-6-hydroxy-3-(4-((S)-5-hydroxy-1-(hydroxymethyl)-1,2-dihydro-3H-benzo[e]indol-3-yl)-4-oxobutoxy)-2-methoxy-14-oxo-6,6a,7,12-tetrahydrobenzo[5,6][1,4]diazepino[1,2-b]isoquinoline-5(14H)-carboxylate (21b/D824)

To a solution of 20b (7.2 mg, 0.007 mmol) in DMF (0.1 mL) added DIEA (0.003 mL, 0.02 mmol) then MAL-dPEG®8-NHS ester (9.9 mg, 0.014 mmol). After 3 hr, the reaction mixture was directly loaded and purified via reverse phase chromatography (0→100% ACN in H$_2$O, each containing 0.05% HOAc) to afford 21b (1.6 mg, 14% yield), with an additional less pure fraction of 21b (containing 1% 20b) (2.3 mg, 20% yield).

LC/MS: retention time 3.05 min. (ESI) C$_{79}$H$_{99}$ClN$_8$O$_{24}$Na: [M+Na]$^+$ 1601; found 1601.

3.18 4-((S)-2-((S)-2-(((allyloxy)carbonyl)amino)-3-methylbutanamido)propanamido)benzyl (6aS)-3-(4-((S)-1-(chloromethyl)-5-((4-methylpiperazine-1-carbonyl)oxy)-1,2-dihydro-3H-benzo[e]indol-3-yl)-4-oxobutoxy)-6-hydroxy-2-methoxy-14-oxo-6,6a,7,12-tetrahydrobenzo[5,6][1,4]diazepino[1,2-b]isoquinoline-5(14H)-carboxylate (19c)

Crude 7c (0.04 mmol), 18 (0.03 mmol) and DIEA (0.028 mL, 0.16 mmol) were dissolved in anhydrous DMF (0.2 mL). HATU (61 mg, 0.16 mmol) was added and the mixture was stirred overnight. The reaction mixture was directly loaded and purified via reverse phase chromatography (0→100% ACN in H$_2$O, each containing 0.05% HOAc) to afford 19c (16.0 mg, 40% yield), contaminated with acid 18.

LC/MS: retention time 2.63 min. (ESI) C$_{61}$H$_{70}$ClN$_8$O$_{13}$: [M+H]$^+$ 1157; found 1157.

3.19 4-((S)-2-((S)-2-amino-3-methylbutanamido)propanamido)benzyl (6aS)-3-(4-((S)-1-(chloromethyl)-5-((4-methylpiperazine-1-carbonyl)oxy)-1,2-dihydro-3H-benzo[e]indol-3-yl)-4-oxobutoxy)-6-hydroxy-2-methoxy-14-ozo-6,6a,7,12-tetrahydrobenzo[5,6][1,4]diazepino[1,2-b]isoquinoline-5(14H)-carboxylate (20c)

To a solution of impure 19c (16 mg, 0.15 mmol) in Dioxane/THF/H$_2$O (0.4 mL), added successively Et$_3$N (0.014 mL, 0.096 mmol), formic acid (0.014 mL, 0.36 mmol), PPh$_3$ (1.3 mg, 0.0048 mmol) and palladium tetrakis triphenylphosphine (1.3 mg, 0.001 mmol). After 16 hr, added additional palladium tetrakis triphenylphosphine (2 mg, 0.002 mmol) and stirred an additional 3 hr. The reaction mixture was concentrated, dissolved in DMSO (1 mL) and purified EZ Prep (Gemini 30×150 mm column) (5→95% ACN in H$_2$O, each containing 0.05% HOAc) to afford 20c (16 mg) containing unknown amount of impurity.

LC/MS: retention time 2.16 min. (ESI) C$_{57}$H$_{65}$ClN$_8$O$_{11}$Na: [M+Na]$^+$ 1095; found 1095.

3.20 4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl (6aS)-3-(4-((S)-1-(chloromethyl)-5-((4-methylpiperazine-1-carbonyl)oxy)-1,2-dihydro-3H-benzo[e]indol-3-yl)-4-oxobutoxy)-6-hydroxy-2-methoxy-14-oxo-6,6a,7,12-tetrahydrobenzo[5,6][1,4]diazepino[1,2-b]isoquinoline-5(14H)-carboxylate (21c/D828)

Crude 20c (16 mg, 0.015 mmol) was dissolved DMF (0.2 mL) and pyridine (0.003 mL, 0.04 mmol) was added followed by a solution of MAL-dPEG®8-NHS ester (20.5 mg, 0.03 mmol) in DMF (0.05 mL). After 45 min, the reaction was stored in freezer for 18 hr, then directly loaded and purified on EZ Prep (Gemini 30×150 mm column) (30→60% ACN in H$_2$O, each containing 0.05% HOAc) to afford 21c (4.8 mg, 20% yield).

LC/MS: retention time 2.41 min. (ESI) C$_{83}$H$_{108}$ClN$_{10}$O$_{23}$: [M+H]$^+$ 1647; found 1647.

3.21 4-((S)-2-((S)-2-amino-3-methylbutanamido)propanamido)benzyl (6aS)-3-(4-((S)-1-(chloromethyl)-5-hydroxy-1,2-dihydro-3H-benzo[e]indol-3-yl-4-oxobutoxy)-6-hydroxy-2-methoxy-14-oxo-6,6a,7,12-tetrahydrobenzo[5,6][1,4]diazepino[1,2-b]isoquinoline-5(14H)-carboxylate (20d)

To a solution of 19b (10.3 mg, 0.0095 mmol) in DCM (0.5 mL), under Ar, pyrrolidine (0.001 mL, 0.014 mmol) was added followed by palladium tetrakis triphenylphosphine (0.6 mg, 0.0005 mmol). After 30 minutes, the reaction mixture was concentrated, dissolved in DMSO (0.5 mL) and purified via reverse phase chromatography (0→100% ACN in H$_2$O, each containing 0.05% HOAc). Desired fractions were lyophilized to afford 20d (5.8 mg, 65% yield).

LC/MS: retention time 2.59 min. (ESI) C$_{51}$H$_{56}$ClN$_6$O$_{10}$: [M+H]$^+$ 947; found 947.

3.22 4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl (6aS)-6-hydroxy-3-(4-((S)-5-hydroxy-1-(hydroxymethyl)-1,2-dihydro-3H-benzo[e]indol-3-yl)4-oxobutoxy)-2-methoxy-14-oxo-6,6a,7,12-tetrahydrobenzo[5,6][1,4]diazepino[1,2-b]isoquinoline-5(14H)-carboxylate (21d/D822)

To a solution of 20d (5.4 mg, 0.006 mmol) in DMF (0.1 mL) added pyridine (0.0012 mL, 0.014 mmol) then MAL-dPEG®8-NHS ester (7.9 mg, 0.011 mmol). After 3 hr, the reaction mixture was directly loaded and purified via reverse phase chromatography (0→100% ACN in H$_2$O, each containing 0.05% HOAc) to afford 21d (0.5 mg, 6% yield, 93% pure @ 254 nm), with an additional less pure fraction of 21d (1.6 mg, 18% yield, 89% pure @ 254 nm).

LC/MS: retention time 2.99 min. (ESI) C$_{77}$H$_{97}$ClNO$_{22}$Na: [M+Na]$^+$ 1543; found 1543.

Example 5—Preparation of 3G7-(IQB-CBI) (Antibody-Drug Conjugate)

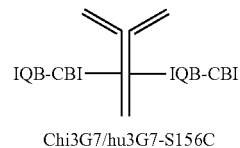

Chimeric and humanized, cys-substituted (S156C), anti-IL1RAP antibody ("Chi3G7/hu3G7-IQB-CBI") (5.0 mg, 1.68 mg/mL, PBS) was exchanged into borate buffer (50 mM, pH 8.5, 1 mM diethylene triamine pentaacetic acid (DTPA)) via 2 cycles of molecular weight cut-off filtration (MWCO) using a Millipore, 15 mL, 30 kDa device. To the new solution of the 3G7-S156C-CYSMAB antibody (5.0 mg/mL, borate buffer (50 mM, pH 8.5, 1 mM DTPA)) was added a solution of Dithiothreitol (DTT) (33 µL, 50.0 equiv., 50 mM) and the resultant solution was shaken gently overnight. Antibody 3G7 has amino acid sequences as described herein.

Complete reduction of the interchain disulfide bridges and removal of the S156C cysteine/glutathione adducts was confirmed by rp-LCMS as described earlier (Junutula et al., 2008, Nature Biotech, 26, 925-932). DTT was then removed from the solution via 3 cycles of molecular weight cut-off filtration (MWCO) using a Millipore, 15 mL, 30 kDa device, using PBS as the exchange buffer. To a 5 mg/ml solution of the fully reduced 3G7-S156C -CYSMAB antibody was added a solution of dehydro ascorbic acid (dhAA) (33 µL, 50.0 equiv., 50 mM). The resultant solution was shaken gently for 3 hrs. The re-oxidation was monitored via rp-LCMS. Once the re-oxidation was deemed complete, the reaction mixture was diluted up to 50% v/v with propylene glycol and IQB-CBI was added as a solution in DMSO (10.0 equiv., 10 mM in DMSO). The reaction was allowed to stir at ambient temperature for 1 hr. The mixture was then treated with activated charcoal for 1 hr at ambient temperature. The activated charcoal was then removed via filtration. The conjugate was then exchanged into PBS via multiple cycles of molecular weight cut-off filtration (MWCO) using Millipore, 15 mL, 30 kDa devices. The solution was then subjected to a sterile filtration to yield the desired conjugate (0.974 mL, 2.16 mg/mL). Volume: 0.974 mL. Concentration: 2.16 mg/mL ($A_{280}$=0.145, 20-fold dilution). Drug to Antibody Ratio (DAR) is in the range of 1.7-2.0 (determined by rp-LCMS). The monomeric form of ADC is confirmed by size exclusion chromatography (SEC): 96%. Characterization data is provided in Table 1, below.

TABLE II

| | DAR by HIC | | HMWS (%) by SEC | |
|---|---|---|---|---|
| | hu3G7 | C0 | hu3G7 | C0 |
| D822 | 1.75 | 2.09 | 2.4 | 4.9 |
| D824 | 1.21 | 1.89 | 2.1 | 9.6 |
| D826 | 1.87 | 2.01 | 2.7 | 2.6 |
| D828 | 1.74 | 1.69 | 5.5 | 4.0 |

Example 6—Binding of 3G7-(IQB-CBI ADCs to Cells: D816, D818, D820, D822, D826, D824, D828

Figure 15:
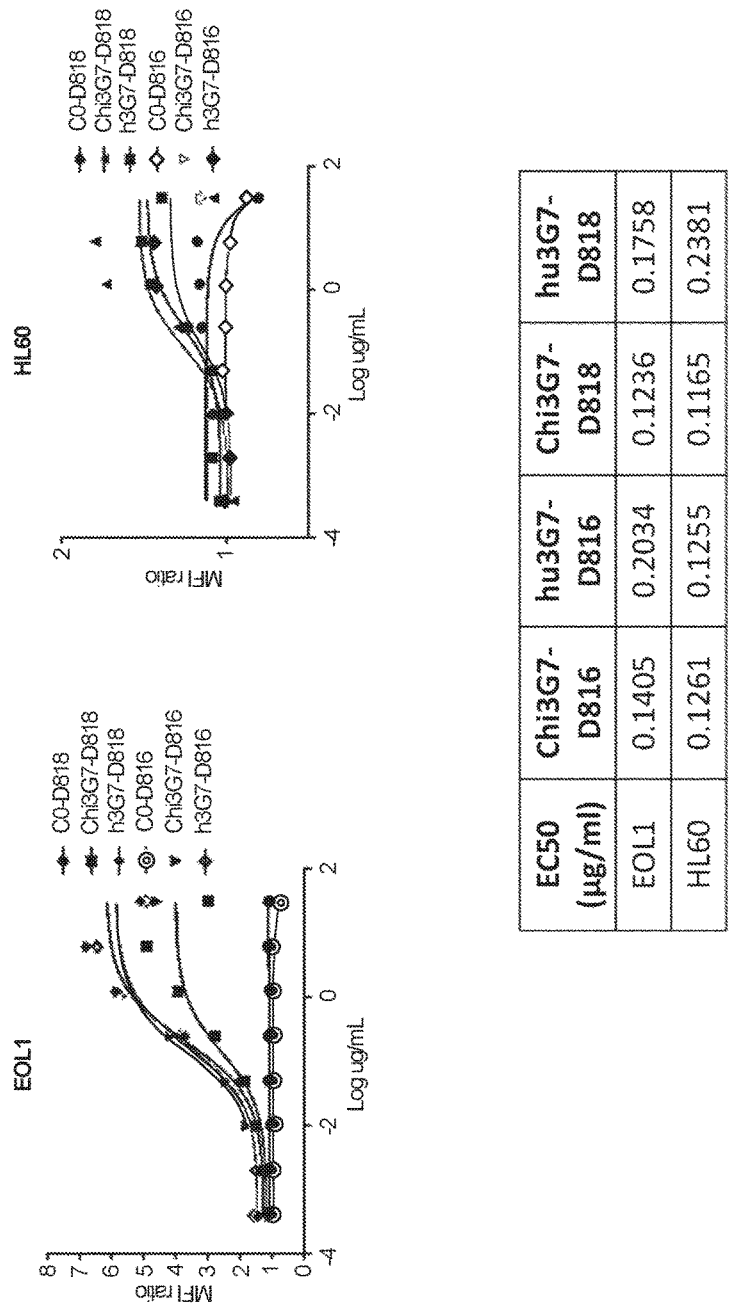
FIG. 15 shows results of a binding assay for IL1RAP-IQB-CBI dimer (D816-D820)-ADCs.
Figure 16:
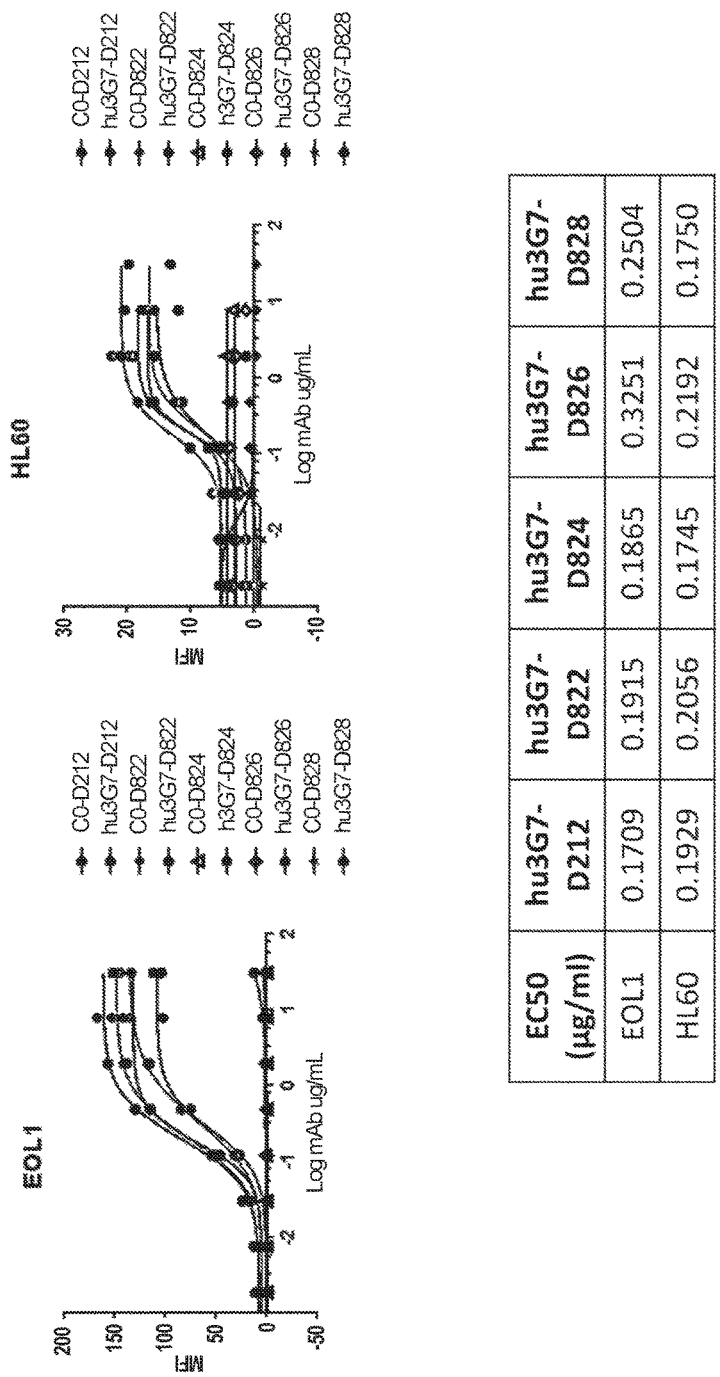
FIG. 16 shows results of a binding assay for IL1RAP-IQB-CBI dimer (D822, D824, D826,D828)-ADCs.

FIGS. 15 and 16 show binding, as a function of mean fluorescent intensity, of humanized (hu3G7) or chimeric (Chi3G7) anti-IL1RAP antibody to various cell lines. HL-60 cells (human promyelocytic leukemia cells), EOL1 cells (human eosinophilic leukemia cells) and SK-MEL-5 cells (human melanoma cell line) express IL1RAP, and EOL1 cells do so with high expression. C0 antibody is a non-binding control IgG1. D212 is a composition having the formula:

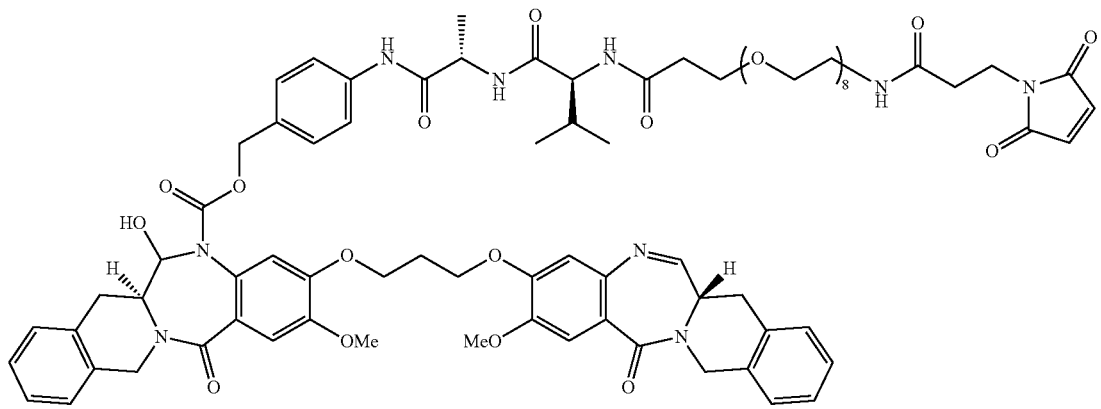

The cells were resuspended in binding buffer (PBS, 2% FBS)) containing 5% NHS (normal human serum) to $2 \times 10^6$ cells/mL. To 50 µL of cells, 50 µL of primary antibody/ADC was added and incubated at 4° for 30 min. After incubation, cells were wasked with binding buffer 2 times and then resuspended and incubated with second antibody (anti-human APC, 1:400 in the binding buffer) at 4° for 30 min. Cells were washed with binding buffer and resuspended in 200 uL of binding buffer with propidium iodide. Cells were immediately applied to flow cytometry for analysis. Mean fluorescence intensity (MFI) of the stained sample was measured.

Example 7—Chi3G7-(IQB-CBI) ADC Selective Cytotoxicity: D816, D818, D820, D822, D826, D824, D828

The selectivity of ADCs comprising Chi3G7 anti-IL1RAP chimeric antibody (human constant domain, mouse variable domain) and various IQB-CBI dimer linker-payloads (D816, D818, D820, D822, D826, D824, D828) is shown in FIGS. 17-23. HL-60 cells, EOL1 cells and SK-MEL-5 cells (human melanoma cell line) were treated with the IL1RAP -selective cytotoxic antibody-drug conjugate, Chi3G7-(IQB-CBI) ADC and the control antibody-drug conjugate, C0-(IQB-CBI) ADC or C0-D212 ADC, at varying concentrations at 37° C. for five days.

Figure 17:
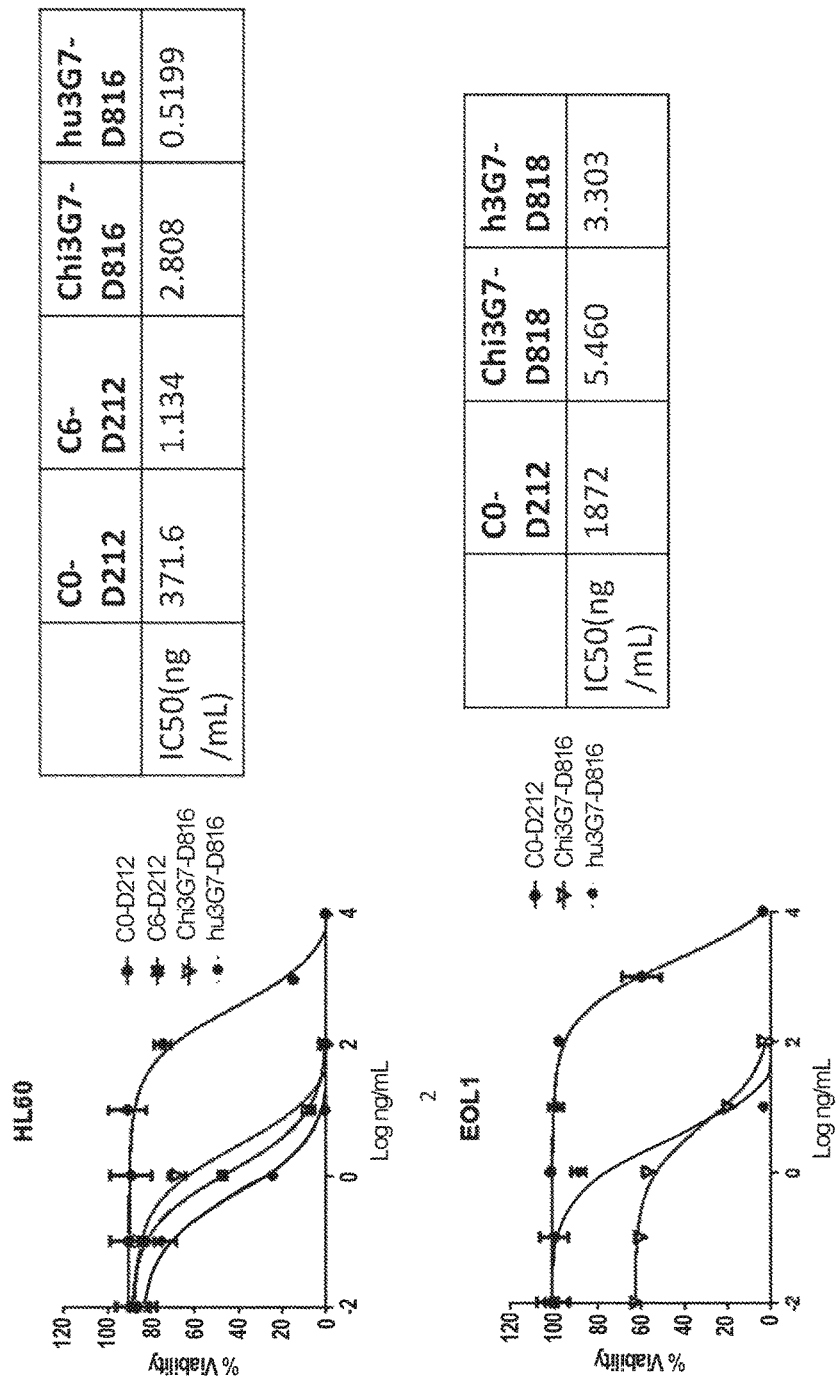
FIG. 17 shows target-dependent cell killing by an anti-IL1RAP-D816 ADC.

FIG. 17 shows target dependent cell killing by Chi3G7-D816 ADC, hu3G7-D816 (humanized), compared with control C0-D212 and C6-D212 ADC.

Figure 18:
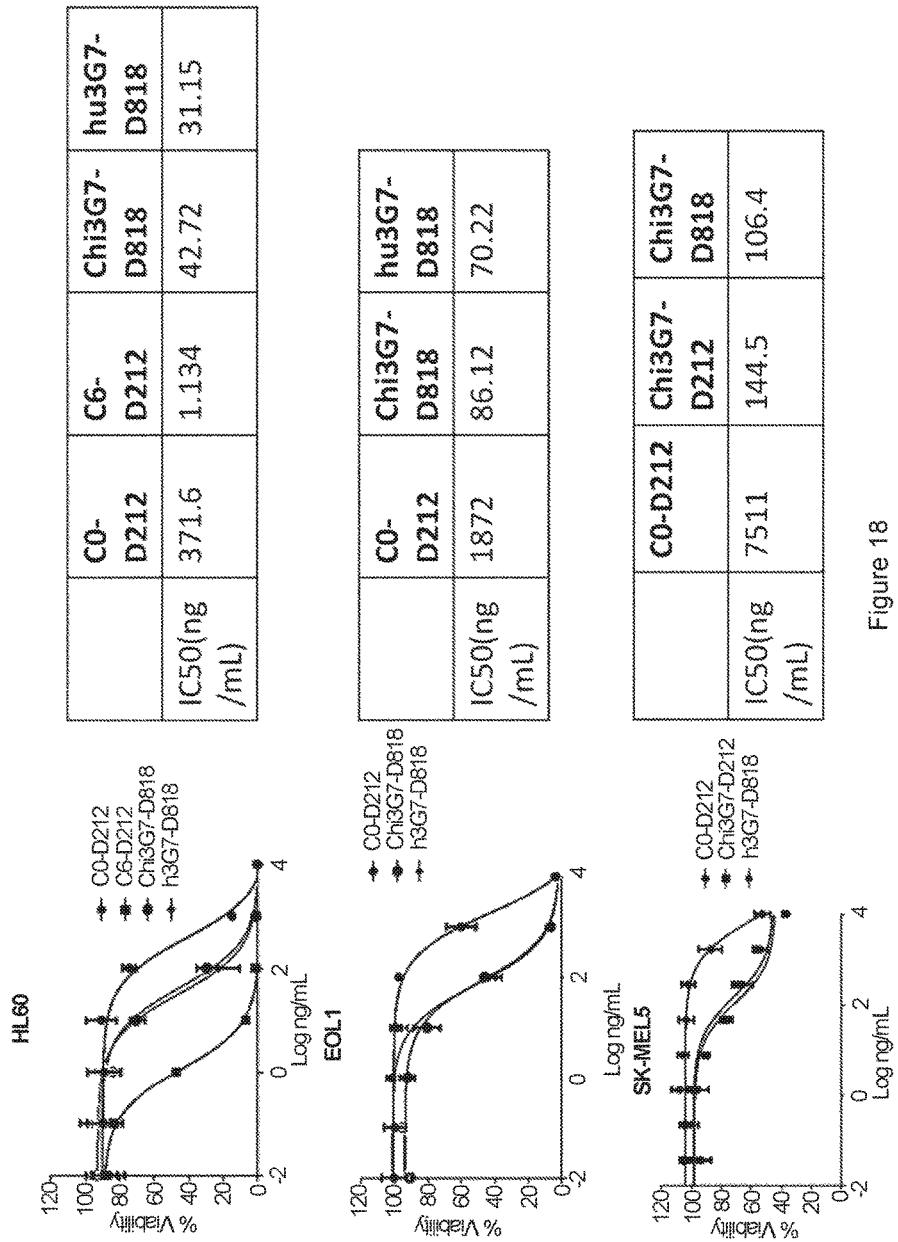
FIG. 18 shows target-dependent cell killing by an anti-IL RAP-D818 ADC.

FIG. 18 shows target dependent cell killing by Chi3G7-D818 ADC and hu3G7-D818 (humanized 3G7) compared with C0-D212 and C6-D212.

Figure 19:
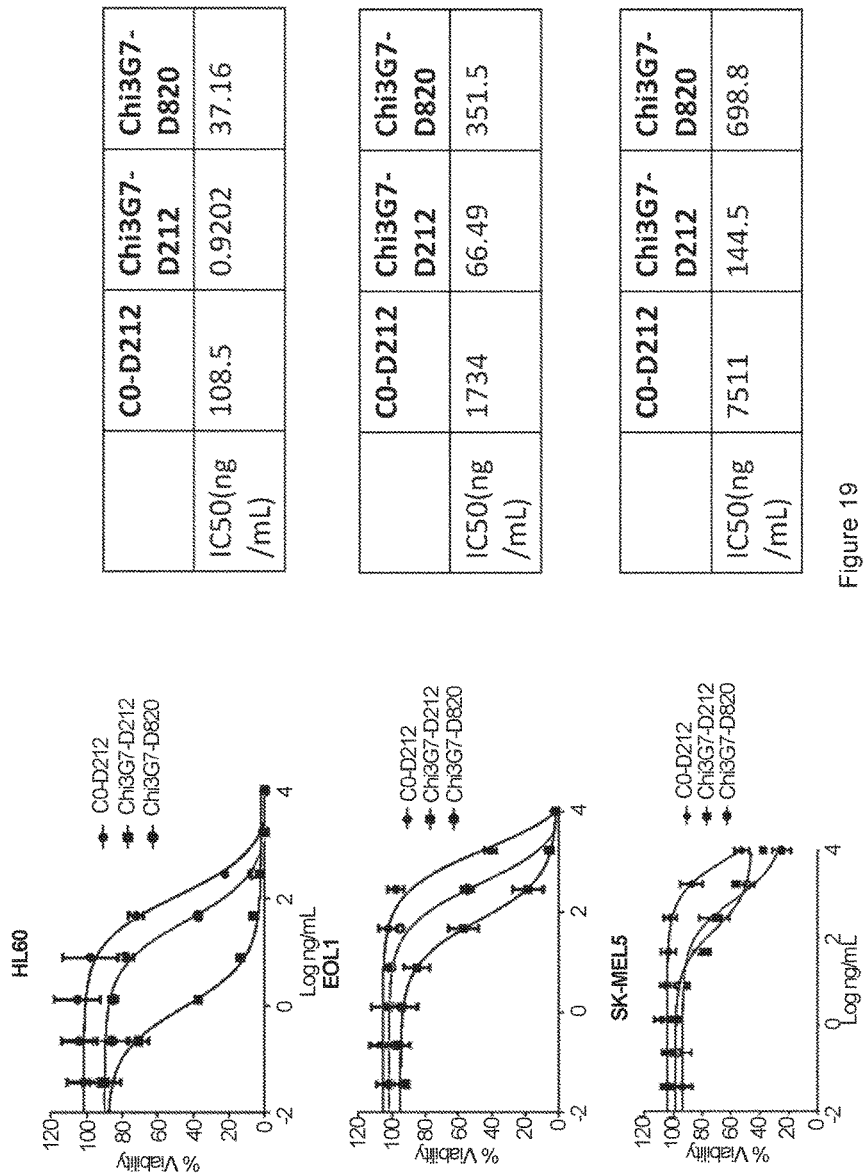
FIG. 19 shows target-dependent cell killing by an anti-IL1RAP-D820 ADC.
Figure 20:
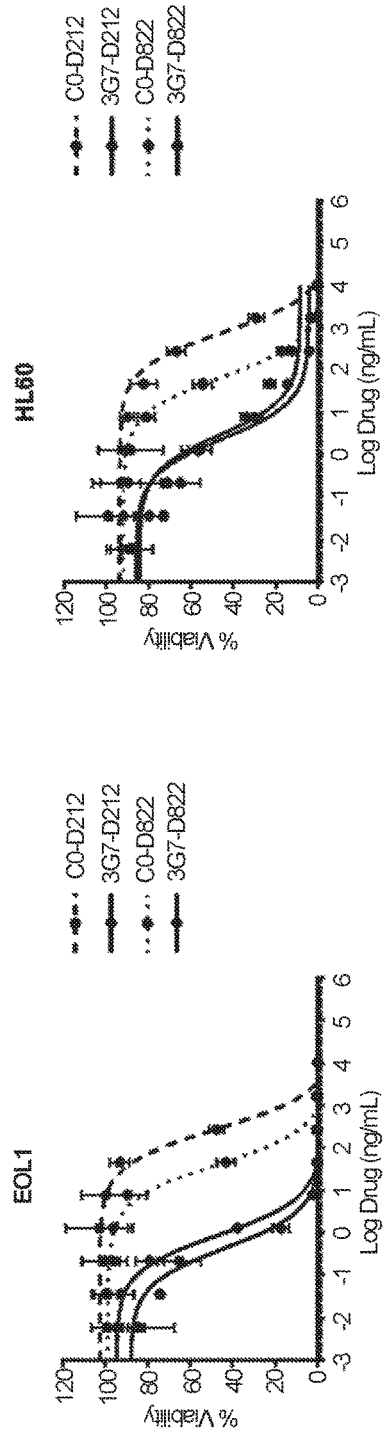
FIG. 20 shows target-dependent cell killing by an anti-IL1RAP-D822 ADC
Figure 21:
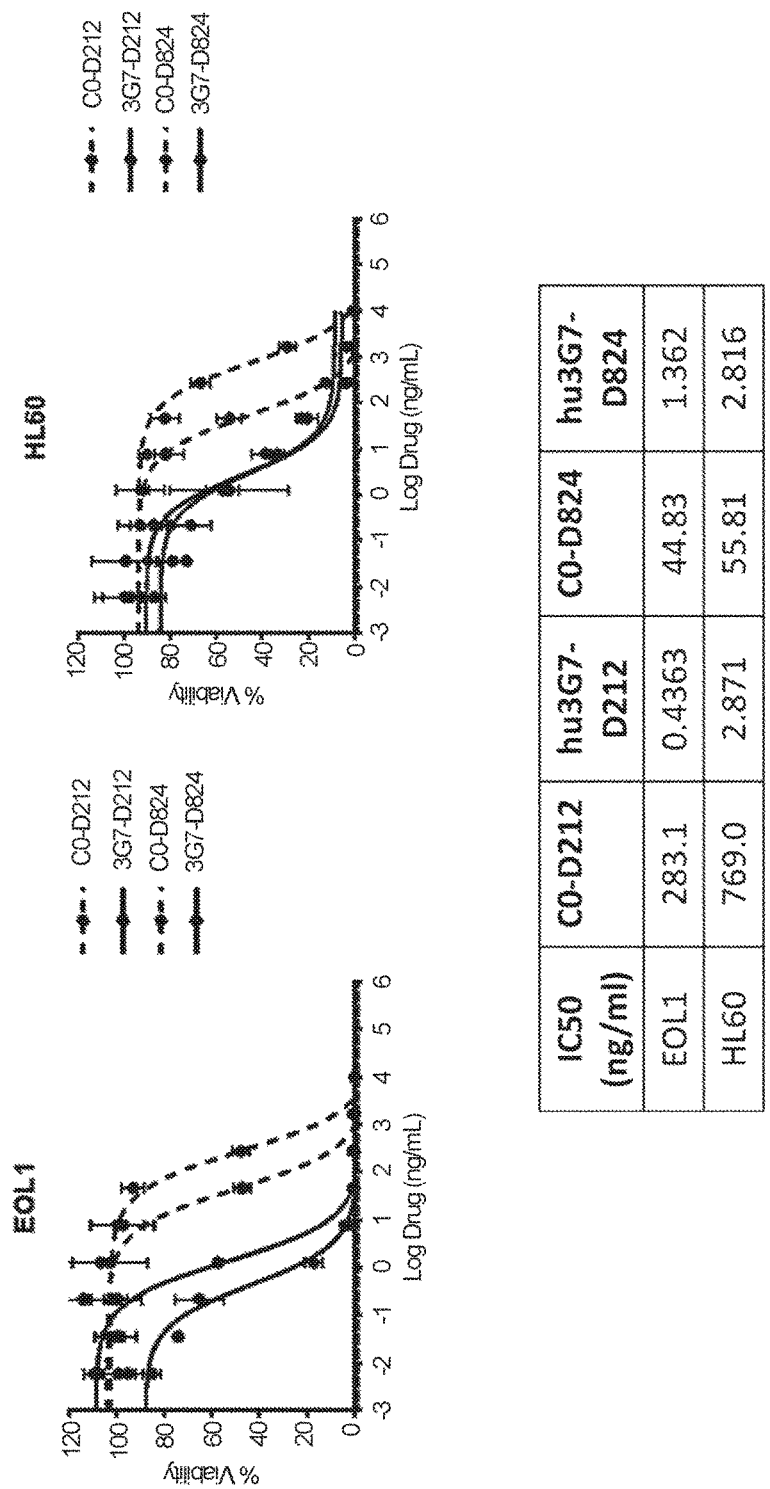
FIG. 21 shows target-dependent cell killing by an anti-IL1RAP-D824 ADC.
Figure 22:
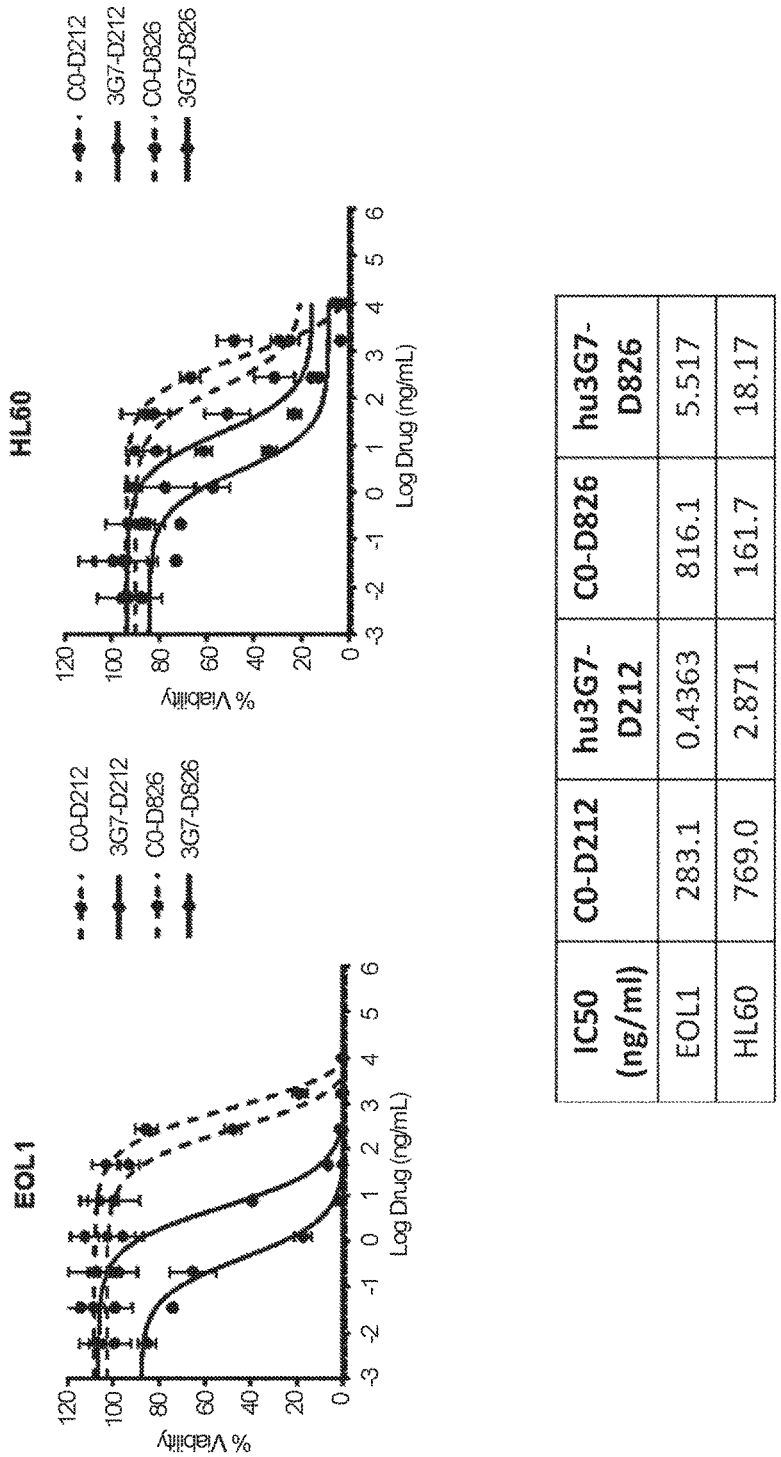
FIG. 22 shows target-dependent cell killing by an anti-IL1RAP-D826 ADC.
Figure 23:
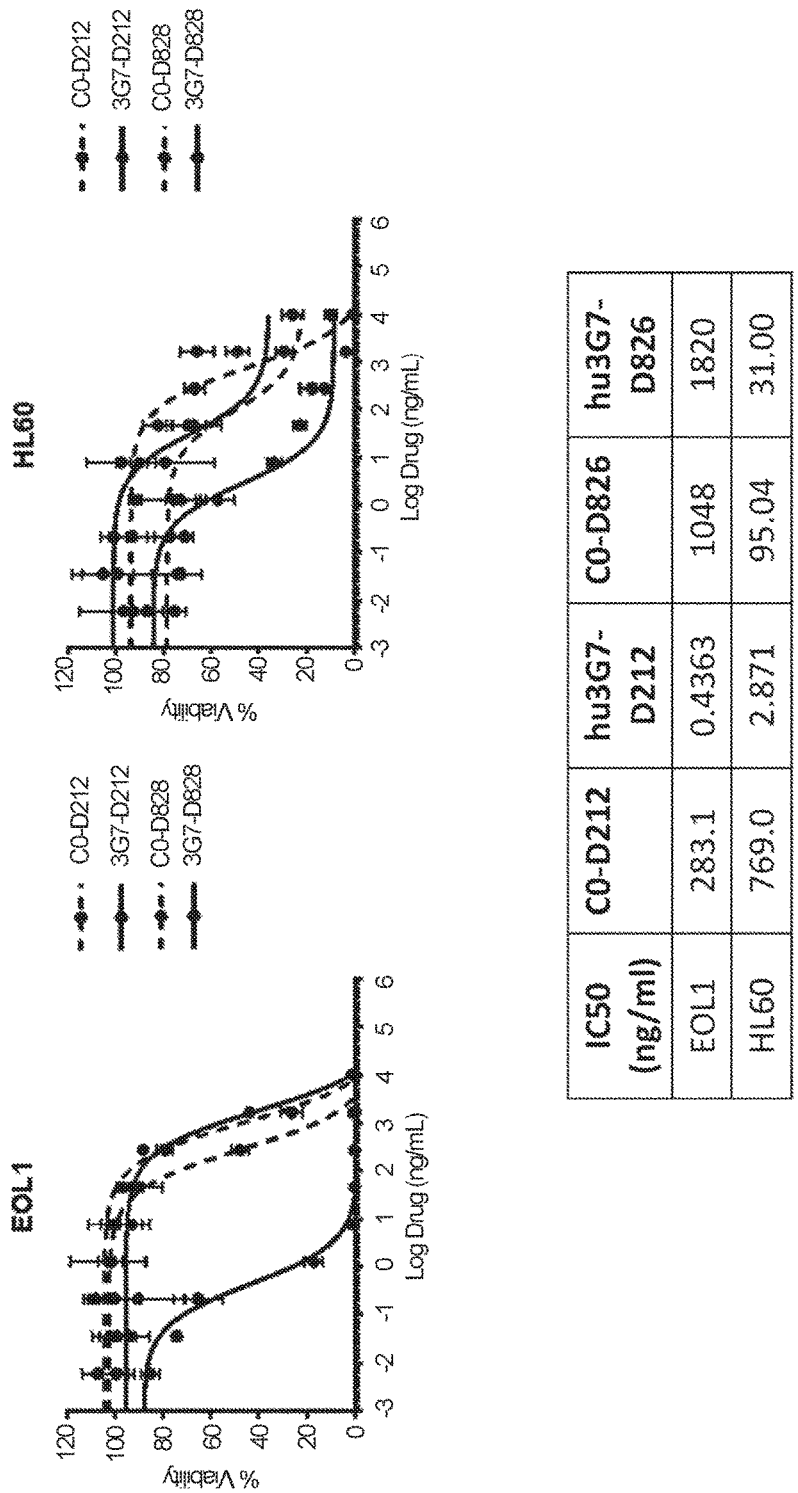
FIG. 23 shows target-dependent cell killing by an anti-IL RAP-D828 ADC.

FIG. 19 shows target dependent cell killing by Chi3G7-D820 ADC compared with C0-D212 and Chi3G7-D212

Example 8—Chi3G7-CLT-(IQB-CBI) ADC or Hu3G7-CLT-(IQB-CBI) ADC Target Dependent Cytotoxicity Cytotoxicity of Chi3G7-CLT-(IQB-CBI) or Hu3G7-CLT-(IQB-CBI) ADC and a non-binding control ADC were tested in cell lines expressing or not expressing IL1RAP. Results are shown in FIGS. 17-23. EOL1 cells express high copy number of IL1RAP, whereas HL60 and SK-MEL-5 cells express low copy number of IL1RAP. FIGS. 17-23 show that Chi3G7-CLT-(IQB-CBI) or Hu3G7-CLT-(IQB-CBI) ADC displayed target dependent killing compared to a non-binding C0-D212 or C0-CLT-(IQB-CBI) control ADC.

All publications and patent applications mentioned in this specification are herein incorporated by reference to the same extent as if each individual publication or patent application was specifically and individually indicated to be incorporated by reference.

While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

```
                        SEQUENCE LISTING

<160> NUMBER OF SEQ ID NOS: 6

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Leu Thr Cys Arg Ala Thr Gln Glu Leu Ser Gly Tyr
            20                  25                  30

Leu Ser Trp Leu Gln Gln Lys Pro Gly Lys Ala Ile Lys Arg Leu Ile
        35                  40                  45

Tyr Ala Ala Ser Thr Leu Asp Ser Gly Val Pro Ser Arg Phe Ser Gly
    50                  55                  60

Asn Arg Ala Gly Thr Asp Tyr Thr Leu Thr Ile Ser Ser Leu Gln Pro
65                  70                  75                  80

Glu Asp Phe Ala Thr Tyr Tyr Cys Leu Gln Tyr Ala Ile Tyr Pro Tyr
                85                  90                  95

Thr Phe Gly Gln Gly Thr Lys Leu Glu Ile Lys
            100                 105

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Phe Ile His Trp Val Arg Gln Ala Pro Gly Gln Gly Leu Glu Trp Ile
        35                  40                  45

Gly Phe Ile Asn Pro Tyr Asn Asp Gly Ser Lys Tyr Ala Gln Lys Phe
    50                  55                  60
```

```
Gln Gly Arg Ala Thr Leu Thr Ser Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Asp Asp Gly Tyr Tyr Gly Tyr Ala Met Asp Tyr Trp Gly Gln
            100                 105                 110

Gly Thr Leu Val Thr Val Ser Ser
        115                 120

<210> SEQ ID NO 3
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Asn Asn
             20                  25                  30

Leu His Trp Tyr Gln Gln Lys Pro Gly Gln Ala Pro Arg Leu Leu Ile
         35                  40                  45

Tyr Tyr Ala Ser Gln Ser Ile Ser Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Ser His Asn Trp Pro His
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Gln Ser Gly Ala Glu Val Lys Lys Pro Gly Ala
 1               5                  10                  15
```

Ser Val Lys Ile Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Lys Phe
    50                  55                  60

Gln Gly Arg Phe Thr Phe Thr Leu Asp Thr Ser Thr Ser Thr Ala Tyr
65                  70                  75                  80

Leu Glu Ile Arg Ser Leu Arg Ser Asp Asp Thr Ala Val Tyr Tyr Cys
                85                  90                  95

Ala Arg Tyr Tyr Gly Asn Phe Asp Tyr Trp Gly Gln Gly Thr Leu Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Cys Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly

```
                          435                 440                 445

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser His Asn Trp Pro His
                85                  90                  95

Thr Phe Gly Gly Gly Thr Lys Leu Glu Ile Lys Arg
            100                 105

<210> SEQ ID NO 6
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met His Trp Val Lys Gln Ser Pro Gly Glu Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Gly Phe Ser Leu Glu Thr Ser Ala Ser Ser Ala Tyr
65                  70                  75                  80

Leu Gln Ile Asn Asp Leu Lys Asn Glu Asp Met Ala Thr Tyr Phe Cys
                85                  90                  95

Ala Arg Tyr Tyr Gly Asn Phe Asp Tyr Trp Gly Gln Gly Thr Thr Leu
            100                 105                 110

Thr Val Ser Ser
            115
```

11. The compound according to claim 1, wherein G'-Rb' is selected from:
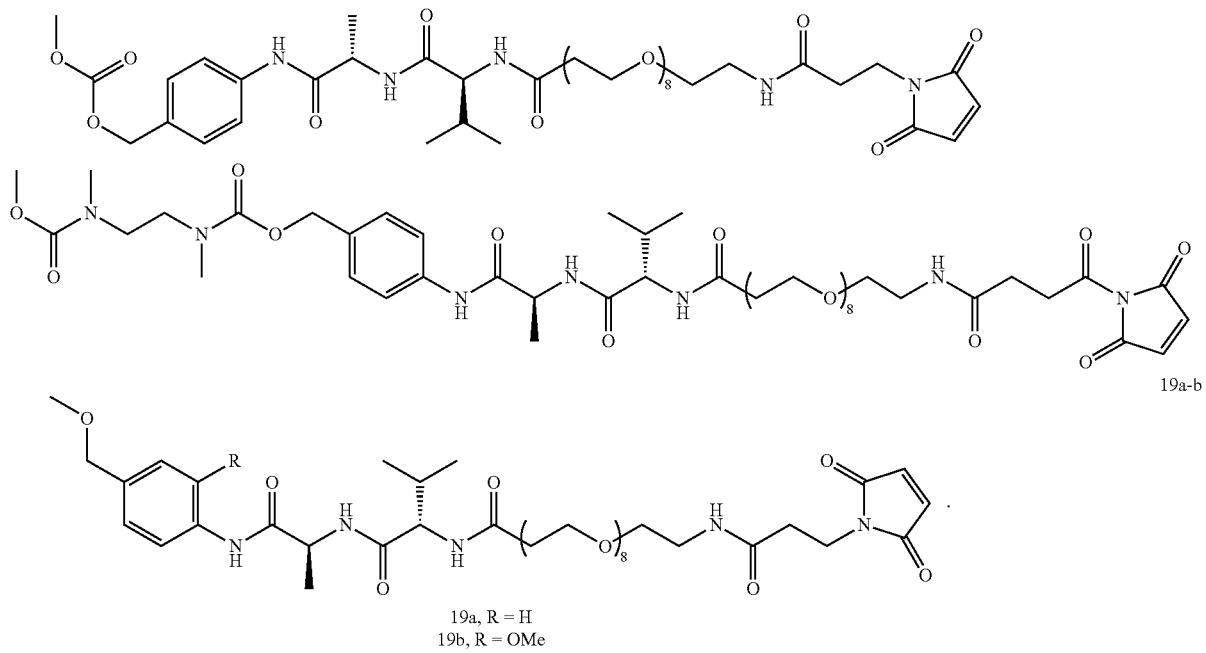

What is claimed is:
1. A compound of Formula I:

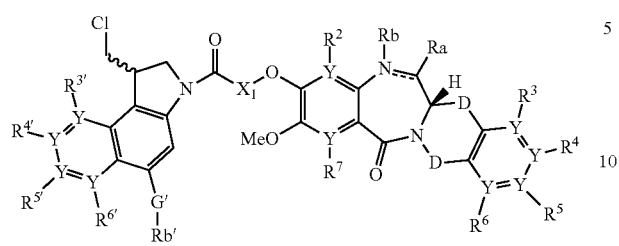

wherein:
- the dotted bond shown between —C($R^a$)— and —N($R^b$)— is independently a single bond or a double bond;
  - when a double bond is present between —C($R^a$)— and —N($R^b$)—, the —C($R^a$)— is olefinic and has a substituent $R^a$, and $R^b$ of the —N($R^b$)— is not present;
  - when a single bond is present between —C($R^a$)— and —N($R^b$)—, the —C($R^a$)— is saturated and has a hydrogen substituent in addition to the $R^a$ substituent and $R^b$ of the —N($R^b$)— is present;
- $R^a$ is independently H, or OH;
- if present, $R^b$ is H, -L-$R_x$ or -L-Sc;
- -L-$R_x$ is a linker L attached to a reactive moiety $R_x$, and -L-$S_c$ is a linker L attached to a substance $S_c$; where L is a bond or is a moiety having 1-200 nonhydrogen atoms selected from C, N, O, S, or halogen, and optionally incorporates ether, oxo, carboxamidyl, urethanyl, heterocyclic, aromatic, or heteroaromatic moieties; $R_x$ is a reactive moiety; $S_c$ is a target binding agent selected from a protein, a portion of a protein, a peptide or a nucleic acid;
- $R^2$ is selected from H, OH, $C_1$-$C_{10}$ alkyl, $C_2$-$C_{10}$ alkenyl or $C_2$-$C_{10}$ alkynyl;
- $R^3$, $R^{3'}$, $R^4$, $R^{4'}$, $R^{6'}$ and $R^6$ are each independently selected from H, OH, $C_1$-$C_{10}$ alkyl, $C_2$-$C_{10}$ alkenyl or $C_2$-$C_{10}$ alkynyl, or, if Y is N, is not present;
- each of $R^5$ or $R^{5'}$ is independently $NH_2$, $CO_2H$, H, OH, $C_1$-$C_{10}$ alkyl, $C_2$-$C_{10}$ alkenyl, $C_2$-$C_{10}$ alkynyl, -L-$R_x$ or -L-Sc, or, if Y is N, is not present;
- $R^7$ is H;
- G'-Rb' is OH, O-L, O-L-Rx, O-L-Sc, $NH_2$, NH-L, NH-L-Rx, or NH-L-Sc;
- each Y is, independently, N or C;
- each D is, independently, ($CH_2$)n where n=0-4, provided that at least one D is ($CH_2$)n where n=1-4;
- X1 is a spacer selected from the group consisting of the following:

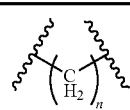

n = 1-8

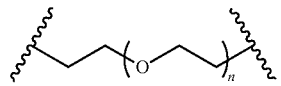

n = 1-8

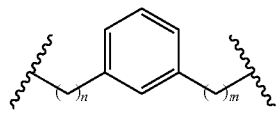

n = 1-8
m = 1-8

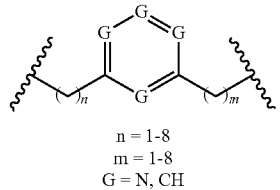

n = 1-8
m = 1-8
G = N, CH

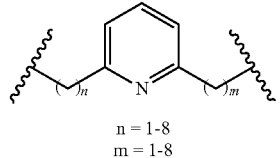

n = 1-8
m = 1-8

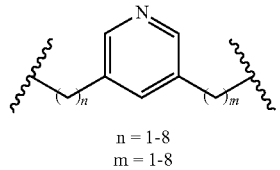

n = 1-8
m = 1-8

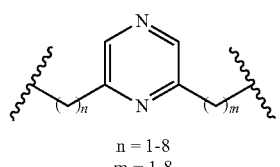

n = 1-8
m = 1-8

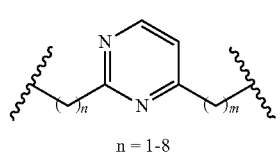

n = 1-8
m = 1-8

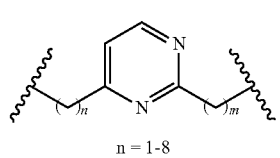

n = 1-8
m = 1-8

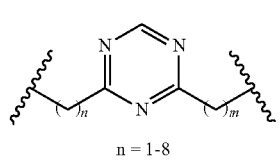

n = 1-8
m = 1-8

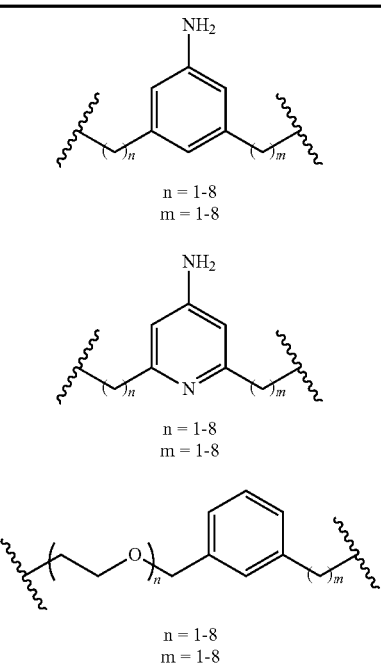
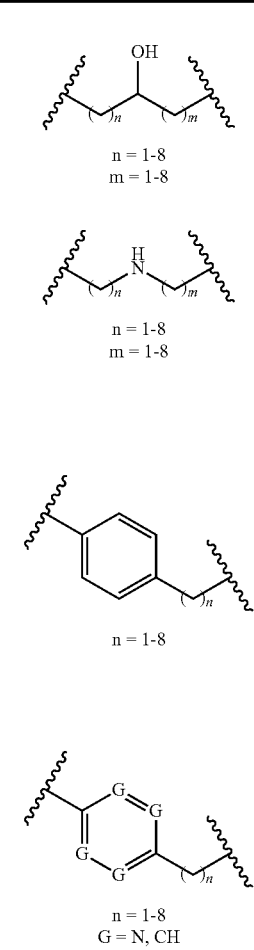
wherein the compound of Formula I has S,S stereochemistry.
2. The compound according to claim 1, wherein $R^b$ is -L-$R_x$.
3. The compound according to claim 1, wherein $R^2$, $R^3$, $R^{3'}$, $R^4$, $R^{4'}$, $R^5$, $R^{5'}$, $R^6$, and $R^{6'}$ are each H.
4. The compound according to claim 1, wherein the compound has any of the following chemical structures:
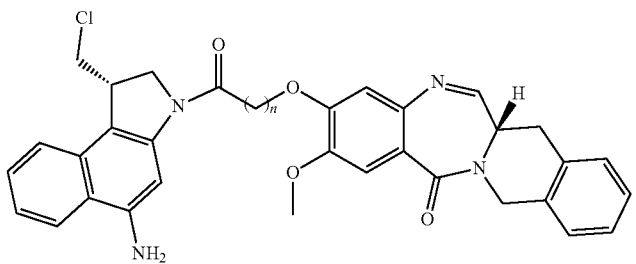
n = 1-8

-continued
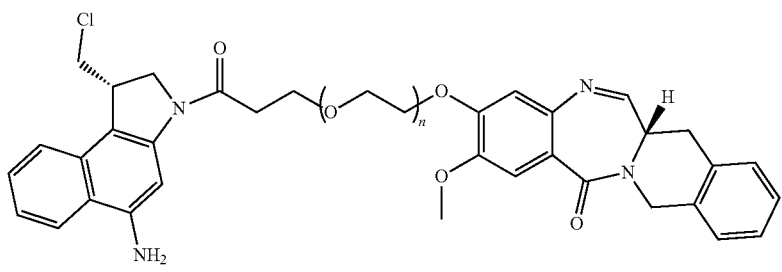
n = 1-8
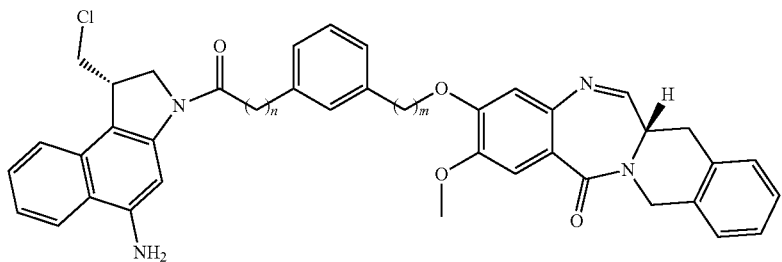
n = 1-8
m = 1-8
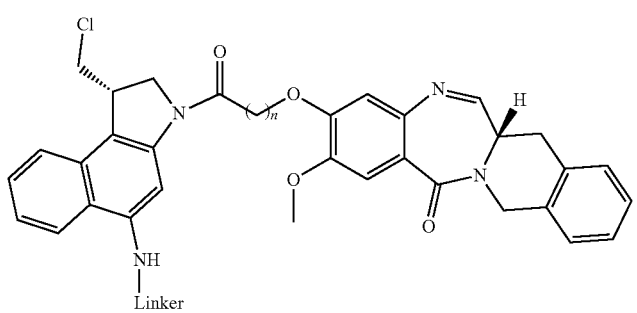
n = 1-8
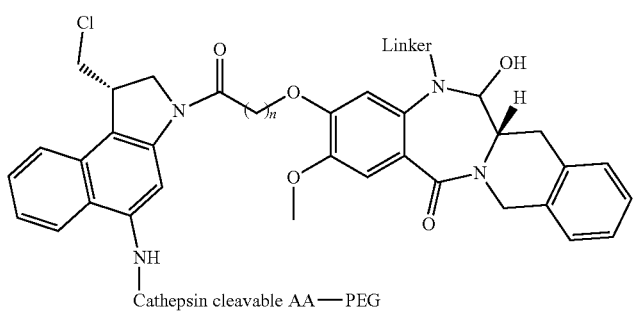
n = 1-8
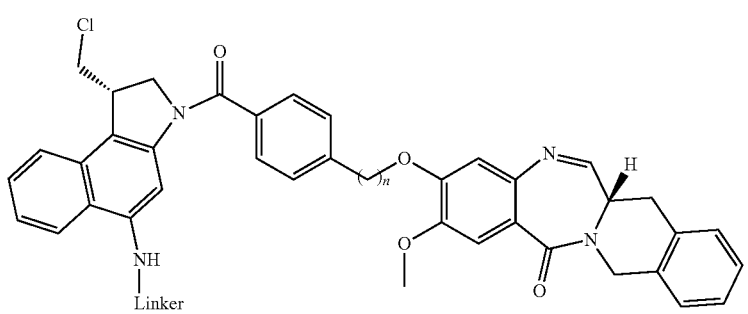
n = 1-8

-continued
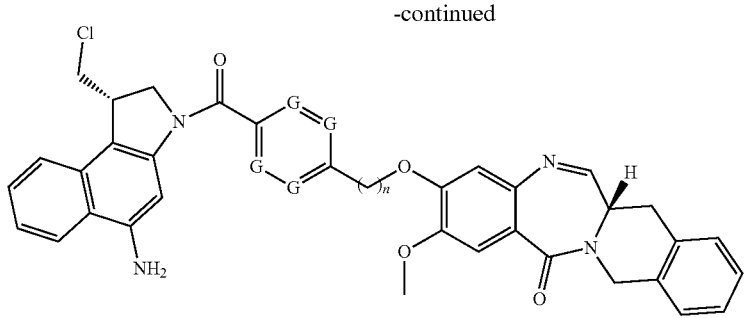
n = 1-8
G = N, CH
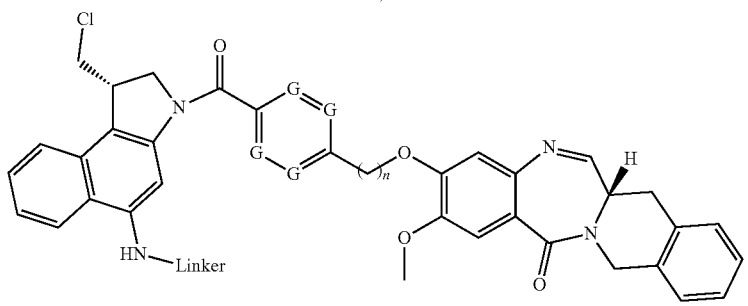
n = 1-8
G = N, CH
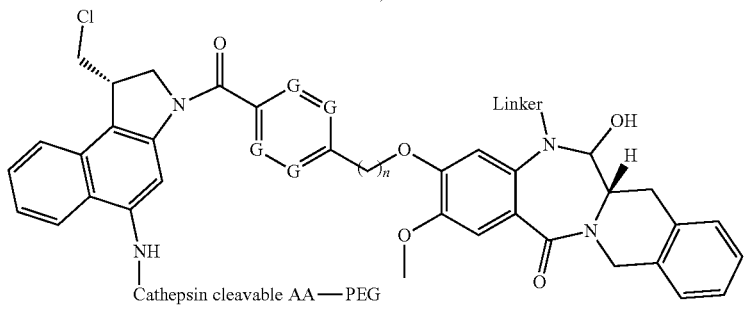
n = 1-8
G = N, CH
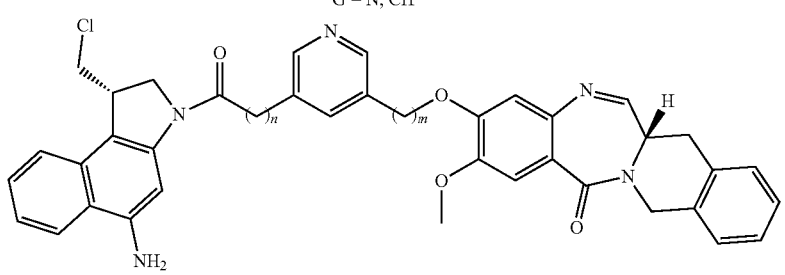
n = 1-8
m = 1-8
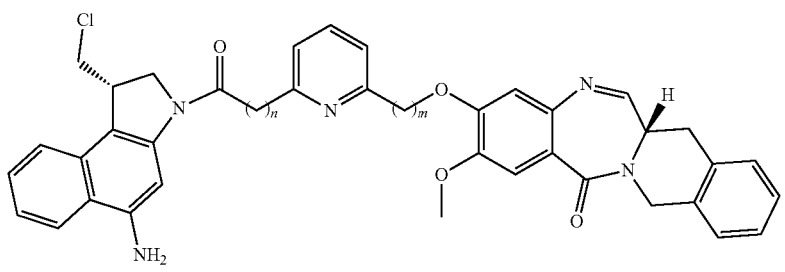
n = 1-8
m = 1-8

-continued
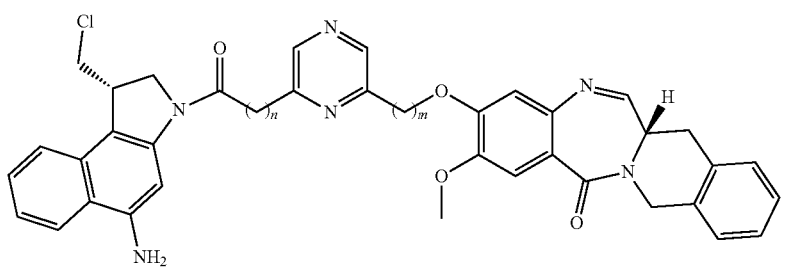
n = 1-8
m = 1-8
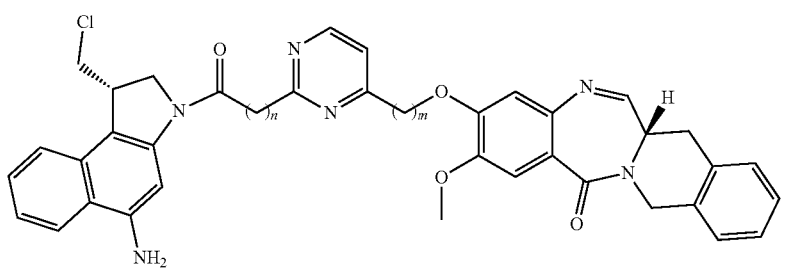
n = 1-8
m = 1-8
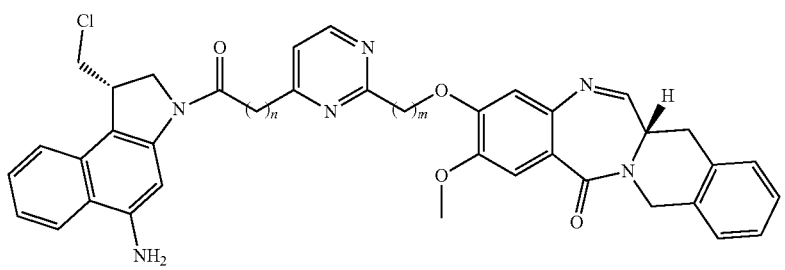
n = 1-8
m = 1-8
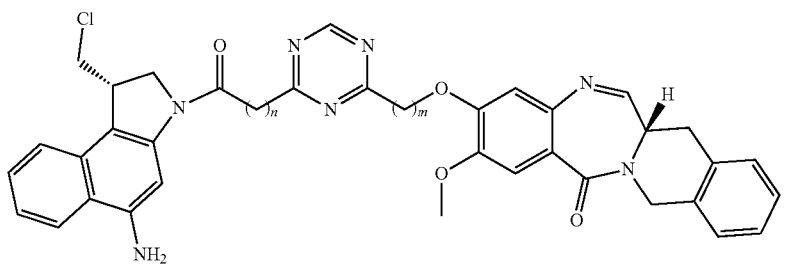
n = 1-8
m = 1-8
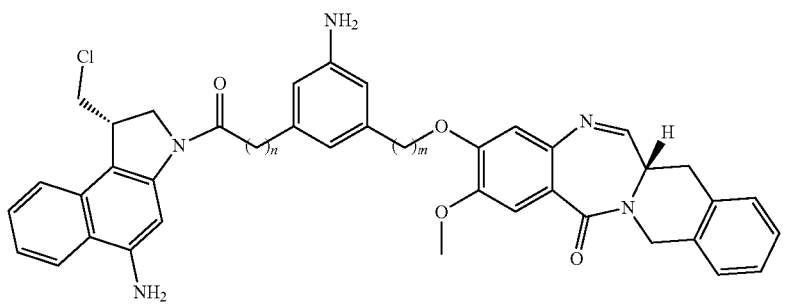
n = 1-8
m = 1-8

-continued
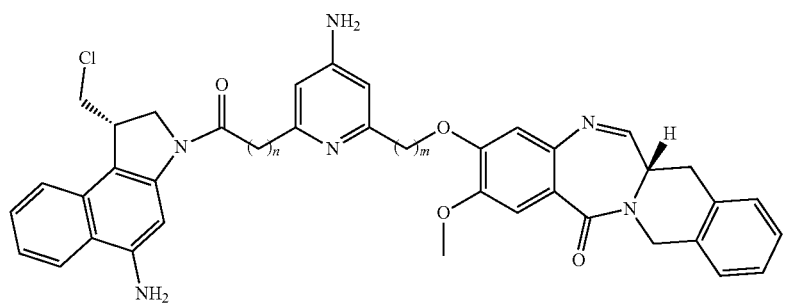
n = 1-8
m = 1-8
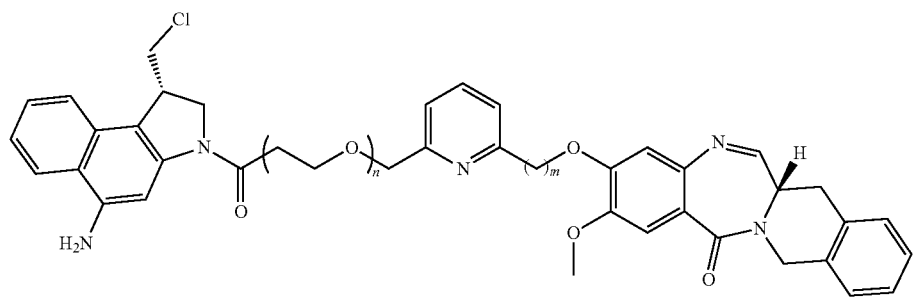
n = 1-8
m = 1-8
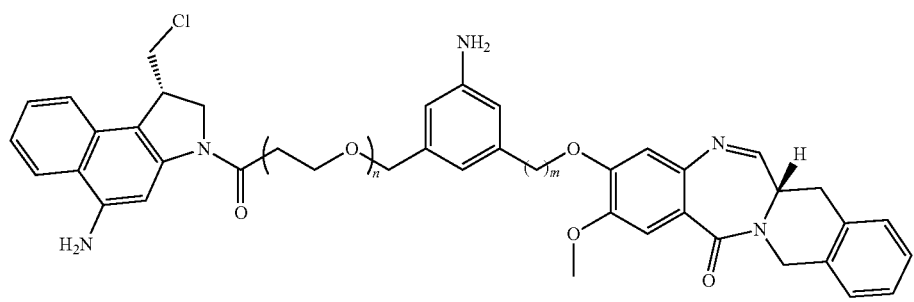
n = 1-8
m = 1-8
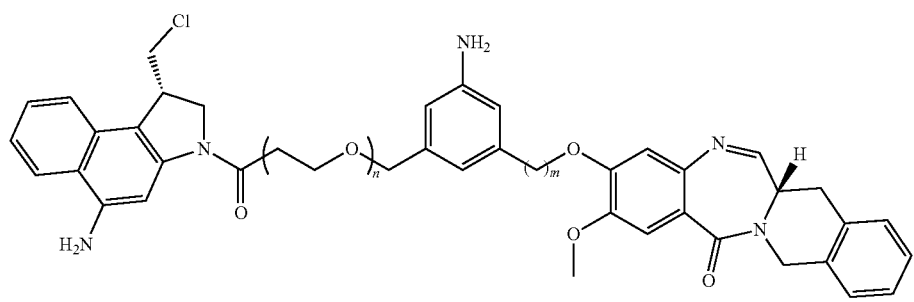
n = 1-8
m = 1-8

-continued
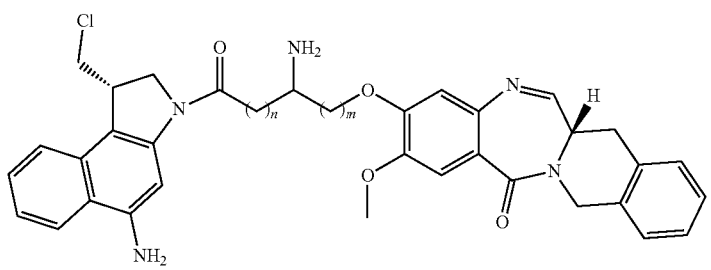
n = 1-8
m = 1-8
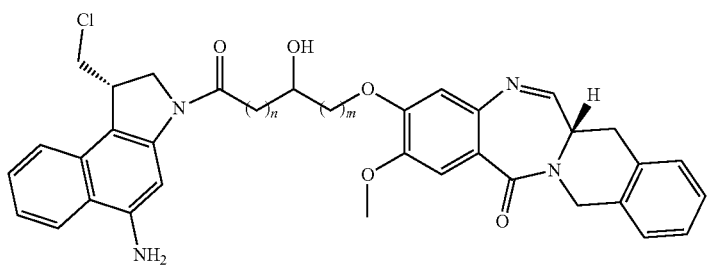
n = 1-8
m = 1-8
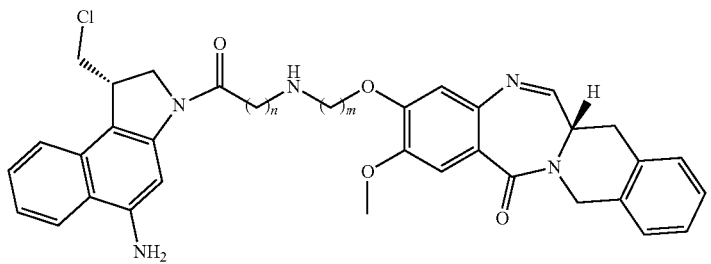
n = 1-8
m = 1-8
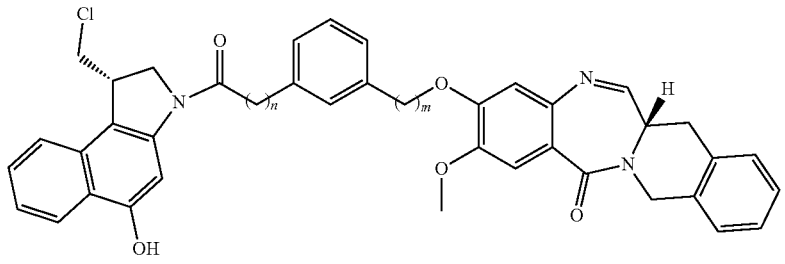
n = 1-8
m = 1-8
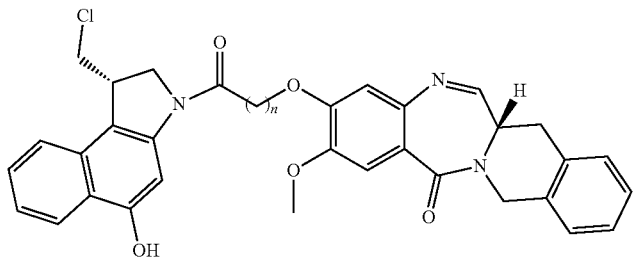
n = 1-8

-continued
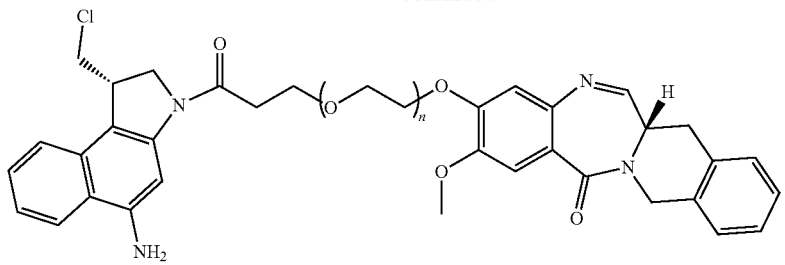
n = 1-8
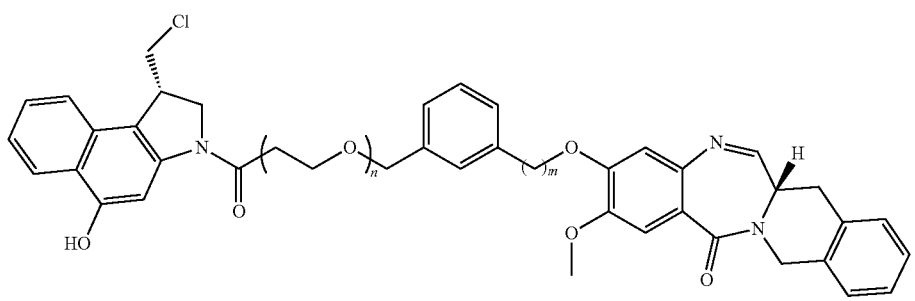
n = 1-8
m = 1-8
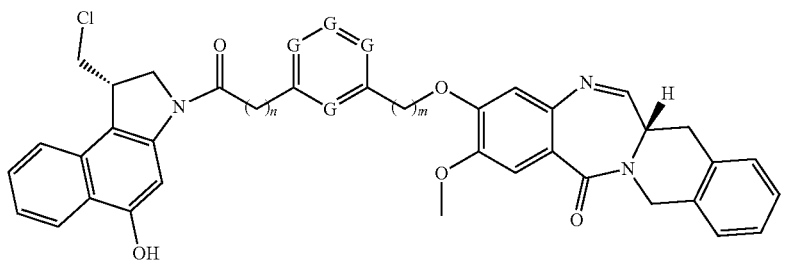
n = 1-8
m = 1-8
G = N, CH
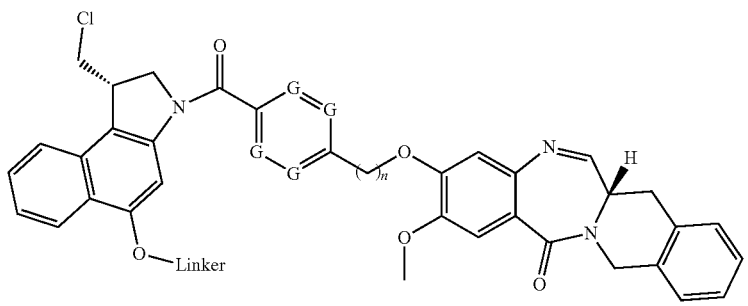
n = 1-8
G = N, CH
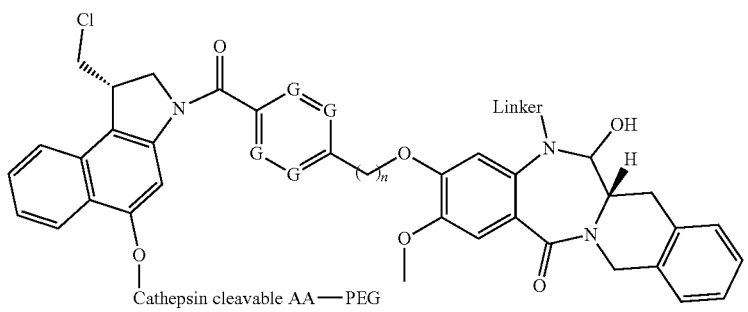
n = 1-8
G = N, CH

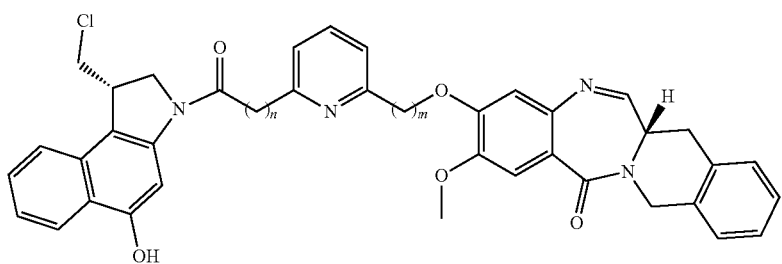
n = 1-8
m = 1-8
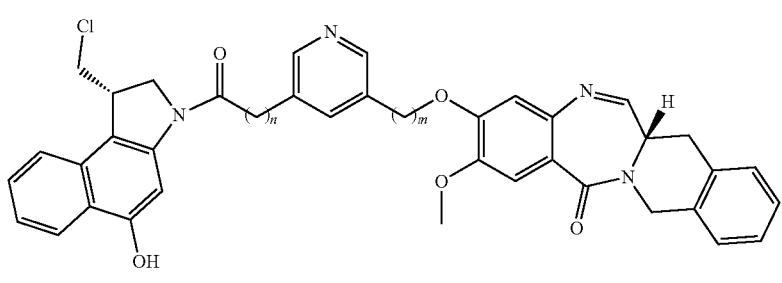
n = 1-8
m = 1-8
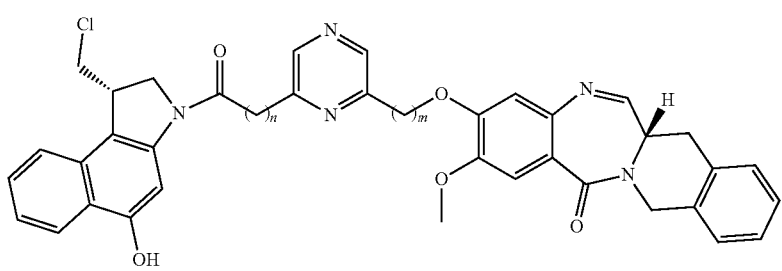
n = 1-8
m = 1-8
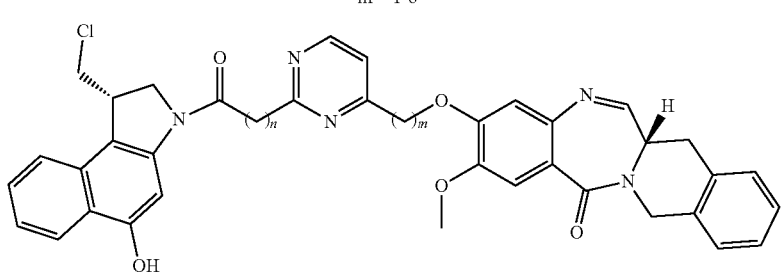
n = 1-8
m = 1-8
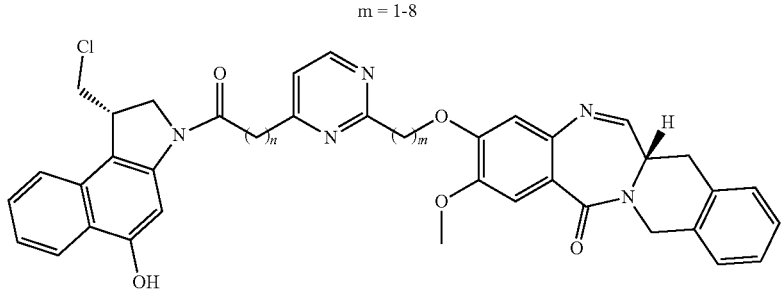
n = 1-8
m = 1-8

-continued
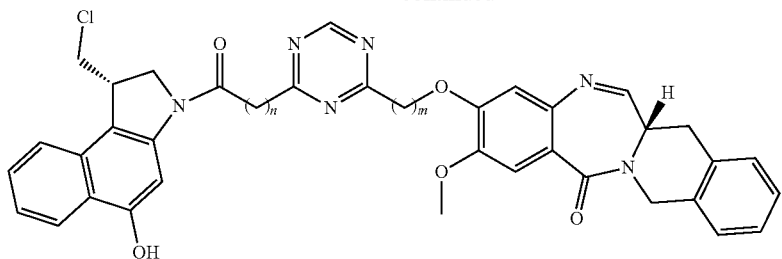
n = 1-8
m = 1-8
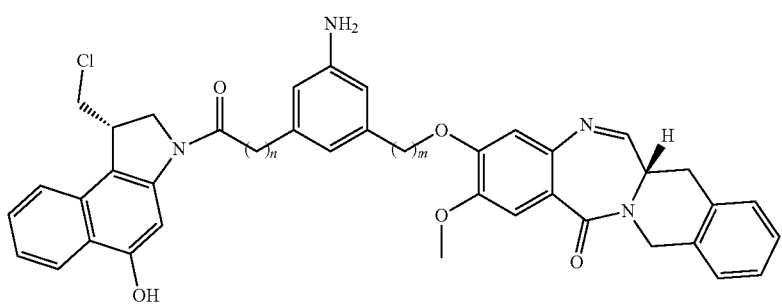
n = 1-8
m = 1-8
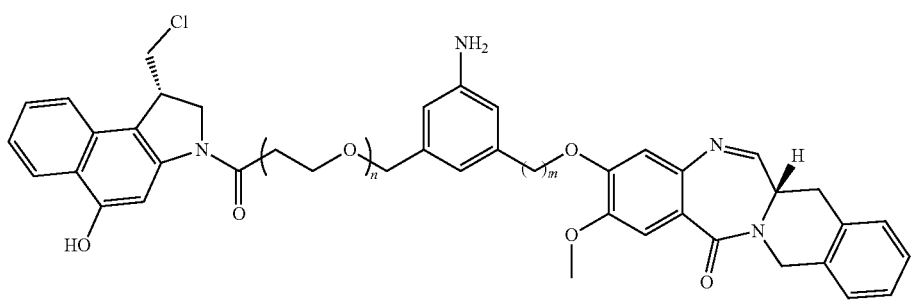
n = 1-8
m = 1-8
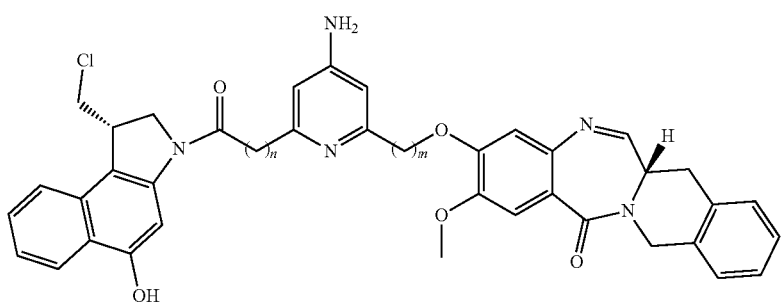
n = 1-8
m = 1-8
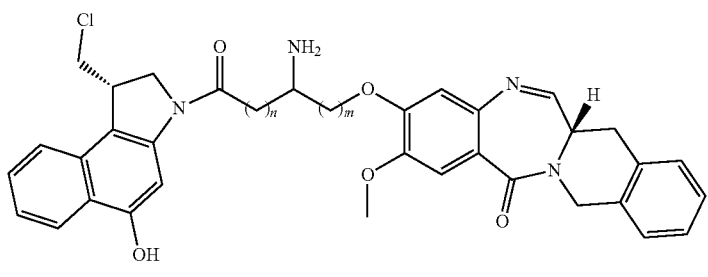
n = 1-8
m = 1-8

-continued
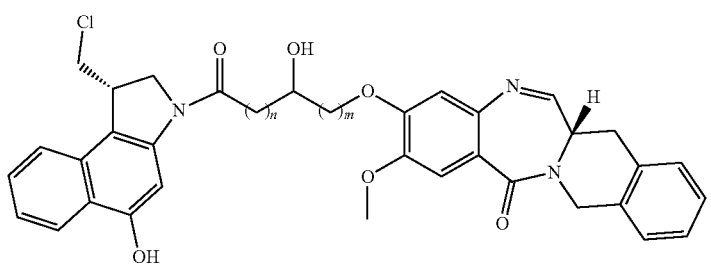
n = 1-8
m = 1-8
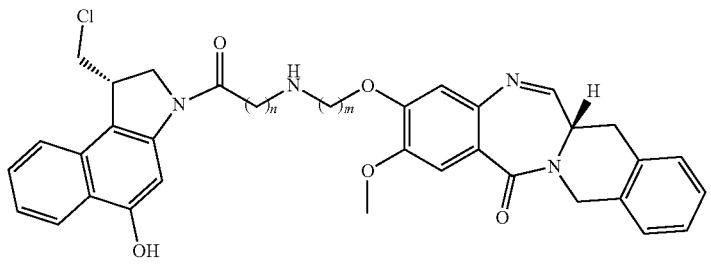
n = 1-8
m = 1-8
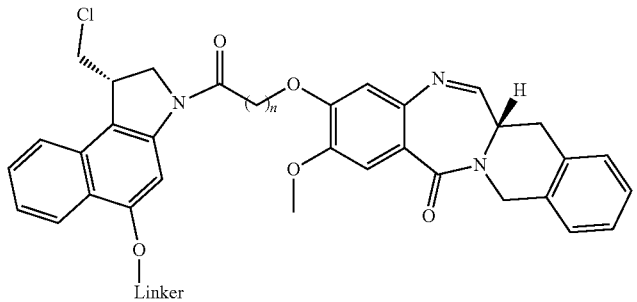
n = 1-8
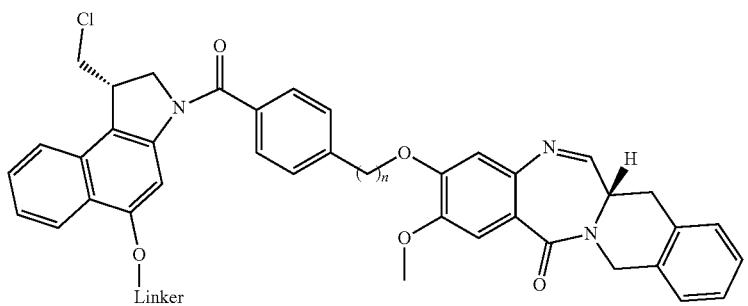
n = 1-8
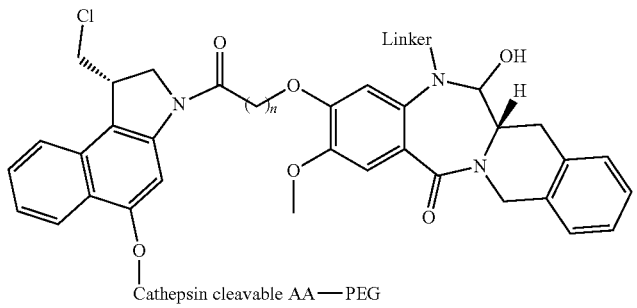
n = 1-8

-continued
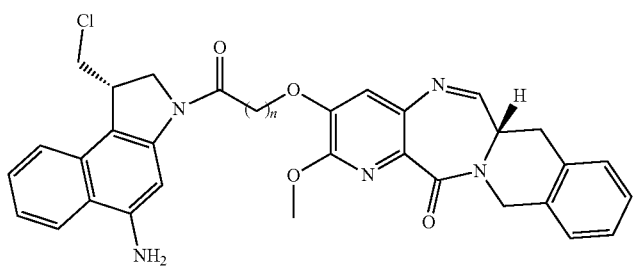
n = 1-8
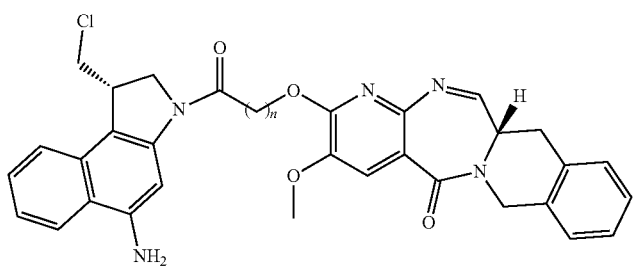
n = 1-8
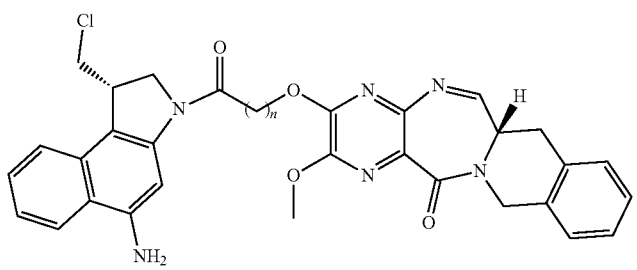
n = 1-8
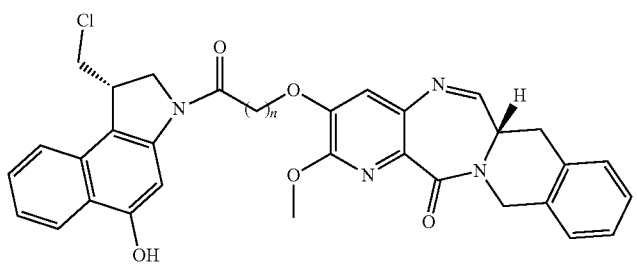
n = 1-8
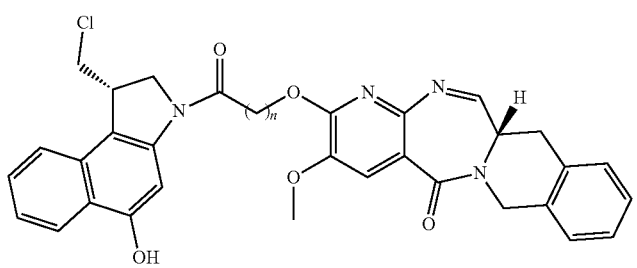
n = 1-8

-continued

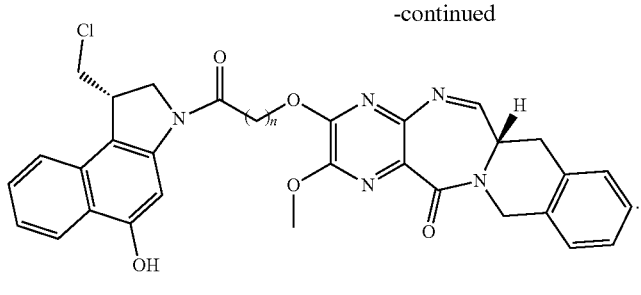

n = 1-8

5. The compound according to claim 1, wherein the compound has a chemical structure of Formula V:

Formula V

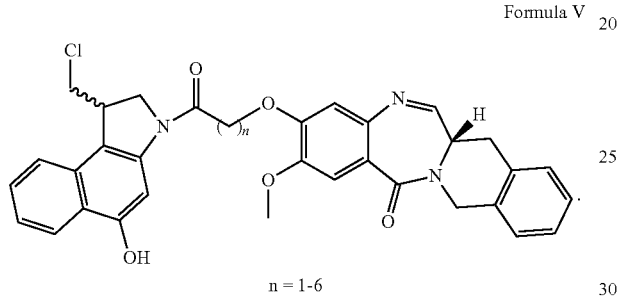

n = 1-6

6. The compound according to claim 1, wherein L is a linker having the structure:

—$Y_L$—$X_{AA}$-PEG-, wherein:
 $Y_L$ is a spacer molecule that links an amino acid unit of $X_{AA}$ to the IQB unit;
 $X_{AA}$ is an amino acid sequence having from 1 to 12 amino acids; and
 PEG is a polyethyleneglycol moiety having the structure:
—$(CH_2CH_2O)_x$—, wherein x is 1, 2, 3, 4, 5, 6, 7, 8, 9, 10, 11, 12, 13, 14, or 15.

7. The compound according to claim 6, wherein $Y_L$ is a spacer molecule selected from the group consisting of

8. The compound according to claim 6, wherein $X_{AA}$ is a dipeptide.

9. The compound according to claim 6, wherein PEG is a polyethyleneglycol moiety having a structure selected from the group consisting of —$(CH_2CH_2O)_x$—, —HN—$(CH_2CH_2O)_x$—C(O)— or —HN—$(CH_2CH_2O)_x$—$CH_2CH_2$—C(O)—, wherein x is 8.

10. The compound according to claim 1, wherein the compound is selected from the following chemical structures:

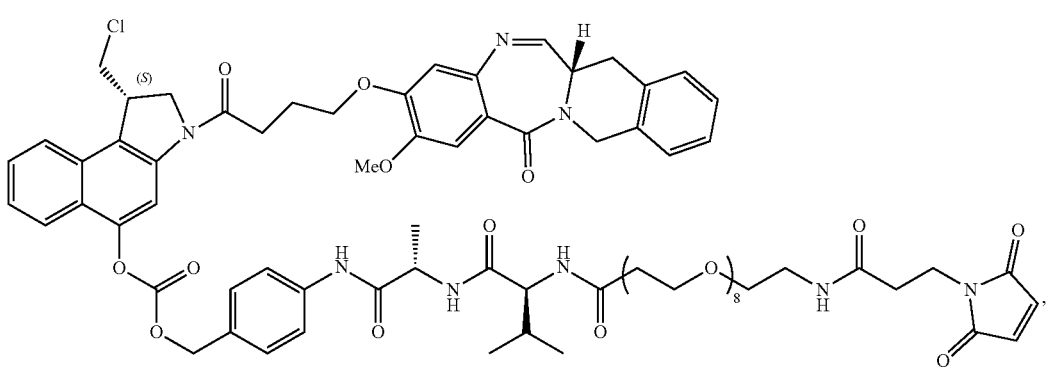

D816

-continued
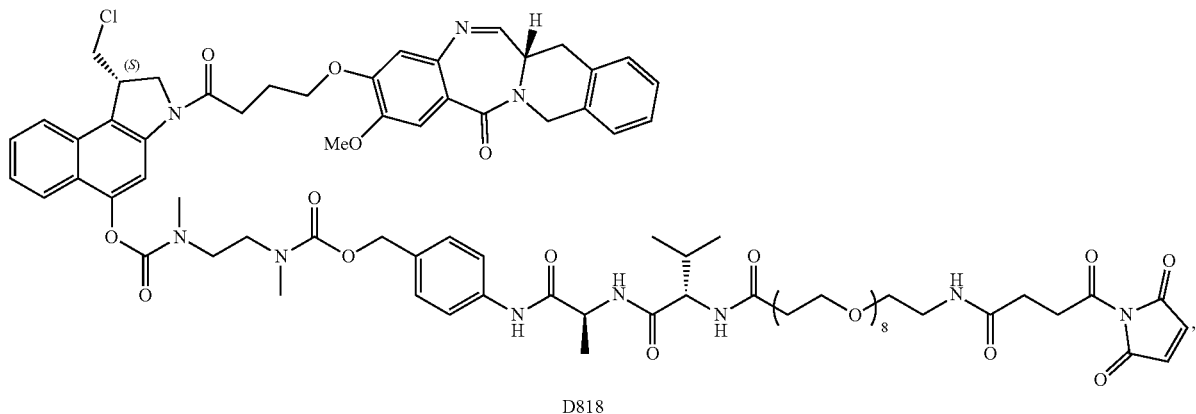
D818
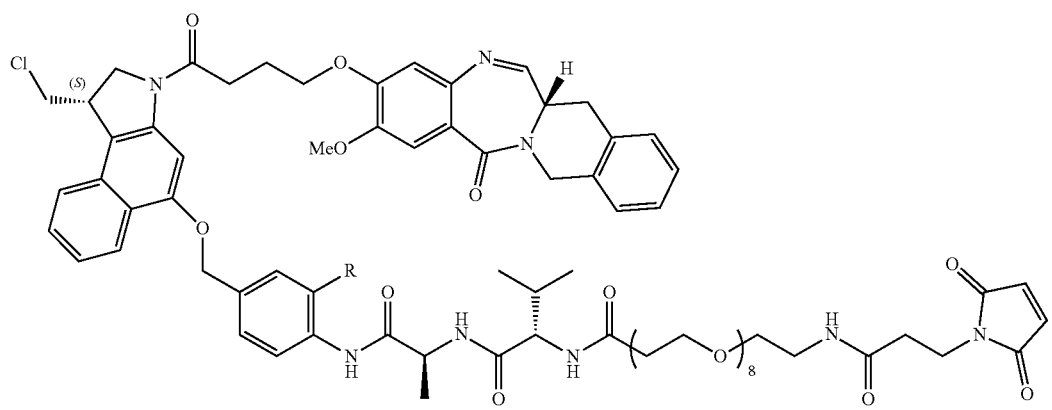
19a, R = H D820b
19b, R = OMe D820
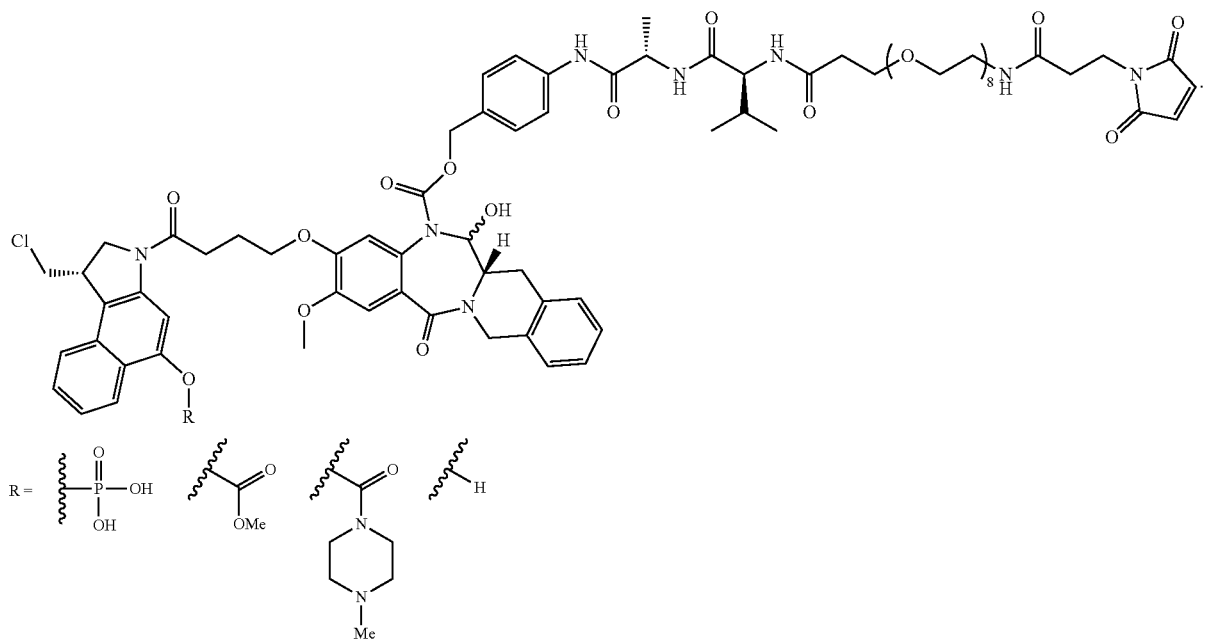
21a/D826   21b/D824   21c/D828   21d/D822